United States Patent
Tal et al.

(10) Patent No.: US 8,181,653 B2
(45) Date of Patent: May 22, 2012

(54) INTRAUTERINE FALLOPIAN TUBE OCCLUSION DEVICE

(75) Inventors: Michael G. Tal, Woodbridge, CT (US); Patrick N. Gutelius, Monroe, CT (US); Mark J. DeBisschop, Burlington, CT (US); Oleg Shikhman, Trumbull, CT (US)

(73) Assignees: Yale University, New Haven, CT (US); Contramed LLC, Charlotte, NC (US)

( * ) Notice: Subject to any disclaimer, the term of this patent is extended or adjusted under 35 U.S.C. 154(b) by 591 days.

(21) Appl. No.: 12/353,770

(22) Filed: Jan. 14, 2009

(65) Prior Publication Data
US 2009/0178682 A1    Jul. 16, 2009

Related U.S. Application Data

(63) Continuation-in-part of application No. 11/892,560, filed on Aug. 23, 2007, now Pat. No. 7,621,276, which is a continuation-in-part of application No. 11/884,027, filed as application No. PCT/US2006/005245 on Feb. 15, 2006, now Pat. No. 7,669,601.

(60) Provisional application No. 61/006,454, filed on Jan. 15, 2008, provisional application No. 60/653,743, filed on Feb. 15, 2005.

(51) Int. Cl.
*A61F 6/06* (2006.01)
(52) U.S. Cl. ........................ 128/831; 128/830
(58) Field of Classification Search ........... 128/830–840
See application file for complete search history.

(56) References Cited

U.S. PATENT DOCUMENTS

| | | | |
|---|---|---|---|
| 3,374,788 A | 3/1968 | Rosenthal | |
| 3,391,844 A | 7/1968 | Vennard et al. | |
| 3,405,711 A | 10/1968 | Bakunin | |
| 3,507,274 A | 4/1970 | Soichet | |
| 3,620,212 A | 11/1971 | Fannon, Jr. et al. | |
| 3,659,596 A | 5/1972 | Robinson | |
| 3,678,927 A | 7/1972 | Soichet | |
| 3,687,129 A | 8/1972 | Nuwayser | |
| 3,704,704 A | 12/1972 | Gonzales | |
| 3,789,838 A | 2/1974 | Fournier et al. | |
| 3,805,767 A | 4/1974 | Erb | |
| 3,811,435 A | 5/1974 | Soichet | |
| 3,918,443 A | 11/1975 | Vennard et al. | |

(Continued)

FOREIGN PATENT DOCUMENTS
JP    59-0214444    2/1984
(Continued)

*Primary Examiner* — Kim M Lewis
(74) *Attorney, Agent, or Firm* — Welsh Flaxman & Gitler LLC

(57) ABSTRACT

An intrauterine device for occluding orifices of fallopian tubes includes a resilient body having an elongated member with a first end and a second end. The elongated member further includes a first leg ending with the first end of the elongated member, a second leg ending with the second end of the elongated member and a connection member positioned therebetween. A first orifice plug is secured at the first end of the elongated member and a second orifice plug is secured at the second end of the elongated member. The first and second orifice plugs are shaped and dimensioned to seat at the orifices of the fallopian tubes or within the fallopian tubes as the elongated member spreads outwardly with the first end and second end moving apart.

27 Claims, 40 Drawing Sheets

U.S. PATENT DOCUMENTS

| | | | |
|---|---|---|---|
| 4,353,363 A | 10/1982 | Sopena Quesada | |
| 4,537,186 A | 8/1985 | Verschoof et al. | |
| 4,612,924 A | 9/1986 | Cimber | |
| 4,628,924 A | 12/1986 | Cimber | |
| 4,932,421 A | 6/1990 | Kaali et al. | |
| 5,095,917 A | 3/1992 | Vancaillie | |
| 5,146,931 A | 9/1992 | Kurz | |
| 5,555,896 A | 9/1996 | Cimber | |
| 5,935,137 A | 8/1999 | Saadat et al. | |
| 6,042,030 A | 3/2000 | Howe et al. | |
| 6,346,102 B1 | 2/2002 | Harrington et al. | |
| 6,705,323 B1 | 3/2004 | Nikolchev et al. | |
| 2002/0198547 A1 | 12/2002 | Schultz | |
| 2003/0066533 A1 | 4/2003 | Loy | |
| 2004/0009205 A1 | 1/2004 | Sawhney | |
| 2005/0125022 A1 | 6/2005 | Ravikumar et al. | |
| 2005/0171569 A1* | 8/2005 | Girard et al. | 606/193 |
| 2005/0192616 A1 | 9/2005 | Callister et al. | |
| 2008/0302368 A1 | 12/2008 | McGuckin, Jr. et al. | |

FOREIGN PATENT DOCUMENTS

| | | |
|---|---|---|
| JP | 61-42914 | 3/1986 |
| WO | WO2006/088909 | 8/2006 |

\* cited by examiner

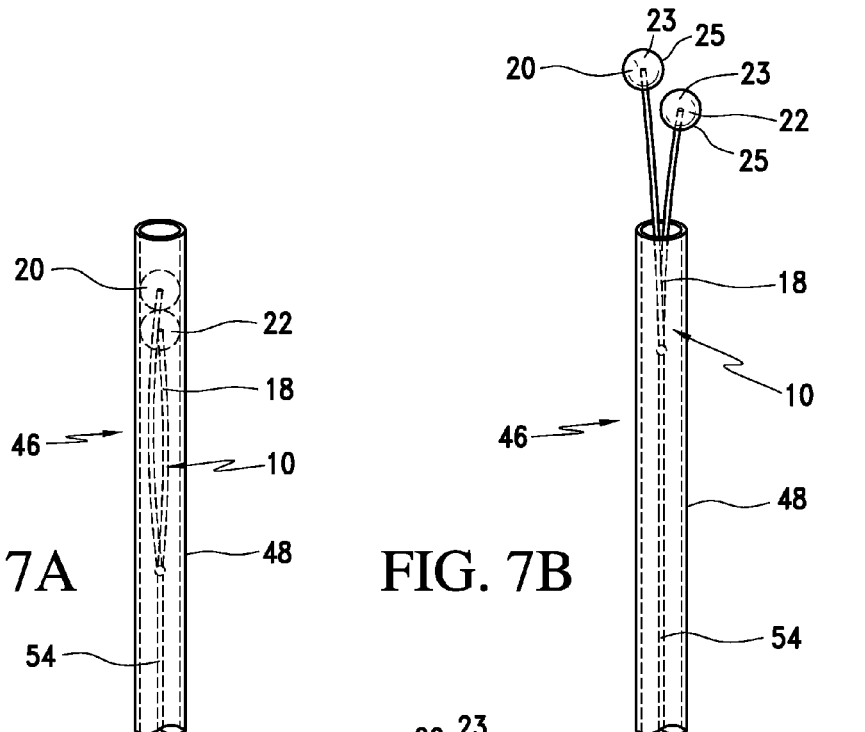
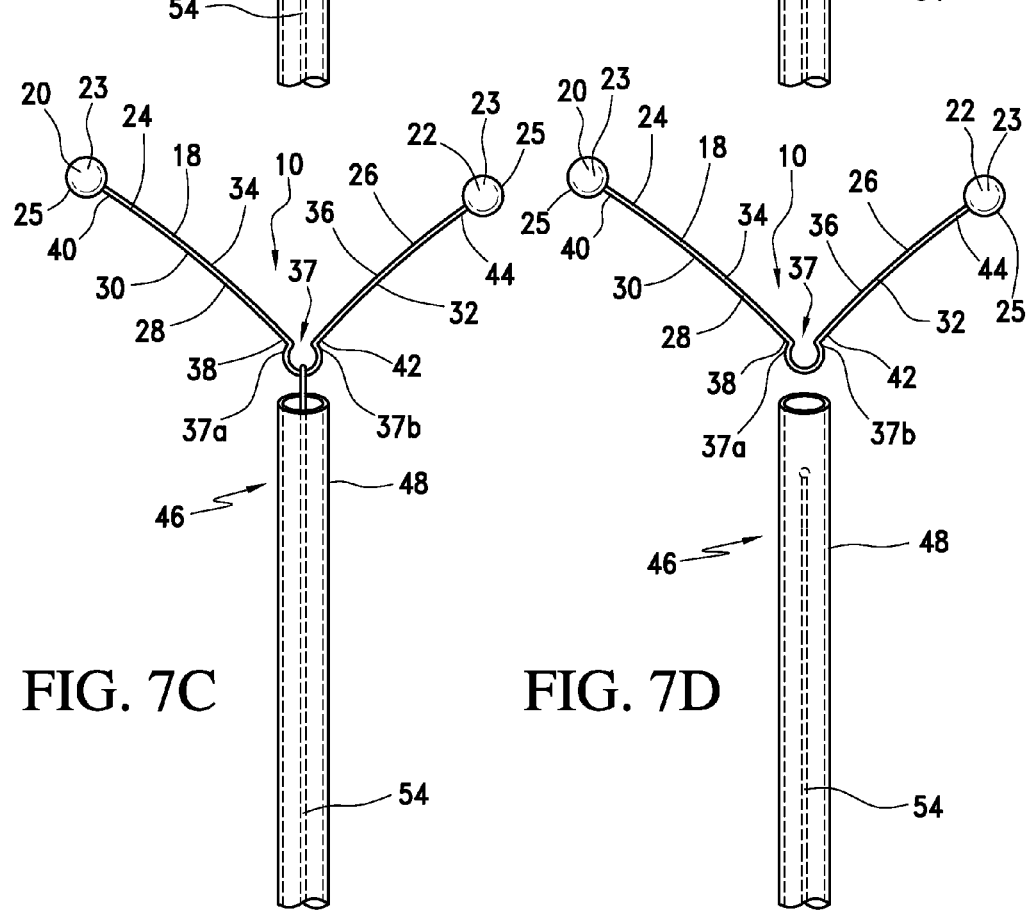
FIG. 7A  FIG. 7B  FIG. 7C  FIG. 7D

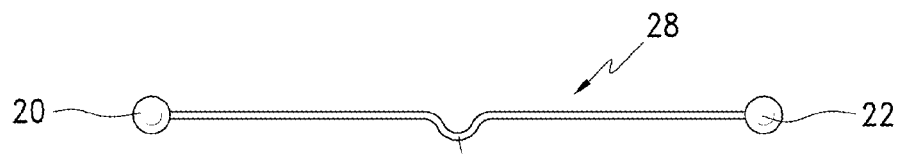
FIG. 26
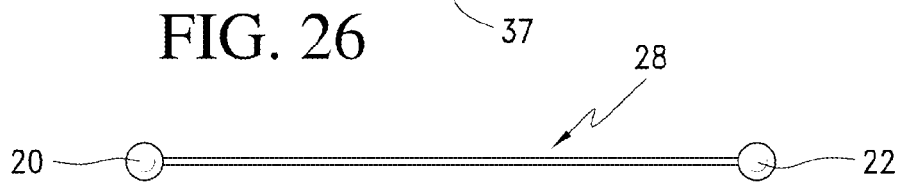
FIG. 27
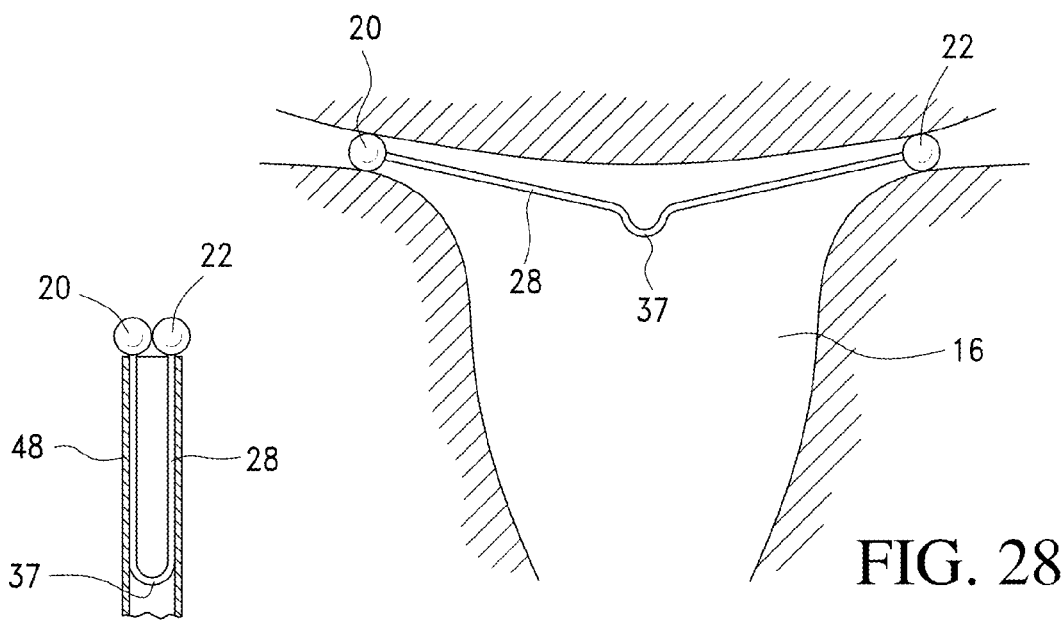
FIG. 28
FIG. 29
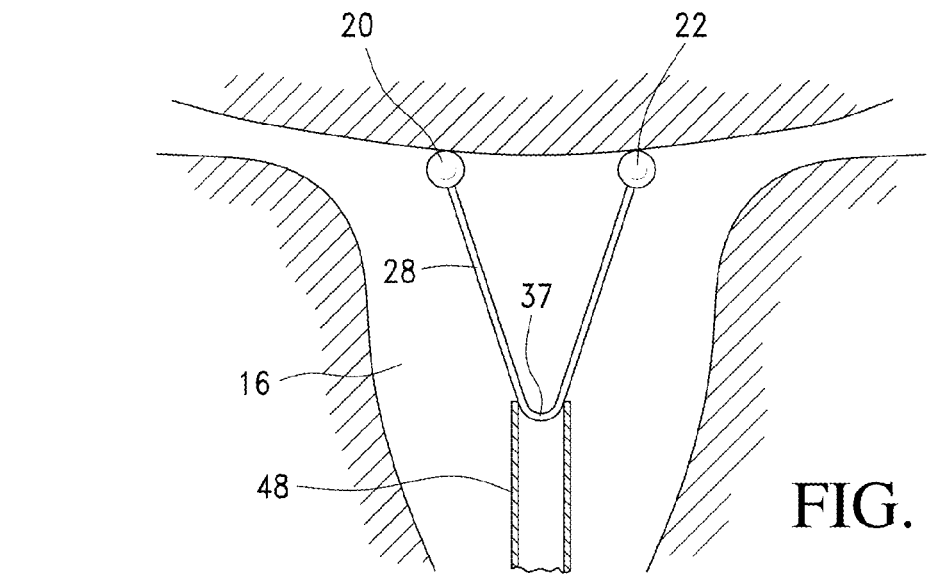
FIG. 30

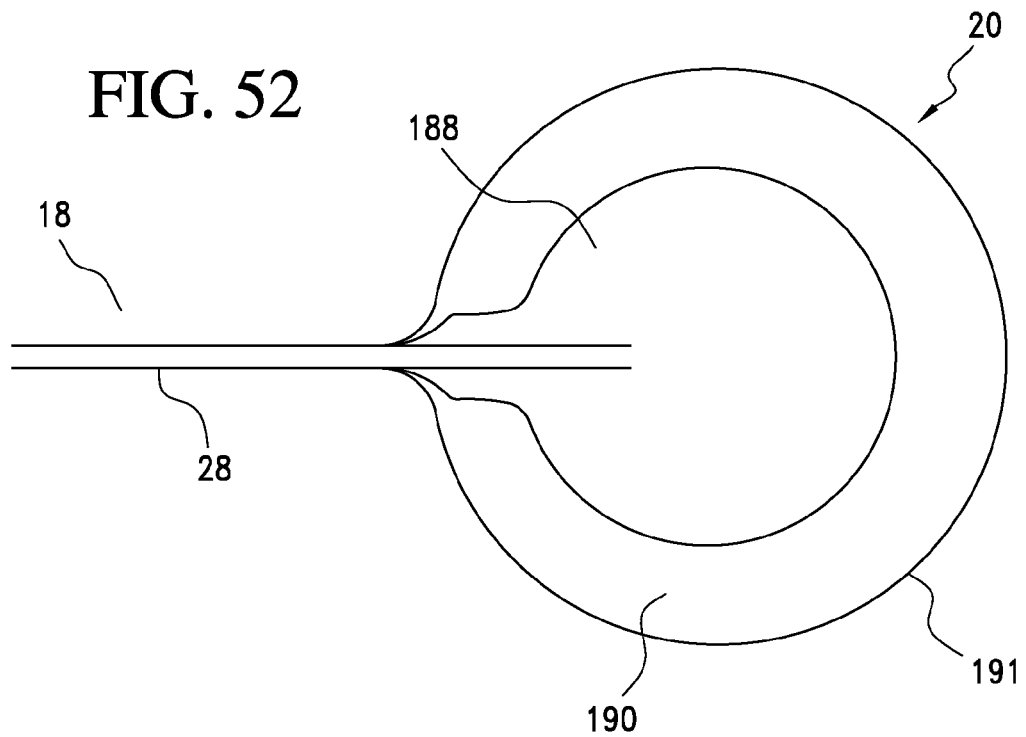
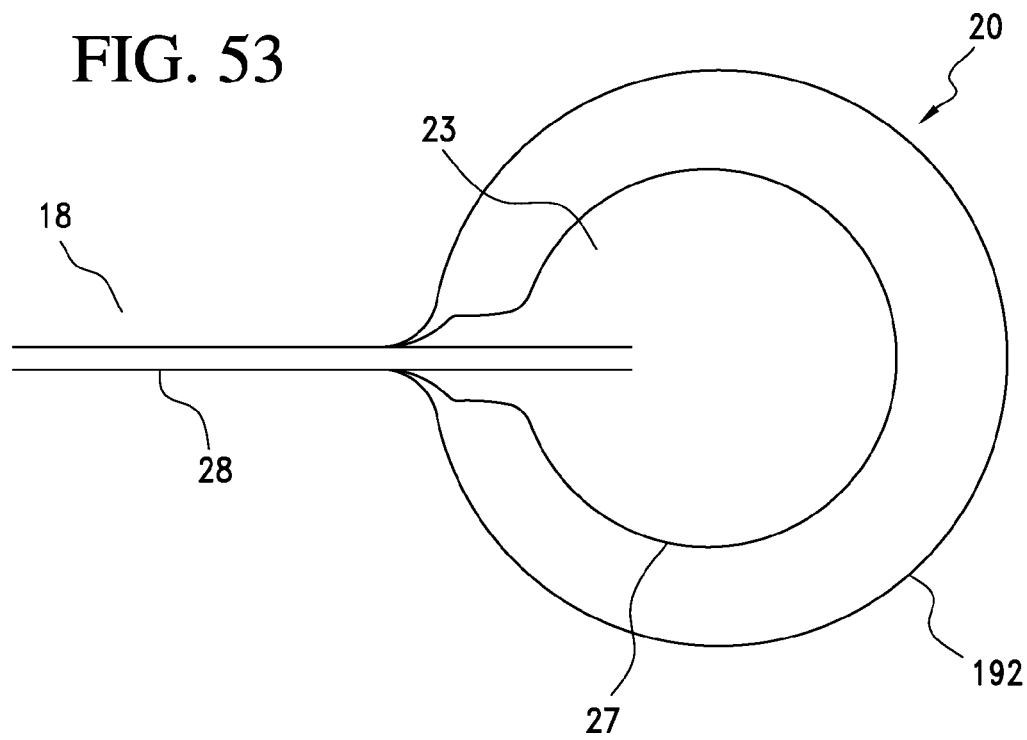

INTRAUTERINE FALLOPIAN TUBE OCCLUSION DEVICE

CROSS REFERENCE TO RELATED APPLICATIONS

This applications claims the benefit of U.S. Provisional Application Ser. No. 61/006,454, filed Jan. 15, 2008, entitled "INTRAUTERINE FALLOPIAN TUBE OCCLUSION DEVICE", and this application is a continuation-in-part of U.S. patent application Ser. No. 11/892,560, filed Aug. 23, 2007, entitled "INTRAUTERINE FALLOPIAN TUBE OCCLUSION DEVICE", now U.S. Pat. No. 7,621,276, which is continuation-in-part of U.S. patent application Ser. No. 11/884,027, filed Aug. 9, 2007, entitled "INTRAUTERINE FALLOPIAN TUBE OCCLUSION DEVICE AND METHOD FOR USE", now U.S. Pat. No. 7,669,601, which is the National Stage of International Application No. PCT/US2006/005245, filed Feb. 15, 2006, entitled "INTRAUTERINE FALLOPIAN TUBE OCCLUSION DEVICE AND METHOD FOR USE", which claims the benefit of U.S. Provisional Patent Application Ser. No. 60/653,743, filed Feb. 15, 2005, entitled "INTRAUTERINE FALLOPIAN TUBE OCCLUSION DEVICE".

BACKGROUND OF THE INVENTION

1. Field of the Invention

The invention relates to a fallopian tube occlusion device and method for use. More particularly, the invention relates to a fallopian tube occlusion device that uses the unique shape of the uterine cavity to ensure delivery and proper positioning thereof through the application of barrier members specifically structured for seating within the uterus and/or fallopian tube anatomy in a manner creating a barrier. The invention also relates to a delivery mechanism utilizing the device described herein to deliver medication and/or other therapeutic agents to the uterus and/or fallopian tube anatomy.

2. Description of the Related Art

Several types of intrauterine devices (IUDs) are available and used worldwide. There are inert IUDs, copper IUDs and hormone impregnated IUDs. There is ongoing controversy regarding the mechanisms of action of IUDs in humans. Classically, the view was that the IUD in humans acted predominantly after fertilization to prevent implantation, but evidence has accumulated for some effects before fertilization. As a general rule, the pre-fertilization effects are not enough to prevent fertilization and, therefore, the post-fertilization effects are most important. The post-fertilization mechanisms of action of the IUD include slowing or speeding the transport of the early embryo through the fallopian tube, damage to or destruction of the early embryo before it reaches the uterus, and prevention of implantation. This mechanism of action is perceived as an early abortion by some, and prevents many patients from using IUDs as a temporary mode of contraception. Another problem with IUDs is expulsion from the uterus and subsequent unwanted pregnancy. Other potential complications of IUDs are uterine infection, uterine perforation and most important ectopic pregnancy. Ectopic pregnancy is a condition where the embryo has implanted outside of the uterine cavity, usually in the fallopian tube. This condition is also hazardous to the patient and can lead to internal bleeding and severe morbidity and even mortality. This potential complication also deters patients from the use of IUDs.

Another problem affecting many women is endometriosis. One of the proposed mechanisms of endometriosis is flow of the menstrual blood through the fallopian tubes into the peritoneal cavity. This condition usually affects younger patients and permanent tubal ligation or occlusion is not warranted. It is thought that temporary tubal occlusion might prevent the flow of blood through the fallopian tubes and into the peritoneal cavity and thus might improve the patient's symptoms.

Fallopian tube ligation is usually performed surgically. Transvaginal tubal occlusion has also been described before. There are several methods of tubal ligation and occlusion.

With the foregoing in mind, a need exists for an improved intrauterine system replacing currently marketed IUDs and other methods of contraception, such as, tubal ligation.

SUMMARY OF THE INVENTION

It is, therefore, an object of the present invention to provide an intrauterine device for positioning at or within orifices of fallopian tubes. The intrauterine device includes a resilient body having an elongated member with a first end and a second end. The elongated member further includes a first leg ending with the first end of the elongated member, a second leg ending with the second end of the elongated member and a connection member positioned therebetween. A first orifice plug is secured at the first end of the elongated member and a second orifice plug is secured at the second end of the elongated member. The first and second orifice plugs are shaped and dimensioned to seat at the orifices of the fallopian tubes or within the fallopian tubes as the elongated member spreads outwardly with the first end and second end moving apart.

It is also an object of the present invention to provide an intrauterine device wherein the first orifice plug and the second orifice plug slide along the resilient body.

It is another object of the present invention to provide an intrauterine device wherein upon insertion, the first orifice plug and the second orifice plug are located at a position adjacent the connection member linking the first leg and second leg, and the first orifice plug and the second orifice plug are respectively moved upwardly along the first leg and the second leg to a position adjacent the second ends of the respective first leg and the second leg where the first orifice plug and the second orifice plug are positioned within the fallopian tubes.

It is a further object of the present invention to provide an intrauterine device wherein each of the first orifice plug and the second orifice plug includes a central bearing aperture through which the resilient body passes.

It is also an object of the present invention to provide an intrauterine device wherein the first orifice plug and the second orifice plug are releasably secured to the respective first end and second end of the resilient body via a snap-type connection.

It is another object of the present invention to provide an intrauterine device wherein each of the first orifice plug and the second orifice plug includes a central cavity having a resilient external flange controlling access to the central cavity and each of the first leg and the second leg includes a ball at a distal end thereof. The ball is slightly larger than the flange, wherein applied pressure to the flange will allow pushing of the ball therethrough and into the central cavity of the respective first orifice plug and the second orifice plug such that the respective first orifice plug and second orifice plug are selectively secured to the first end and the second end of the resilient body until such a time that the respective first leg and the second leg are pulled from the first orifice plug and the second orifice plug to withdraw the ball from the central cavity and through the flange.

It is a further object of the present invention to provide an intrauterine device wherein the first orifice plug and the second orifice plug are releasably secured to the respective first end and second end of the resilient body via a resorbable coupling member.

It is also an object of the present invention to provide an intrauterine device wherein the elongated member extends between a folded configuration when stored for deployment and a substantially straight configuration when the first and second orifice plugs are positioned within the fallopian tubes.

It is another object of the present invention to provide an intrauterine device wherein the first leg includes a first end and a second end, the second end being connected to the first orifice plug, and the second end of the first leg includes a reduced diameter section allowing for greater flexibility in an area adjacent the first orifice plug. The second leg includes a first end and a second end, the second end being connected to the second orifice plug, and the second end of the second leg includes a reduced diameter section allowing for greater flexibility in an area adjacent the second orifice plugs.

It is a further object of the present invention to provide an intrauterine device wherein the first orifice plug includes a plurality of orifice plug members.

It is also an object of the present invention to provide an intrauterine device wherein the orifice plug members increase in size as they move from a second end of the first leg to a more proximal position along the first leg.

It is another object of the present invention to provide an intrauterine device wherein a distal most orifice plug member is spherical and each of the remaining orifice plug members includes a distal end and a proximal end and each of the orifice plug members is formed in the shape of a substantially truncated cone with a diameter thereof increasing as the orifice plug member extends from the distal end thereof to the proximal end thereof.

It is a further object of the present invention to provide an intrauterine device wherein the first leg and the second leg are tubular allowing for the transport of an injectable material to the respective first orifice plug and the second orifice plug.

It is also an object of the present invention to provide an intrauterine device wherein each of the first and second orifice plugs are made of a material allowing transport of the injectable material from the respective first and second legs through the first and second orifice plugs and to the selected tissue.

It is another object of the present invention to provide an intrauterine device wherein the resilient body applies a load of approximately 5 to 50 grams when the first orifice plug and the second orifice plug are between approximately 18 mm and 54 mm apart.

It is a further object of the present invention to provide an intrauterine device wherein the resilient body extends to spread the first orifice plug and the second orifice plug, when deployed within respective orifices of the fallopian tubes, from approximately 18 mm to approximately 54 mm.

It is also an object of the present invention to provide an intrauterine device wherein a substantially constant load is applied by the resilient body when the first orifice plug and the second orifice plug are spaced within the range of approximately 18 mm to approximately 54 mm.

It is another object of the present invention to provide an intrauterine device wherein the load applied is between approximately 15 and 30 grams.

It is a further object of the present invention to provide an intrauterine device wherein the first orifice plug and the second orifice plug are composed of materials encouraging tissue in-growth.

It is also an object of the present invention to provide an intrauterine device wherein the first orifice plug and the second orifice plug are composed of bioresorbable or bioabsorbable materials.

It is another object of the present invention to provide an intrauterine device wherein the intrauterine device includes a first leg and second leg connected to each other for controlled relative movement. The first leg includes a first end and a second end wherein a first orifice plug is secured to the second end of the first leg and the second leg includes a first end and a second end wherein a second orifice plug is secured to the second end of the second leg. The first leg and the second leg are selectively moveable to adjust a distance between the first orifice plug and the second orifice plug.

It is a further object of the present invention to provide an intrauterine device including a clamping member connecting the first leg to the second leg for controlled relative movement.

It is also an object of the present invention to provide an intrauterine device wherein the clamping member is an elongated member including first and second apertures shaped and dimensioned for receiving the respective first ends of the first leg and second leg in a manner permitting relative movement of the first and second leg, and ultimately, the first and second orifice plugs, as the first and second legs are moved within the clamping member.

It is also an object of the present invention to provide an intrauterine device wherein the clamping member is crimped to lock the first leg and the second leg in position relative to the clamping member.

It is another object of the present invention to provide an intrauterine device wherein the respective first ends of the first and second legs are formed in a telescopic mating relationship.

It is a further object of the present invention to provide an occlusion device wherein the first end of the first leg includes a central threaded passageway shaped and dimensioned for receiving the threaded first end of the second leg in a threaded mating configuration.

It is also an object of the present invention to provide a method for occluding the fallopian tubes including first delivering an intrauterine device into the uterine cavity. The occlusion device includes an elongated member with a first end and second end, and a first orifice plug secured at the first end of the elongated member and a second orifice plug secured at the second end of the elongated member. The method further includes causing the occlusion device to apply pressure within the uterine cavity in a manner causing irritation and encouraging tissue in-growth into the first orifice plug and the second orifice plug.

It is another object of the present invention to provide a method for delivering an intrauterine device. The method is achieved by advancing the intrauterine device into the uterine cavity, the intrauterine device including an elongated member with a first end and second end, and a first orifice plug secured at the first end of the elongated member and a second orifice plug secured at the second end of the elongated member. The intrauterine device is then released. Release results in (a) the first and second orifice plugs first moving outwardly due to stored outward bias in the elongated member, (b) the first and second orifice plugs then moving upwardly within the uterine cavity, (c) the first and second orifice plugs then moving into contact with respective opposed walls of the uterine cavity and (d) the first and second orifice plugs applying pressure to respective opposed walls of the uterine cavity and riding up the opposed walls of the uterine cavity directing the first and second orifice plugs to respective orifices of fallopian tubes until the first and second orifice plugs seat at the respective orifices of the fallopian tubes or within the fallopian tubes.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 7A to 7D are detailed views showing the delivery apparatus for use in accordance with a preferred embodiment of the present invention with the steps of forcing the intrauterine occlusion device from within a container via a delivery rod.

FIGS. 8 to 13 are various views showing retrieval of the intrauterine occlusion device shown with reference to FIG. 1, while

FIGS. 26-30 show alternate embodiments employing a substantially straight elongated member.

FIGS. 48, 49, 50, 51, 52, 53, 54, 55 and 56 are schematic views of alternate embodiments of an orifice plug and/or elongated member structure in accordance with the present invention.

DESCRIPTION OF THE PREFERRED EMBODIMENTS

Figure 1:
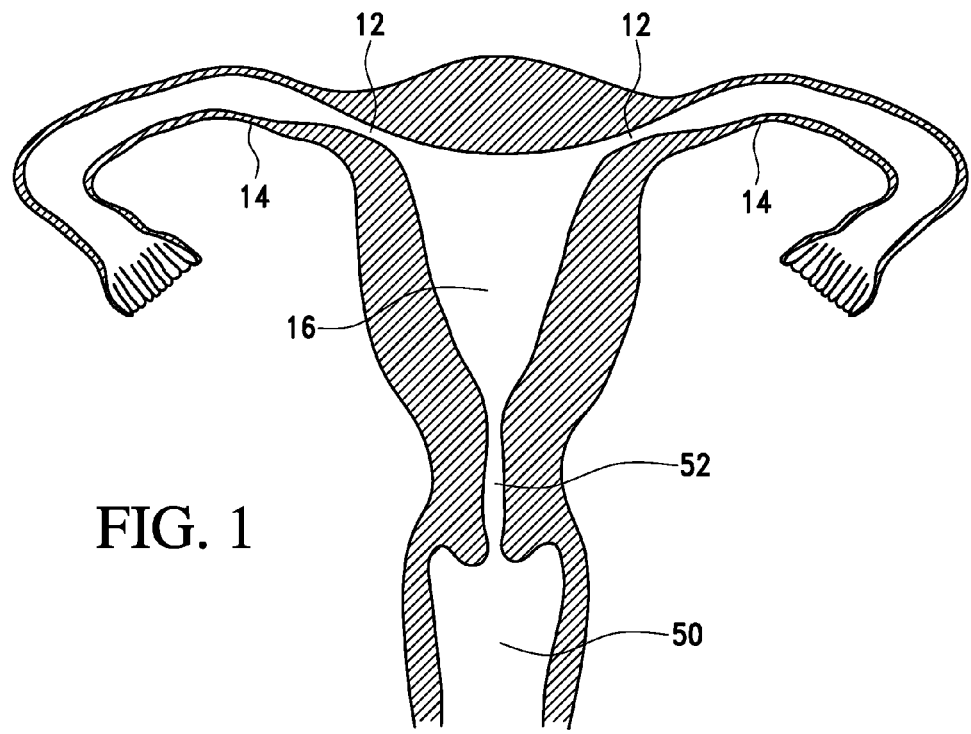
FIGS. 1 to 6 are various views showing delivery of the intrauterine occlusion device in accordance with a preferred embodiment of the present invention.
Figure 2:
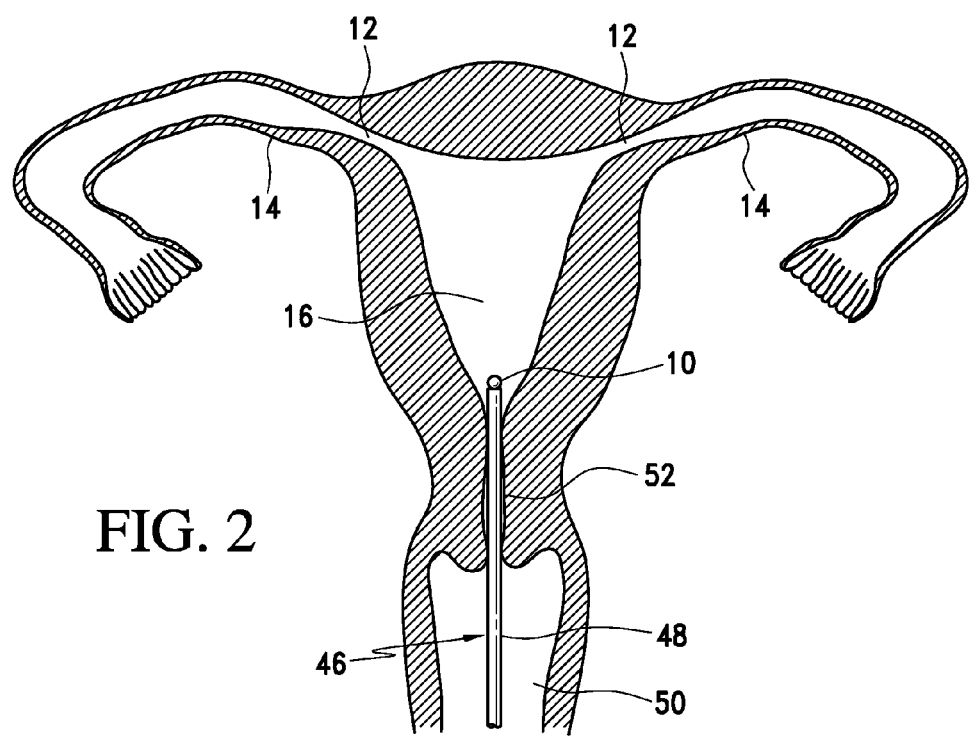
Figure 3:
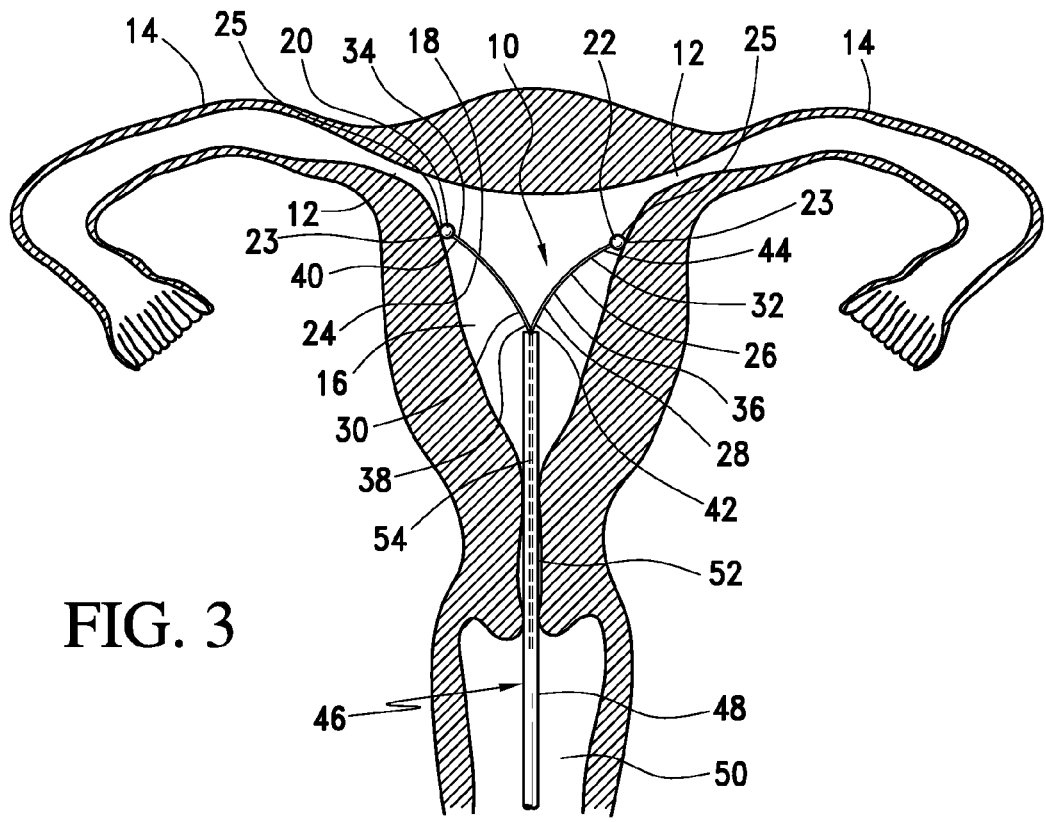
Figure 4:
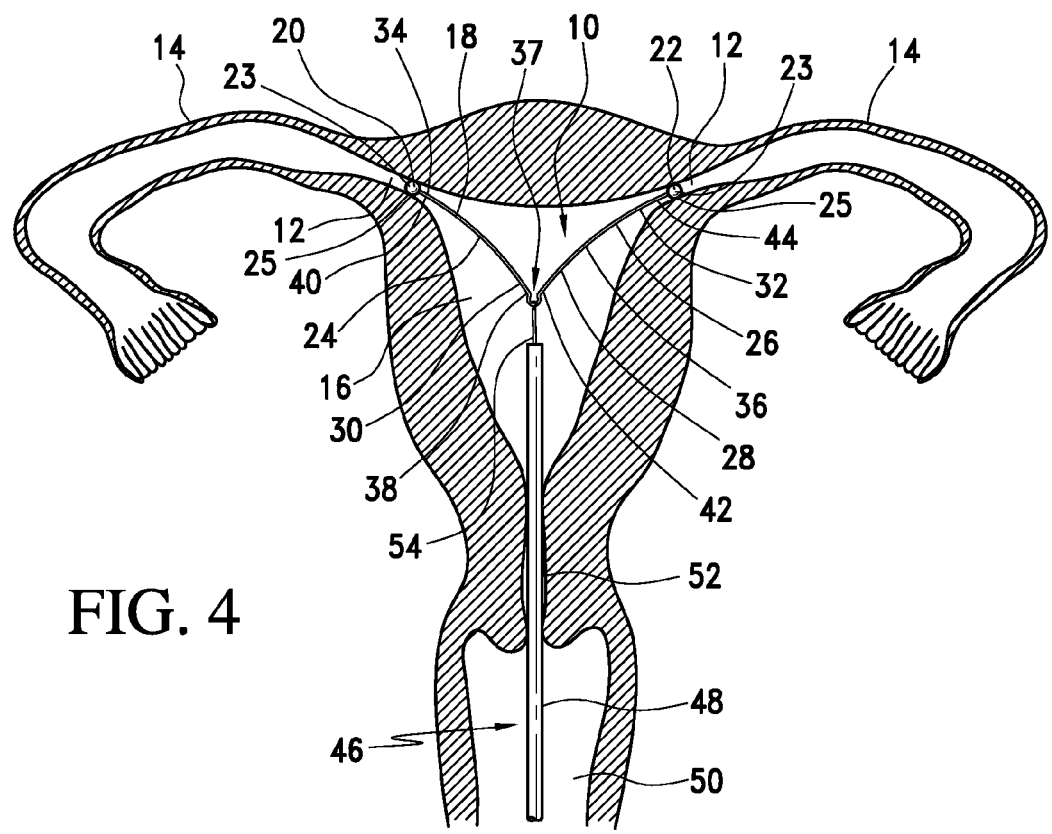
Figure 5:
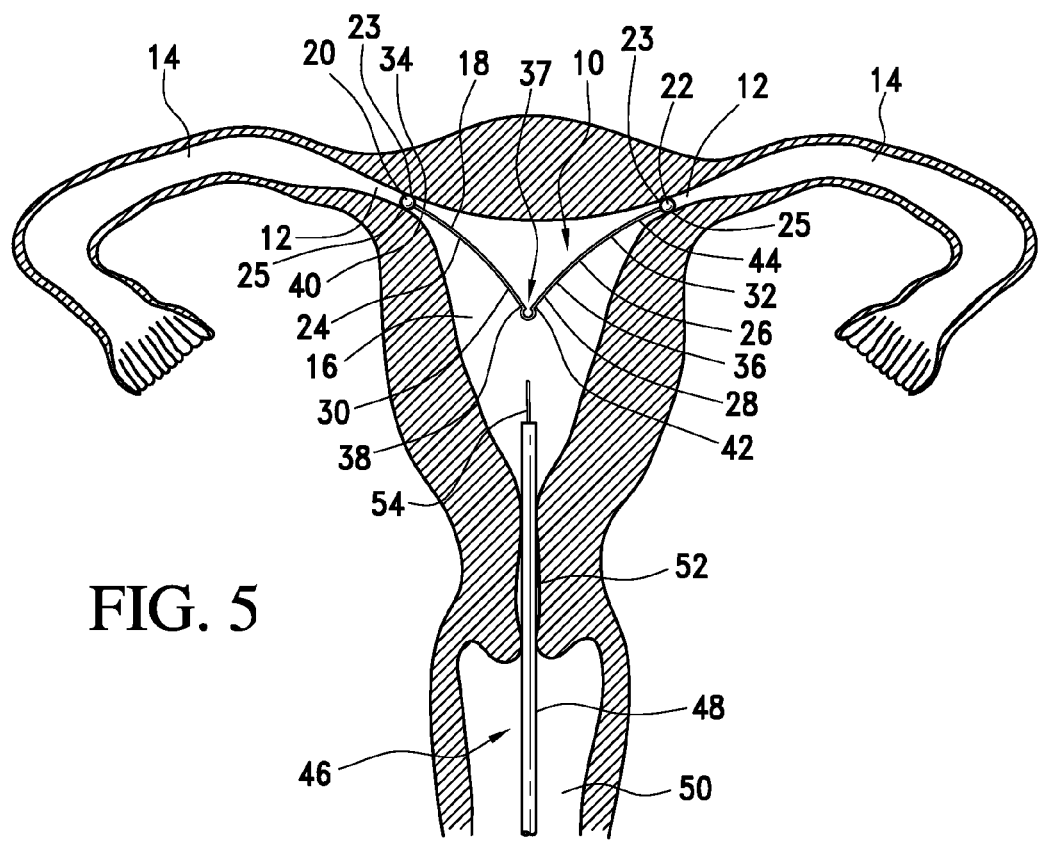

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention. Since various embodiments are disclosed herein, similar reference numerals have been employed throughout the present disclosure when referring to similar elements in the various embodiments and where such use of similar reference numerals is deemed appropriate.

With reference to the various figures, an intrauterine occlusion device 10 in accordance with a preferred embodiment of the present invention is disclosed that will actively occlude the orifices 12 of the fallopian tubes 14 using the shape of the uterine cavity 16 as a guide to the proper positioning of the intrauterine occlusion device 10. The shape of the uterine cavity 16 is illustrated in FIG. 1. The uterine cavity 16 is normally in continuation with the fallopian tubes 14. For fertilization, the sperm migrates from the uterine cavity 16 into the fallopian tube 14. Occlusion of the fallopian tube 14 prevents fertilization by preventing migration of the sperm into the fallopian tube 14.

The present invention provides an intrauterine occlusion device 10 that enables tubal occlusion, either permanent, removably permanent or temporary, in part or wholly, utilizing the unique shape of the uterine cavity 16. This intrauterine occlusion device 10 has the potential for a reduced rate of tubal pregnancies and, therefore, may be used by a larger patient population, including those that are adamantly opposed to abortion. The present invention also allows non-surgical tubal occlusion that can be done as an office procedure and without the need for surgery or the necessity for visualization of the fallopian tube orifices either radiologically, ultrasonically, or with a hysteroscope. The present invention also provides a treatment option for women that suffer from endometriosis, an often debilitating disease that commonly affects younger women. The present intrauterine occlusion device 10 uses radial force and inherent properties in its construction to prevent migration or expulsion of the intrauterine occlusion device 10. As such, the present invention may be used with the following procedures: contraception, either permanent or temporary; treatment of endometriosis; and potentially treatment of other causes of abnormal uterine bleeding or pelvic pain. The present intrauterine occlusion device 10 may be adaptable to other therapies or treatments, such as localized medicinal delivery, with only an alteration to the barrier system.

As briefly discussed above, the present invention provides a method and apparatus for the occlusion of the fallopian tubes wherein two occluding members (for example, orifice plugs as discussed herein) are retained in place by spreading them as far apart as the anatomy of the uterus permits and allowing the pressure generated as a result of spreading to be applied to the ostii of the fallopian tubes. For example, and as will be appreciated based upon the following disclosures, various structures may be employed in creating the necessary pressure. In accordance with various preferred embodiments described herein, the length between the orifice plugs is adjusted by flexation of the elongated member of the intrauterine occlusion device. As will be appreciated by the following disclosures, it is not necessary that the intrauterine occlusion device rely upon spring-like or resilient structures to achieve the creation of pressure but may employ other mechanical features as described herein.

In accordance with a preferred embodiment, the unique shape of the uterine cavity 16 allows the present intrauterine occlusion device 10 to be inserted without (or with) visualization into the uterine cavity 16 for positioning in a manner that occludes entry into the fallopian tubes 14. The unique shape also maintains the intrauterine occlusion device 10 in place without the need for sutures or any other anchoring mechanism. The present intrauterine occlusion device 10 is also readily removable and prevents migration of sperm into the fallopian tube 14, thereby preventing fertilization. The presence of the intrauterine occlusion device 10 in the uterine cavity 16 also redundantly acts as an IUD, but the occlusion effects prevent fertilization and thereby avert the destruction of an embryo, which is considered the major mechanism of an IUD's birth control efficacy. This makes the present intrauterine occlusion device 10 more acceptable to some patients and allows its use in a larger part of the population.

As mentioned above, the present intrauterine occlusion device 10 functions primarily as an occluding structure for the orifices 12 of the fallopian tubes 14 and secondarily as an IUD. The present invention also relates to a method and apparatus for transvaginal implantation and removal of the intrauterine occlusion device 10.

As is discussed below in greater detail, the present intrauterine occlusion device 10 is composed of a resilient body 18 with first and second orifice plugs 20, 22 at the respective first and second ends 24, 26 of the resilient body 18. The resilient body 18 is preferably made from a shape memory alloy metal (such as, Nitinol) or any other material (or combination of materials) that will create an appropriate load providing an appropriate lateral force as the intrauterine occlusion device 10 is deployed within the uterine cavity 16. The outwardly directed lateral force generated by the resilient body 18 brings the first and second orifice plugs 20, 22 into contact with the walls of the uterine cavity 16 creating opposed force along the walls of the uterine cavity 16 and causing the intrauterine occlusion device 10 to ride up the walls of the uterine cavity 16 until the first and second orifice plugs 20, 22 seat within the orifices 12 of the respective fallopian tubes 14. It is also contemplated the resilient body could be made out of resorbable magnesium alloy wire or resorbable plastic.

Figure 16:
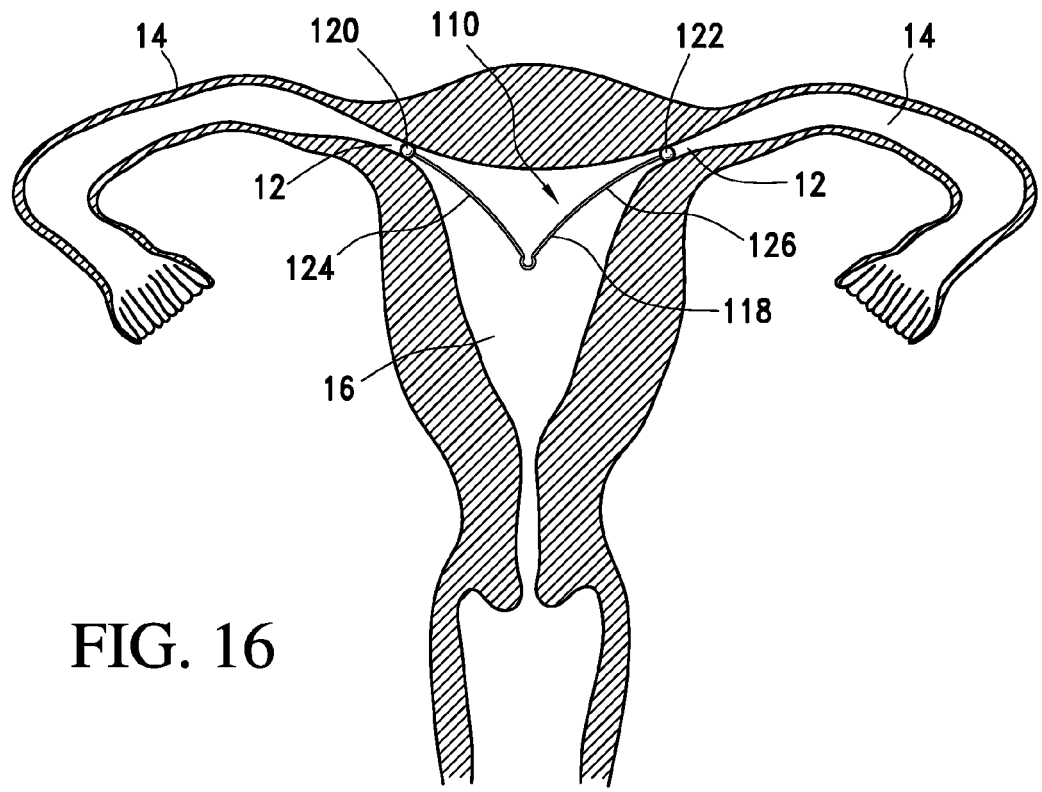
FIGS. 16, 17 and 18 are various views showing delivery of an alternate embodiment in which the orifice plugs are selectively detachable from the elongated member.
Figure 17:
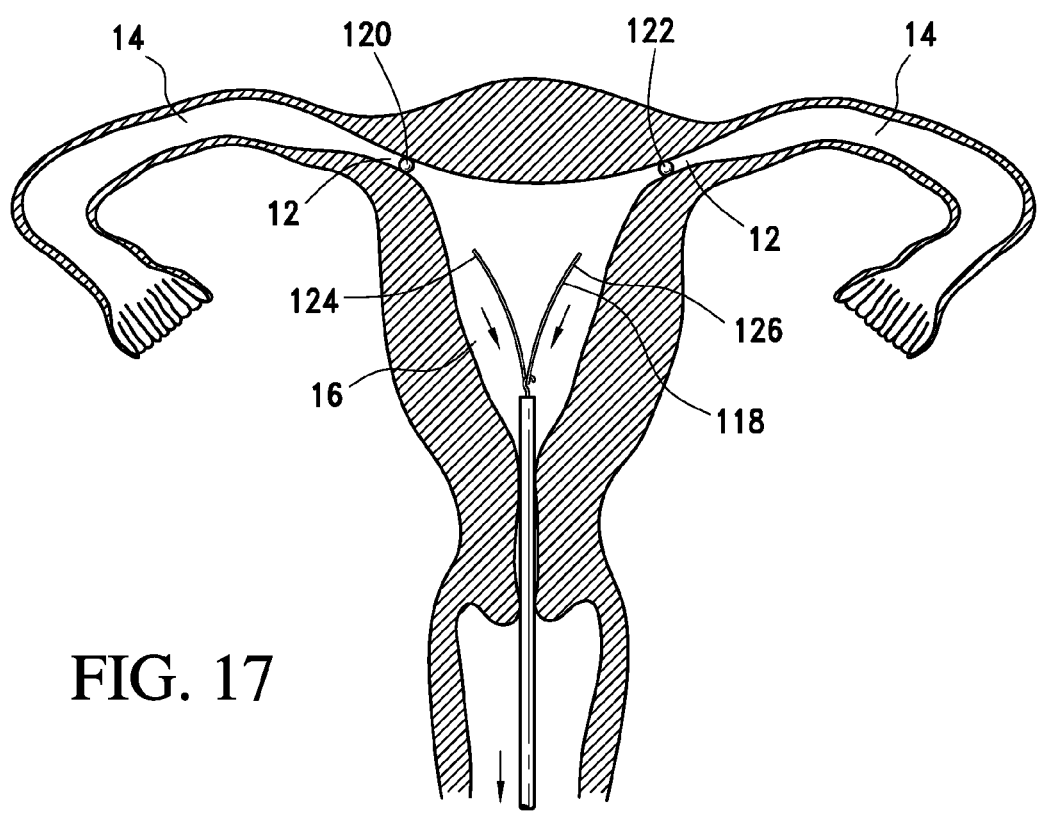
Figure 18:
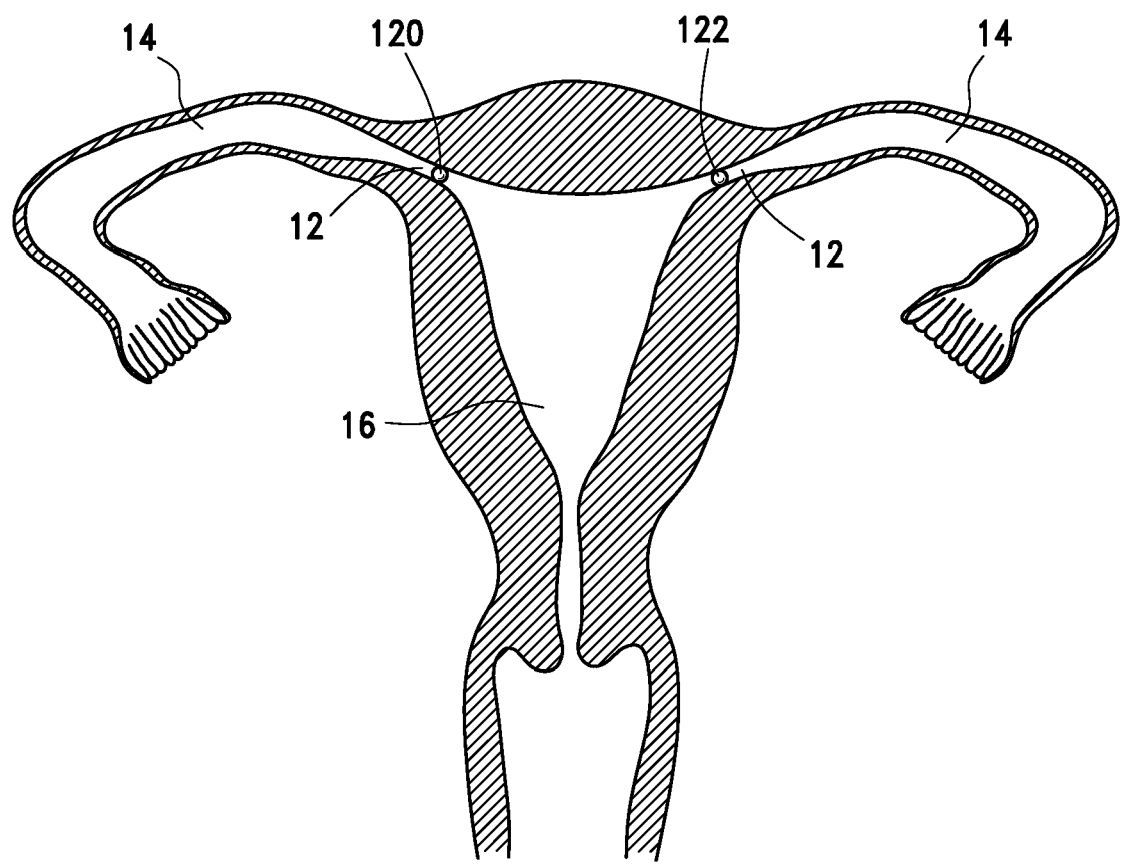

The orifice plugs 20, 22 for the fallopian tubes 14 can be made from various materials such as metals, plastics, elastomers such as silicone, or combinations thereof, and be impregnated with various medications and compounds. As will be appreciated based upon the following disclosure, it is further contemplated the material composition of the orifice plugs 20, 22 could be selected such that it would encourage tissue in-growth or prevent (or minimize) tissue in-growth, therefore controlling the ease of removal of the intrauterine occlusion device 10 after the passage of time. When tissue in-growth is desired, molded materials such as specially processed porous silicone, polyethylene, polypropylene, etc. could be used in the manufacture of the orifice plugs 20, 22 to allow tissue in-growth. In addition to generally molded constructions, the orifice plugs 20, 22 may take the form of a mesh or coil with or without a tissue in-growth member (for example, of a mesh material) for anchoring to surrounding tissue. The resilient body 18 and/or orifice plugs 20, 22 can be either inert, meaning without any medication or substance on them, or released from them, or they can be impregnated or coated, in part or wholly, with any medication such as hormones or metal, such as, copper. The orifice plugs 20, 22 can also be covered with any other kind of spermicide or other materials. As a result, the present intrauterine occlusion device 10 may be used as a medication delivery device, supplying medication to specific locations and then retrieved in part or wholly as discussed below with reference to FIGS. 8-13 or maintained in position as discussed below with reference to FIGS. 16, 17 and 18.

The present intrauterine occlusion device 10 can also serve as a delivery system for the orifice plugs 20, 22 or any occlusion or other devices to the orifices 12 of the fallopian tubes 14. The intrauterine occlusion device 10 utilizes the shape of the uterine cavity 16 and conforms the shape of the first and second orifice plugs 20, 22 to the orifices 12 of the fallopian tubes 14, and/or the orifice plugs 20, 22 elastically or deformably conform to the orifices 12 of the fallopian tubes 14. As briefly mentioned above, the orifice plugs 20, 22 can contain any kind of material or medicine to be delivered into the orifices 12 or the fallopian tubes 14. Once the material or medicine is delivered to the orifices 12 or the fallopian tubes 14, the intrauterine occlusion device 10 can be removed in the manner discussed below with reference to FIGS. 8 to 13, or the first and second orifice plugs 120, 122 may be selectively separated from the resilient body 118 and left in place within the orifices 12 of the fallopian tubes 14 as discussed below with reference to the embodiment disclosed with reference to FIGS. 16, 17 and 18.

Referring to the various figures, and in accordance with a preferred embodiment of the present invention, the present intrauterine occlusion device 10 includes a resilient body 18 exhibiting spring-like characteristics. The resilient body 18 has first and second orifice plugs 20, 22 secured at opposite ends thereof. In accordance with a preferred embodiment of the present invention, the first and second orifice plugs 20, 22 are shaped and dimensioned to ride up the walls of the uterine cavity 16 until they seat within the orifices 12 of the fallopian tubes 14, within the fallopian tubes 14 or partially within the orifices 12 of the fallopian tubes 14 and partially within the fallopian tubes 14 as the resilient body 18 spreads outwardly with the first end 24 and second end 26 thereof moving apart. Optimal seating has been found to be achieved when the orifice plugs 20, 22 have a diameter from approximately 1 mm to 8 mm.

More particularly, the resilient body 18 includes an elongated member 28 having a first end 30 and a second end 32. The first end 30 of the elongated member 28 is composed of a first leg 34 and the second end 32 of the elongated member 28 is composed of a second leg 36. The first orifice plug 20 is secured at the distal end of the first end 30 of the elongated member 28 and the second orifice plug 22 is secured at a distal end of the second end 32 of the elongated member 28.

The first leg 34 includes a first end 38 and second end 40, and the second leg 36 includes a first end 42 and second end 44. The first ends 38, 42 of the respective first and second legs 34, 36 are respectively connected, while the second ends 40, 44 of the first and second legs 34, 36 are respectively free and are provided with, and coupled to, the respective first and second orifice plugs 20, 22. A connection member 37 resiliently (or rigidly) couples the first ends 38, 42 of the first and second legs 34, 36 in a manner biasing the second ends 40, 44 of the first and second legs 34, 36 from each other when they are not restrained in a manner discussed below in greater detail.

With this in mind, the first leg 34 and the second leg 36 are angularly oriented relative to each other creating an elongated member 28 which is substantially V-shaped when the first leg 34 and the second leg 36 are allowed to move away from each other based upon the outward bias inherent in the connection member 37 between the first and second legs 34, 36. The inherent bias in the connection member 37 is created through the utilization of spring materials or shape memory materials in the construction of the resilient body 18, in particular, the connection member 37. With this in mind, the connection member 37 includes a substantially circular configuration with a first end 37a connected to the first end 38 of the first leg 34 and a second end 37b connected to the first end 42 of the second leg 36 (see FIGS. 7C and 7D). The connection member 37 is formed with an inherent outward bias that forces the first leg 34 and the second leg 36 outwardly upon deployment.

In addition, and in accordance with a preferred embodiment, the first leg 34 and the second leg 36 are formed with an outward bow when fully extended. This outward bow can store further outward bias when the intrauterine occlusion device 10 is compressed for storage and deployment. In accordance with a preferred embodiment, when the intrauterine occlusion device 10 is entirely unrestrained the first and second legs 34, 36 will form a maximum open angle of approximately 150 degrees or other appropriate angular dimension so as to adequately contribute to the aforementioned outward bias. This angle forms a geometry preventing the first and second legs 34, 36 from moving away from a fundamentally centralized location in the uterine cavity 16 (see FIGS. 1 to 6). That is, the shape of the resilient body 18, a sort of triangle, only spreads so wide so that it would bump into the walls of the uterine cavity 16, that way staying located in the center of the uterine cavity 16.

The combination of the outwardly bowed first and second legs 34, 36 and the connection member 37 allow for the creation of an outwardly directed load providing an appropriate lateral force to bring the first and second orifice plugs 20, 22 into contact with the walls of the uterine cavity 16 causing the intrauterine occlusion device 10 to ride up the walls of the uterine cavity 16 until the first and second orifice plugs 20, 22 seat within the orifices 12 of the respective fallopian tubes 14. As such, and as discussed herein in greater detail, the present intrauterine occlusion device 10 may be delivered by release within the uterine cavity 16 with automatic expansion resulting in controlled, self-positioning of the respective orifice plugs 20, 22 at the orifices 12 of the fallopian tubes 14

Figure 14:
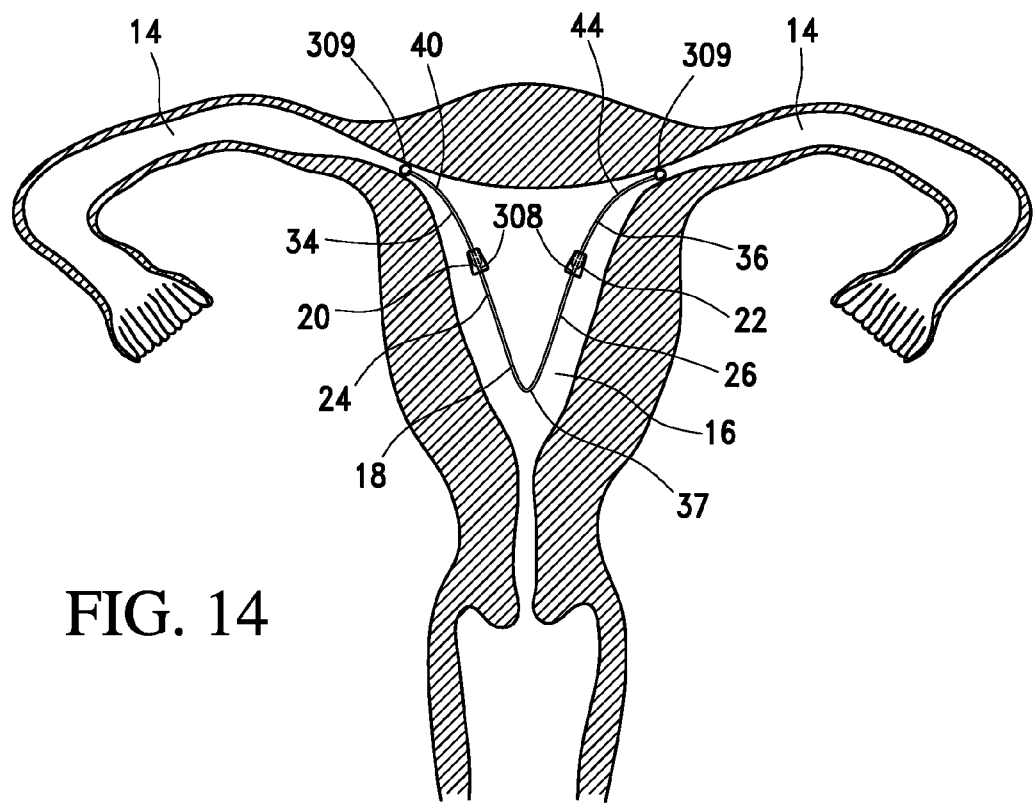
FIGS. 14 and 15 are schematics showing an alternate embodiment of the intrauterine occlusion device wherein the orifice plugs ride on the first and second legs for sliding movement of the orifice plugs relative to the respective first and second legs.
Figure 15:
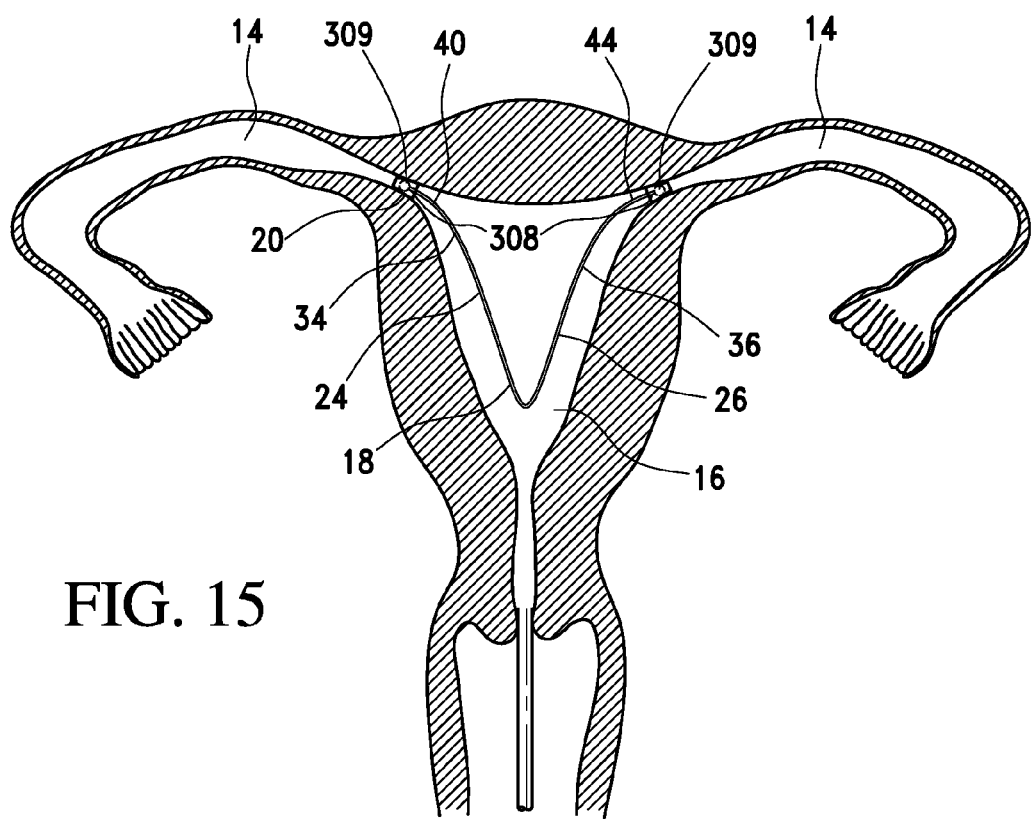

Referring to FIGS. 14 and 15, an alternate embodiment in accordance with the present invention is disclosed. In accordance with this embodiment, the orifice plugs 20, 22 are designed to slide along the resilient body 18. In particular, the resilient body 18 is once again made from a shape memory alloy metal, or other appropriate resilient material, and is formed in the shape of a V such that the first and second ends 24, 26 of the resilient body 18 are directed toward the fallopian tubes 14 when properly inserted within the uterine cavity 16. However, upon insertion, the orifice plugs 20, 22 are located at a first position adjacent the connection member 37 linking the first and second legs 34, 36 (see FIG. 14). Once the resilient body 18 is positioned within the uterine cavity 16 with the second ends 40, 44 of the respective first and second legs 34, 36, that is, the first and second ends 24, 26 of the resilient body 18, positioned within the fallopian tubes 14, the orifice plugs 20, 22 are respectively moved upwardly along the first and second legs 34, 36 to a second position adjacent the second ends 40, 44 of the respective first and second legs 34, 36 where the orifice plugs 20, 22 are positioned within the fallopian tubes 14. With this in mind, each of the first and second orifice plugs 20, 22 is formed with a central bearing aperture 308 through which the resilient body 18 passes during usage. Retention of the orifice plugs 20, 22 at the second ends 40, 44 of the first and second legs 34, 36 is achieved by frictional retention due to the interaction between the central bearing apertures 308 and enlarged, spherical member 309 formed at the second ends 40, 44 of the respective first and second legs 34, 36.

Figure 21A:
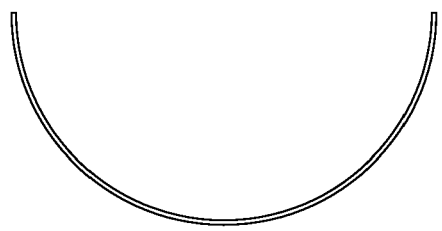
FIGS. 21A, 21B, 21C and 21D show various shapes of an elongated member that may be used in accordance with the present invention.
Figure 21B:
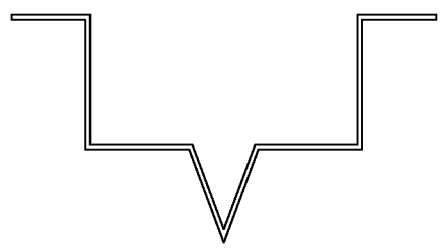
Figure 21C:
Figure 21D:
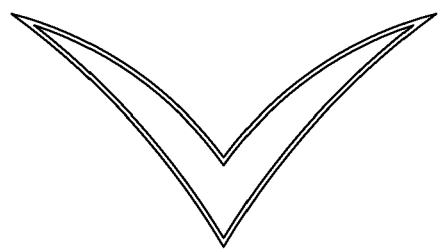

Although a preferred embodiment of the present invention employs a V-shaped elongated member with an outward bow as disclosed above, it is contemplated the elongated member 28 may be formed with a variety of shapes (whether in a fundamentally two dimensional planar configuration or a three dimensional planar configuration) so long as it retains its spring-like properties. Examples of contemplated shapes are shown in FIGS. 21A to 21D: FIG. 21A shows a U-shaped elongated member; FIG. 21B shows a stepped elongated member; FIG. 21C shows a crescent-shaped elongated member; and FIG. 21D shows a chevron-shaped elongated member.

Figure 22:
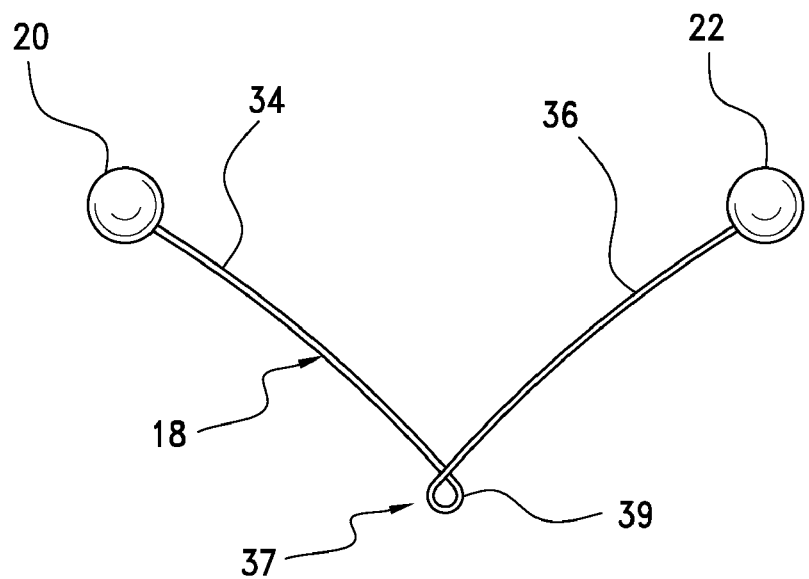
FIGS. 22, 23 and 24 show alternate embodiments of a connection member in accordance with the present invention.
Figure 23:
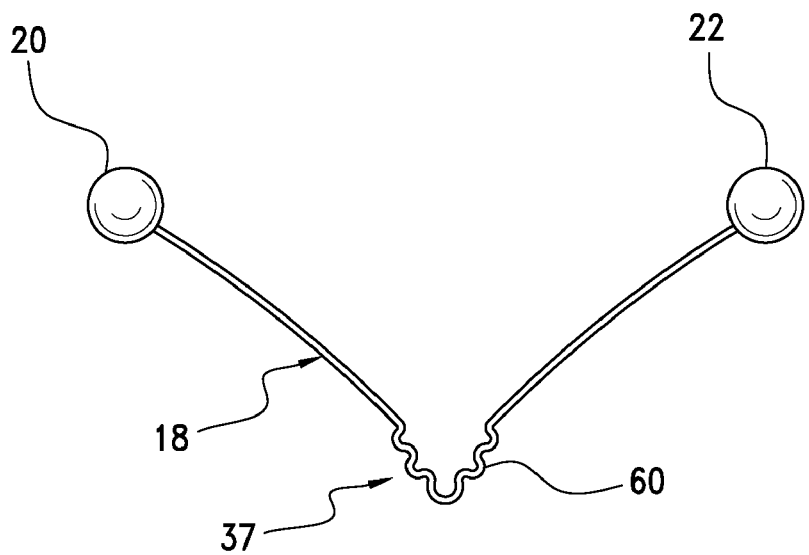

In addition, the spring bias may be imparted to the first leg 34 and the second leg 36 by constructing the connection member 37 with a spring biased loop 39 as shown in FIG. 22 or the spring bias may be controlled by incorporating bends 60 in the connection member 37 as shown in FIG. 23.

Figure 24:
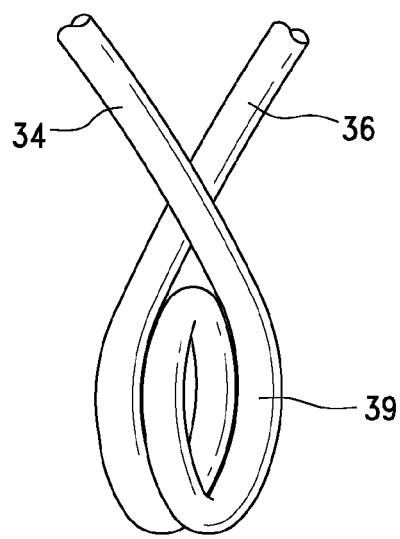
Figure 25A:
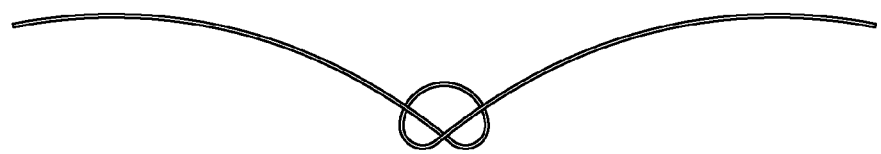
FIGS. 25A-K show other connection member structures in accordance with the present invention.
Figure 25B:
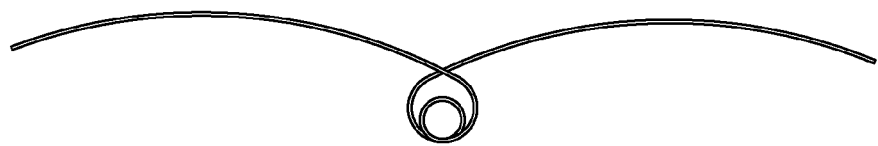
Figure 25C:
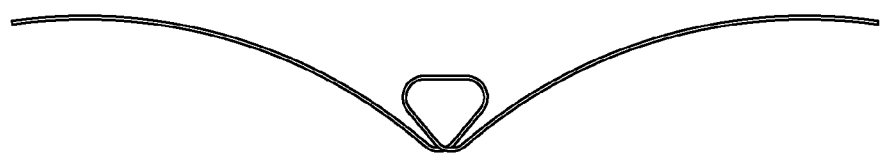
Figure 25D:
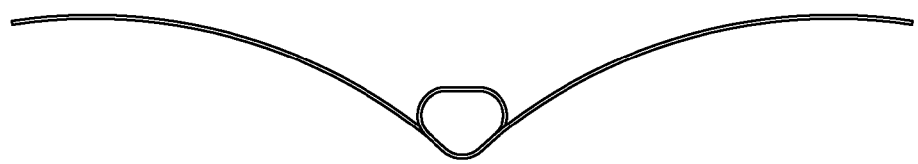
Figure 25E:
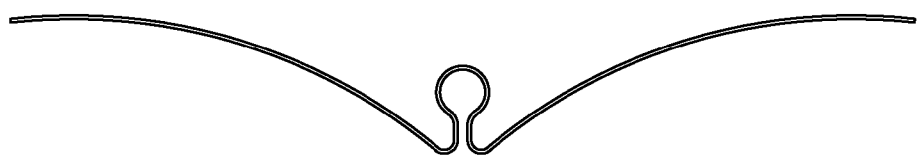
Figure 25F:
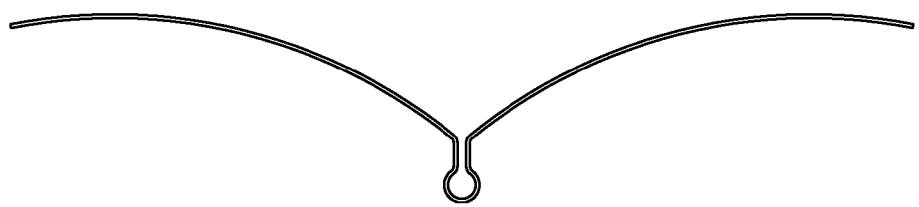
Figure 25G:
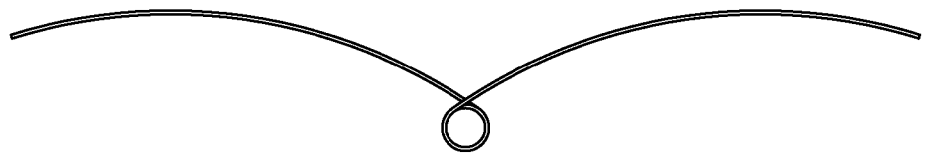
Figure 25H:
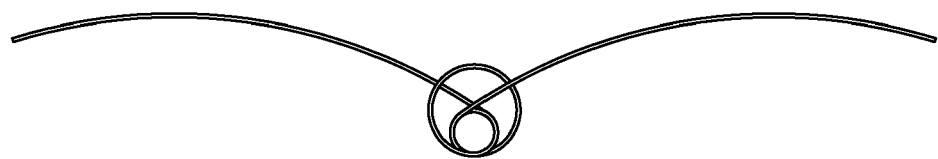
Figure 25I:
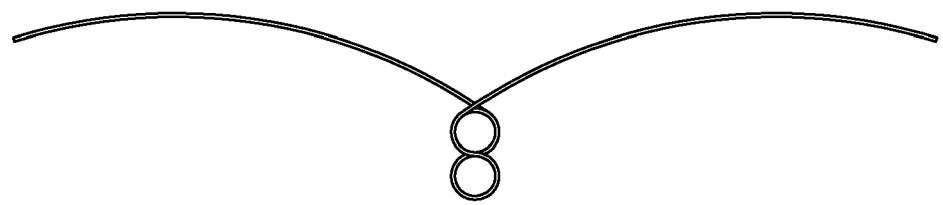
Figure 25:
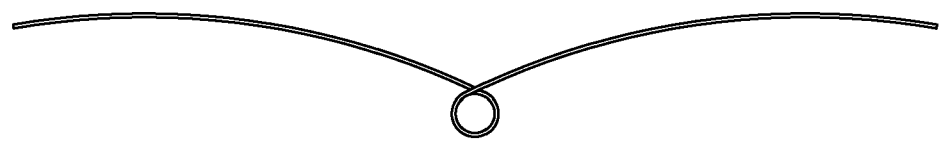
Figure 25K:
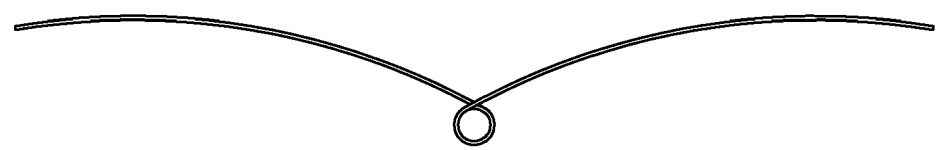

In accordance with yet another embodiment and as shown in FIG. 24, a biased loop 39 composed of multiple windings may also be employed. Similarly, and with reference to FIGS. 25A-25K, the biased loops 39 may take a variety of configurations designed to achieve a desired bias along the length of the first and second legs 34, 36. Ultimately, the bias of the connection member may be varied to suit the specific needs of the user.

Considering the various shapes that may be employed in accordance with a preferred embodiment of the present invention, it is contemplated the outward bias of the first and second legs may be achieved by creating resilience along the length of the first and second legs rather than at the connection point of the first and second legs. For example, where the first and second legs are formed of Nitinol, the first and second legs may be formed such that they bow outwardly when exposed to elevated activation temperature upon placement within the body.

With regard to the material construction of the elongated member 28, and further to the earlier disclosure, it is preferably composed of resilient, biocompatible materials (metal, polymer or composite) or shape memory or super-elastic materials (for example, Nitinol), other alloys, or combinations thereof, capable of offering the biasing characteristics discussed herein and required for proper operation of the present invention. If a material desired for use is not biocompatible, it could be covered by another biocompatible material, for example, a coating or a thin-walled plastic tube.

Further to the various shapes in which the elongated member 28 may be formed as disclosed above, other shapes are shown with reference to FIGS. 26 to 30. In accordance with these various embodiments, the elongated member 28 could be normally straight when unbiased and positioned within the uterine cavity 16. In accordance with this embodiment, the elongated member 28 would be forcibly folded inside the delivery container 48 (as discussed below in greater detail). The elongated member 28 is folded in this configuration until such a time that it is introduced within the uterine cavity 16 and released for positioning between the opposed fallopian tubes 14. Upon deployment, the elongated member 28 extends to a substantially straight configuration (for example, with an angular relationship of between 170° to 190°) with the orifice plugs 20, 22 positioned within the fallopian tubes 14.

Referring to FIGS. 26 and 28-30, the elongated member 28 could be formed with a U-shaped connection member 37. The connection member 37 is shaped and dimensioned for facilitating the folding and positioning of the elongated member 28 within the delivery container 48 for subsequent expansion thereof when the elongated member 28 is released during application within the uterine cavity 16. The connection member 37 also allows for control of the resilience imparted to the elongated member 28 in accordance with desired parameters. FIG. 27 shows an embodiment wherein the connection member 37 is continuous with the elongated member.

Figure 31A:
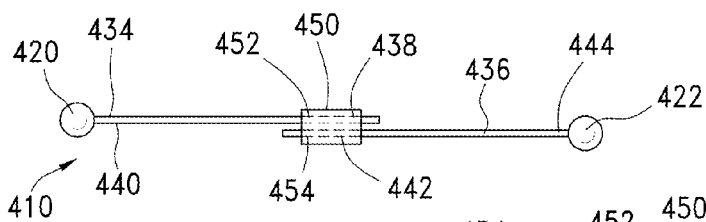
FIGS. 31A, 31B and 31C show an alternate structure for an intrauterine occlusion device in accordance with the present invention.
Figure 31B:
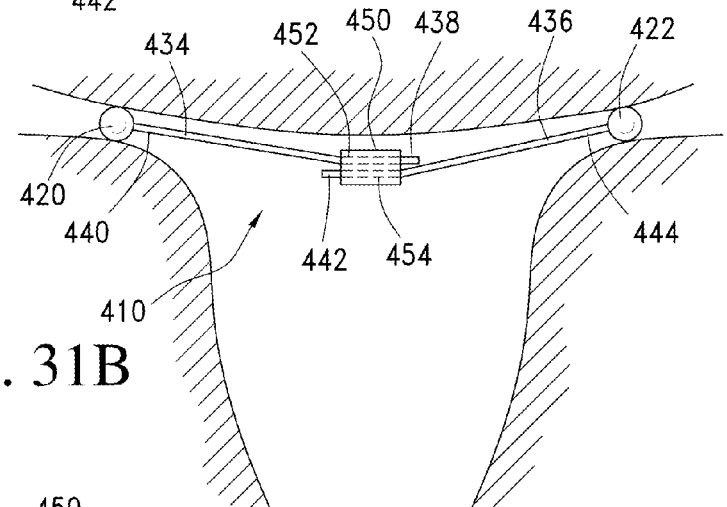

As discussed above, other mechanical mechanisms for the application of the orifice plugs within the fallopian tubes are contemplated. For example, mechanical force generating structures may be employed within the spirit of the invention. With this in mind, and with reference to FIGS. 31A, 31B and 31C, the intrauterine occlusion device 410 includes an elongated member 428 composed of first and second legs 434, 436 connected to each other for controlled relative movement by a clamping member 450. More particularly, the occlusion device 410 is composed of first and second legs 434, 436, each of the first and second legs 434, 436 includes a first end 438, 442 and a second end 440, 444 wherein an orifice plug 420, 422 is secured to the respective second ends 440, 444 of the first and second legs 434, 436 and the respective first ends 438, 442 are secured via the clamping member 450.

The clamping member 450 is a generally elongated member including first and second apertures 452, 454 shaped and dimensioned for receiving the respective first ends 438, 442 of the first and second legs 434, 436. Until the clamping member 450 is crimped to lock the first and second legs 434, 436 in position relative to the clamping member 450 (as will be discussed below in greater detail), the apertures 452, 454 are formed to permit relative movement of the first and second legs 434, 436, and ultimately, the first and second orifice plugs 420, 422, as the first and second legs 434, 436 are moved within the clamping member 450. As will be appreciated based upon the figures, the first and second legs 434, 436 are formed from slightly flexible materials allowing for bending thereof so as to conform to the anatomical distinctiveness of each individual patient.

Figure 31C:
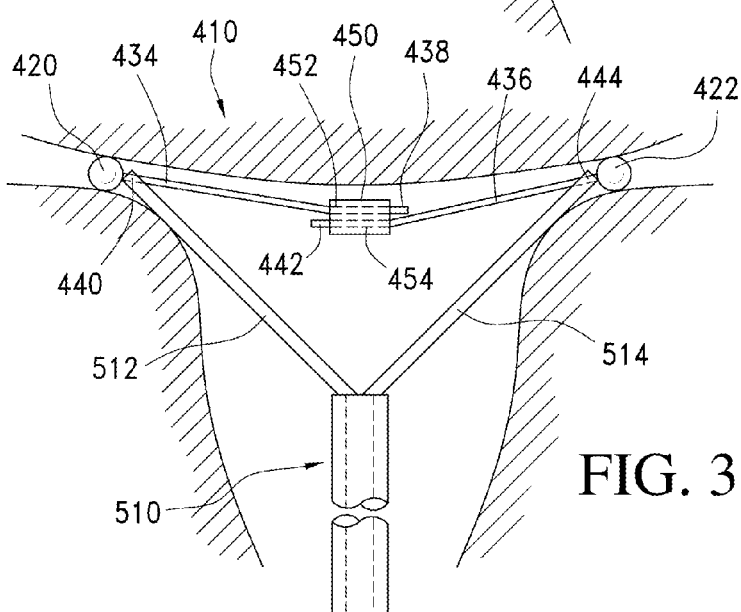

In accordance with a preferred embodiment, deployment of the intrauterine occlusion device 410 is facilitated through the utilization of a deployment assembly 510 as shown with reference to FIG. 31C. The deployment assembly 510 includes first and second members 512, 514 which are resiliently biased outwardly to engage and force the orifice plugs 420, 422 into the fallopian tubes 14. The deployment assembly 510 is further provided with a force gauge 516 for measuring the applied pressure as the orifice plugs 420, 422 are forced on the ostii. Alternatively, the deployment assembly could be equipped with a force indicator such as a colored slide that moves to another position when appropriate pressure is achieved.

In practice, the intrauterine occlusion device 410 is delivered to the uterine cavity 16 and roughly positioned such that the first and second orifice plugs 420, 422 sit adjacent to the orifices 12 of the fallopian tubes 14. The deployment assembly 510 is then employed to push the first and second orifice plugs 420, 422 within the orifices 12 of the fallopian tubes 14. When a desired application pressure is achieved, the clamp member 450 is crimped in a manner securing it to the first ends 438, 442 of the respective first and second legs 434, 436 thereby locking the first and second legs 434, 436 in position relative to each other. Crimping of the clamping member 450 is achieved through utilization of medical grade forceps shaped and dimensioned to access the uterine cavity 16 and engage the clamping member 450.

Figure 32:
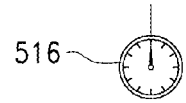
FIG. 32 shows yet another structure for an intrauterine occlusion device in accordance with the present invention.

In accordance with another embodiment as shown with reference to FIG. 32, an elongated member 428 composed of first and second legs 434, 436 is similarly provided. The first and second legs 434, 436 respectively include first and second orifice plugs 420, 422 secured to the second ends 440, 444 thereof. The first ends of the first and second legs 434, 436 are structured for a telescopic mating relationship. In particular, the first end 438 of the first leg 434 includes a central threaded passageway 460 shaped and dimensioned for receiving the first end 442 of the second leg 436 in a threaded mating configuration. With this in mind, the internal cavity of the central threaded passageway 460 of the first leg 434 includes threading 462 shaped and dimensioned to mate and engage threading 464 formed along the external surface of the second leg 436. As such, rotation of the first and second legs 434, 436 relative to each other alters the effective length of the intrauterine occlusion device 410 by moving the first and second orifice plugs 420, 422 further apart.

In practice, the intrauterine occlusion device 410 is delivered to the uterine cavity 16 and roughly positioned such that the first and second orifice plugs 420, 422 sit adjacent to the orifices 12 of the fallopian tubes 14. The first and second legs 434, 436 are then engaged and rotated, pushing the first and second orifice plugs 420, 422 within the orifices 12 of the fallopian tubes 14. When a desired application pressure is achieved, rotation is terminated thereby locking the first and second legs 434, 436 in position relative to each other with the orifice plugs 420, 422 positioned within the orifices 12 of the fallopian tubes 14.

Figure 33:
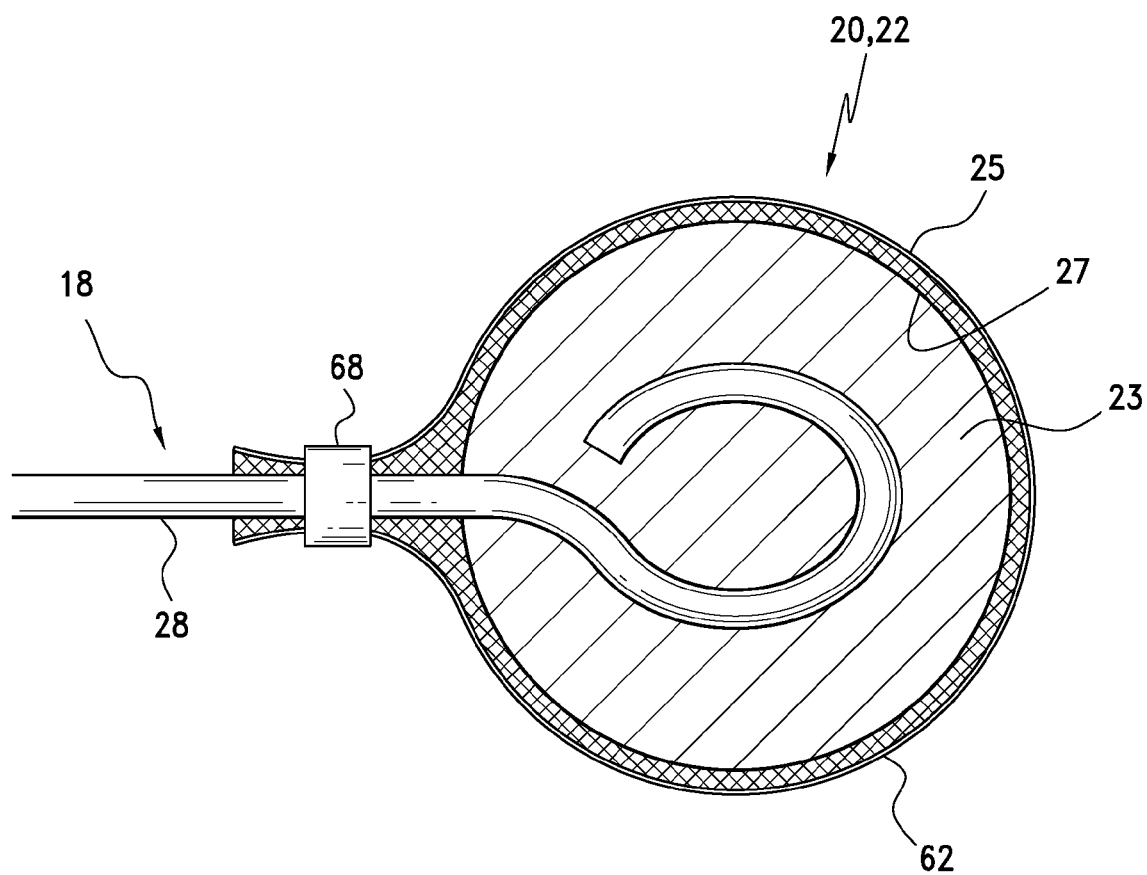
FIG. 33 is a cross sectional view of an orifice plug in accordance with a preferred embodiment of the present invention.

As shown with reference to FIGS. 3-6, 7A-D and 8-11, and in accordance with a preferred embodiment, the orifice plugs 20, 22 are spherical. In accordance with a preferred embodiment, the orifice plug body 23 of the orifice plug 20, 22 is made of silicone or porous, high density polyethylene exhibiting structure permitting tissue in-growth. Depending upon whether it is desired to provide a retrievable orifice plug 20, 22 or a permanently anchored orifice plug 20, 22, the outer surface 25 of the orifice plug 20, 22 will either be the silicone from which it is made (in which case the orifice plug body 23 forms substantially all of the orifice plug 20, 22 as shown in FIGS. 3-6, 7A-D and 8-11), be composed of a tissue in-growth member 62, for example, porous, high density polyethylene, which is secured about the outer surface 27 of the silicone orifice plug body (or substrate) 23 (see FIG. 33 which is discussed below in greater detail), or be composed of a foamed silicone with interstitial voids.

Where a permanent anchoring of the orifice plug 20 within the fallopian tube is desired, and with reference to an embodiment of the present invention as disclosed with reference to FIG. 33, a tissue in-growth member 62 is positioned over the silicone substrate material making up the orifice plug body 23 so as to provide the orifice plug 20, 22 with an outer tissue in-growth surface 27. Although reference numeral 20 is used in describing the orifice plug it will be understood the first and second orifice plugs 20, 22 are identical and/or symmetric. However, it is contemplated it may be advantageous to provide for an asymmetric construction with the first and second plugs differing in construction.

The tissue in-growth member 62 is constructed of a material promoting and maintaining tissue in-growth for the purpose of anchoring the orifice plug 20 and/or creating a seal. It is contemplated the tissue in-growth member 62 could be a biocompatible fabric (for example, a polyester fabric), textile, felt or membrane known by those skilled in the art to encourage tissue in-growth. In accordance with a preferred embodiment of the present invention, it is contemplated the tissue in-growth member 62 may be a knitted polymer textile with appropriate tissue in-growth properties to be considered an acceptable option for use in conjunction with the present invention. The tissue in-growth member could further be covered with a specialty coating that enhances and/or accelerates tissue in-growth.

Figure 34:
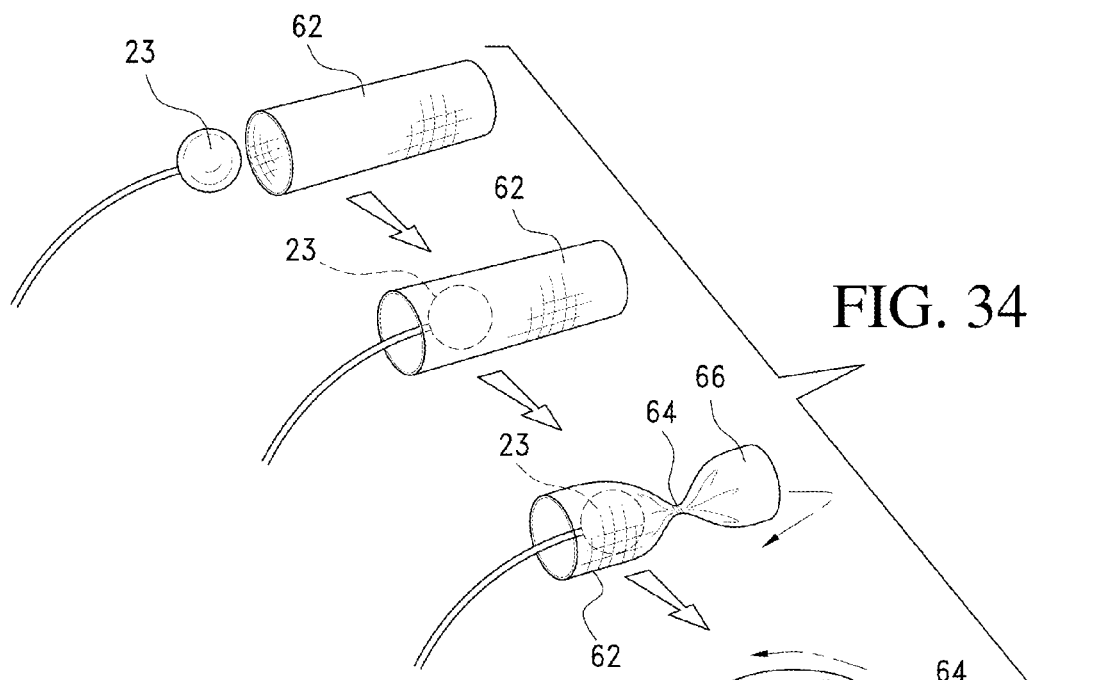
FIGS. 34, 35, 36 and 37 show the steps associated with various techniques for the application of a tissue in-growth member to the orifice plug.

The tissue in-growth member 62, which is also referred to as a "fabric sock" in accordance with the embodiments described below, may be secured to the orifice plug body 23 through the implementation of various techniques. For example, and with reference to FIG. 34, a cylindrical fabric sock 62 with open ends is placed over the orifice plug body 23 and the fabric sock 62 is twisted so as to create a reduced diameter by twisting or knotting, section 64 distal of the orifice plug body 23. Thereafter, the distal portion 66 of the fabric sock 62 is pulled proximally and over the reduced diameter twisted section 64 and the orifice plug body 23. A band 68 is then applied to the fabric sock 62 proximally of the orifice plug body 23 to secure it in position about the orifice plug body 23.

Figure 35:
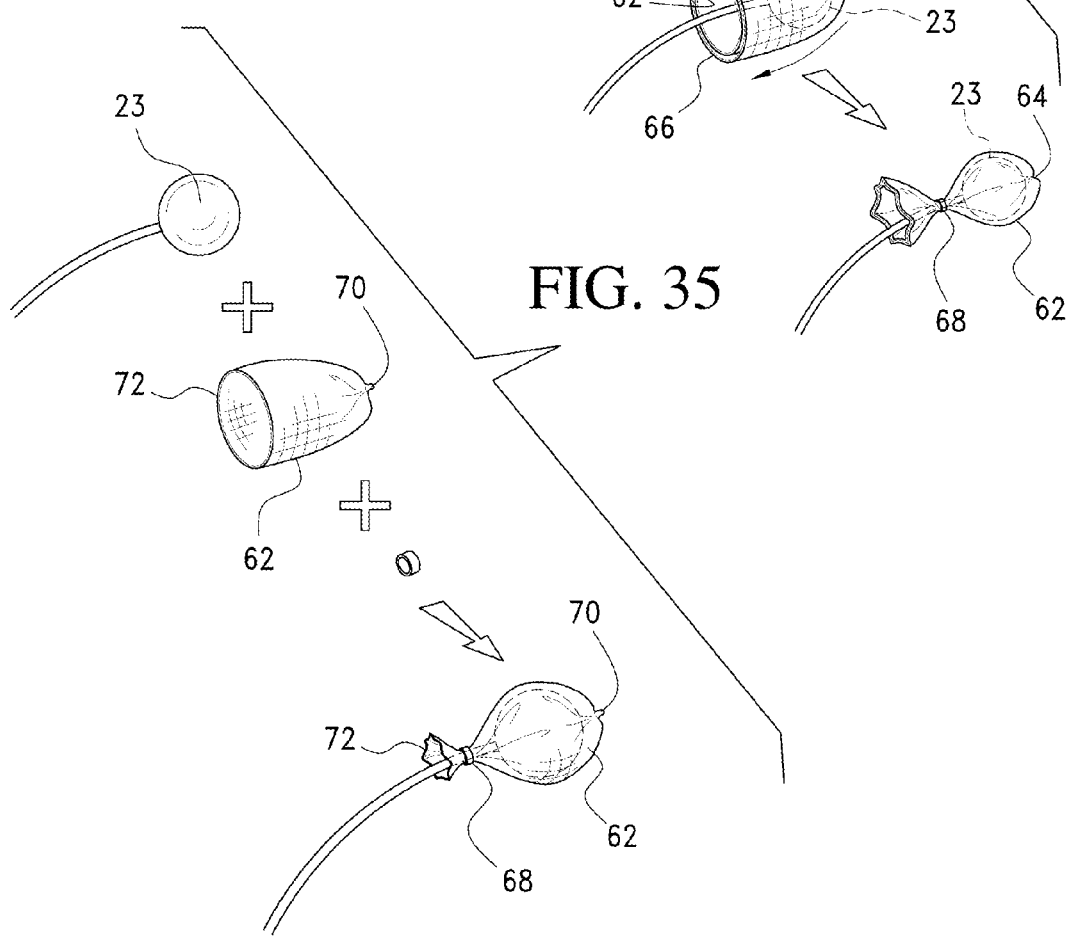

In accordance with an alternate embodiment, and with reference to FIG. 35, a fabric sock 62 with a closed distal end 70 is pulled over the orifice plug body 23. The closed distal end 70 is preferably formed through the application of heat to close the distal end 70 of the fabric sock 62. Once the fabric sock 62 is pulled over the orifice plug body 23 with the closed distal end 70 of the fabric sock 62 covering the distal end of the orifice plug body 23, the proximal end 72 of the fabric sock 62 is closed via the application of a band 68 proximally of the orifice plug body 23 to secure it in position about the orifice plug body 23.

Figure 36:
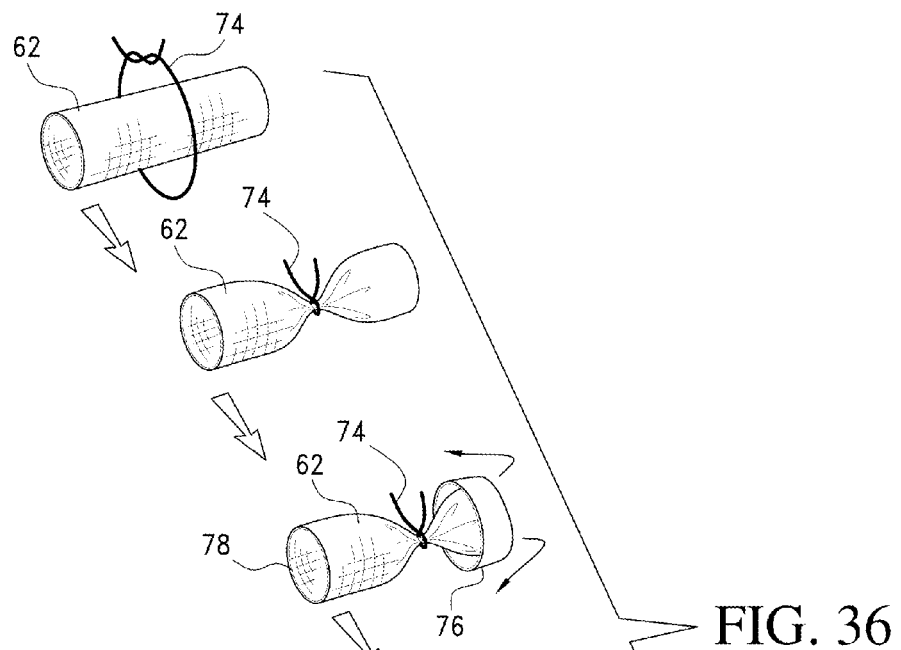
Figure 37:
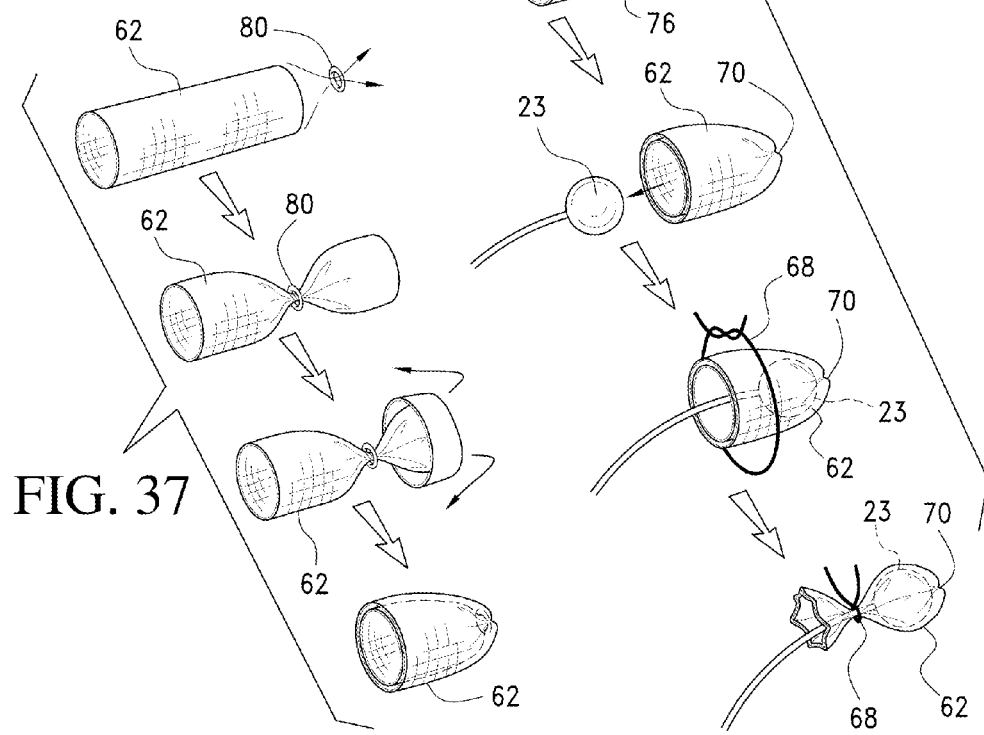

In accordance with yet another embodiment, and with reference to FIG. 36, a cylindrical fabric sock 62 with open ends may be formed into a double layered, closed ended fabric sock 62 by tying the center 74 of the cylindrical fabric sock 62 and pulling one end 76 thereof over the other end 78 resulting in a fabric sock 62 with a closed distal end 70. Thereafter, the fabric sock 62 is pulled over the orifice plug body 23 with the closed distal end 70 of the fabric sock 62 covering the distal end of the orifice plug body 23, the proximal end of the fabric sock 62 is closed via the application of a band 68 proximally of the orifice plug body 23 to secure it in position about the orifice plug body 23. The embodiment disclosed above with reference to FIG. 37 may be varied by utilizing a washer 80 to constrict the center of the cylindrical fabric sock 62 as opposed to the tie disclosed above.

Figure 38:
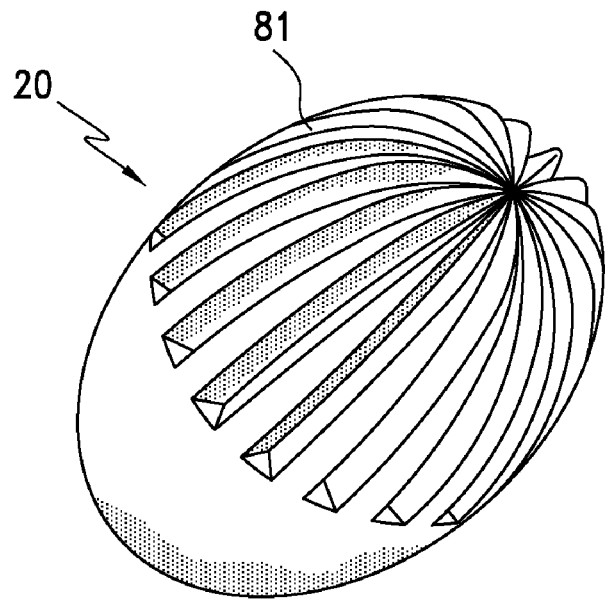
FIGS. 38 and 39 show orifice plugs specifically designed for encouraging tissue in-growth.
Figure 39:
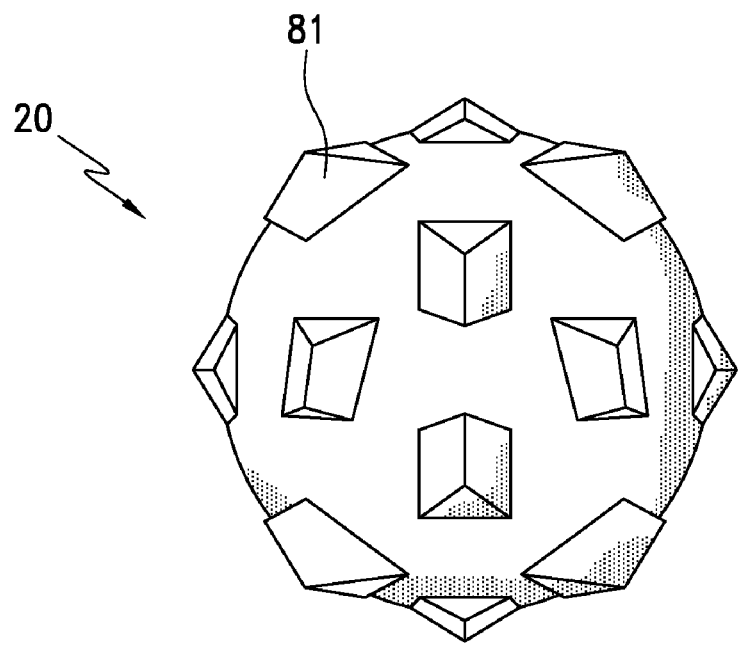

With reference to FIGS. 38 and 39, orifice plugs with various in-growth promoting construction are disclosed. In accordance with FIG. 38, the orifice plug 20 is provided with grooves 81 to promote tissue in-growth. Such a concept might utilize orifice plugs which are round, spherical, square, etc. In accordance with another embodiment as shown with reference to FIG. 39, the orifice plug 20 is provided with a spike or barb 81 designed to promote tissue in-growth.

Figure 40:
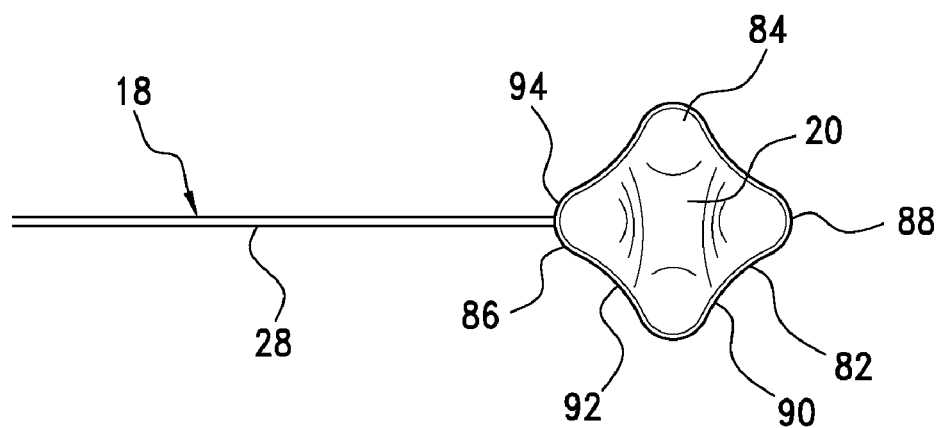
FIGS. 40 and 41 are top plan views showing alternate orifice plug shapes in accordance with the present invention.

Although a spherical orifice plug is disclosed above in accordance with a preferred embodiment, those skilled in the art will appreciate other shapes may be used without departing from the spirit of the present invention. Although reference numeral 20 is used in describing the orifice plug, it will be understood the first and second orifice plugs 20, 22 are identical. In accordance with a first alternate embodiment, and with reference to FIG. 40, the orifice plug 20 takes the form of a "flying saucer". As such, the orifice plug 20 includes an upper conical surface 82 with a domed tip, a central portion 84, and a lower conical surface 86 with a domed tip. More particularly, the upper conical surface 82 is substantially cone-shaped with a concave wall and extends from a rounded crown section 88 to a wider base section 90 which transitions into the central portion 84. The central portion 84 is substantially circular in cross section with a convex wall and extends from a smaller top radius portion to a large central radius portion and back to a smaller bottom radius portion. Beneath the central portion 84 is the lower conical surface 86 that is a mirror image of the upper conical surface 82 and, therefore, extends from a relatively large radius base section 92 to a rounded crown section 94 at its lowest extent.

Figure 41:
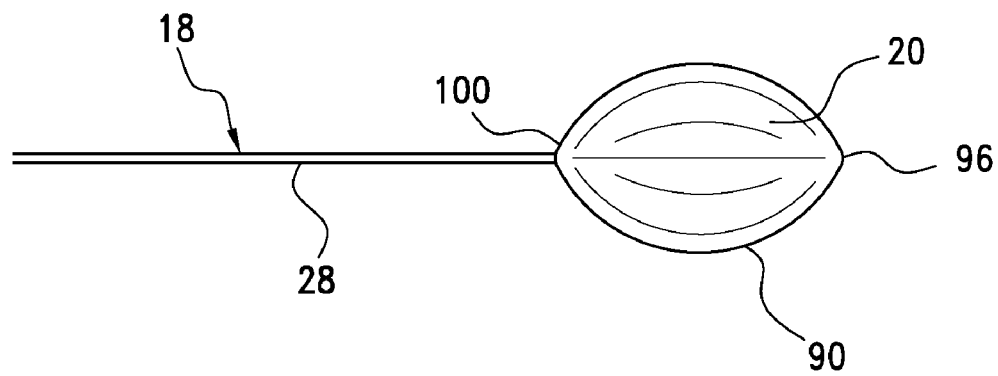

Referring to FIG. 41, an orifice plug 20 with a football shape is disclosed. This shape includes a convex outer wall and a circular cross section when viewed in a plane perpendicular to the longitudinal axis of the orifice plug 20 that goes from a relatively small radius first tip member 96 to a large radius central section 98 and back to a small radius second tip member 100.

Figure 42A:
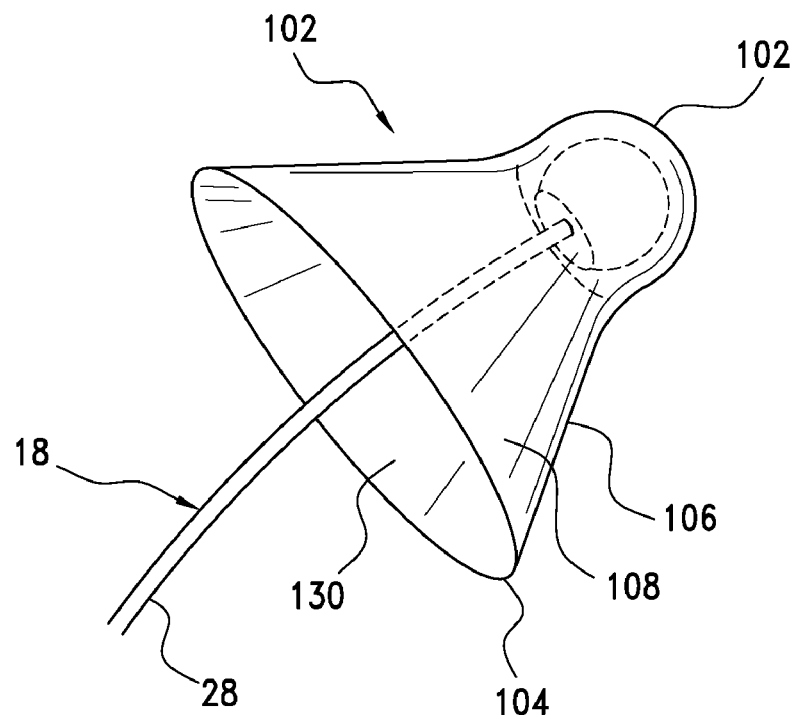
FIGS. 42A and 42B respectively show a perspective view of an alternate shape for an orifice plug and a side schematic view of the same orifice plug positioned within the fallopian tube.
Figure 42B:
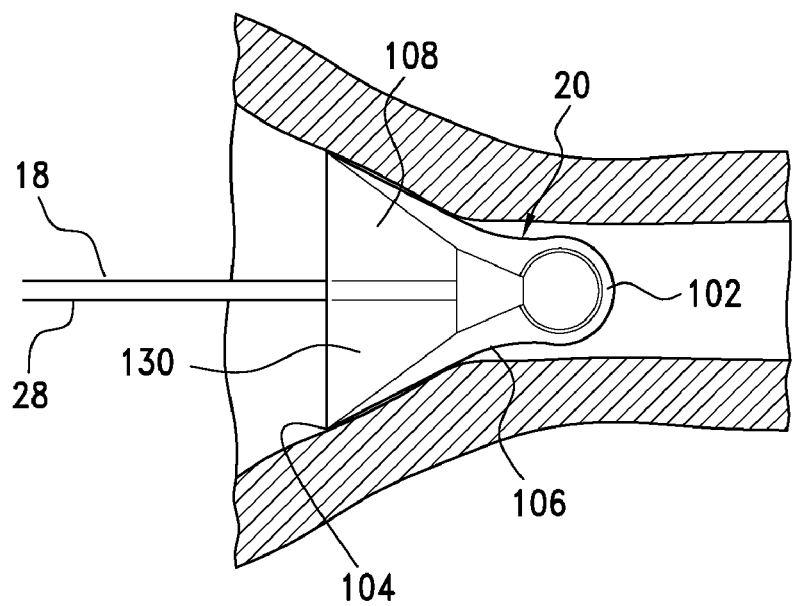

Referring to FIGS. 42A and 42B, a bell-shaped orifice plug 20 may be employed. The bell-shaped orifice plug 20 includes a rounded crown section 102 which extends outwardly as it moves from the tip toward the rim 104 of the bell to create a substantially straight or concave outer surface 106 along the sidewalls 108 of the orifice plug 20. In accordance with a preferred embodiment, the rounded crown section 102 is substantially solid and the portion of the orifice plug 20 along the sidewalls 108 is hollow (defining a cavity 130 along the underside of the orifice plug 20) adding flexibility to the sidewalls 108 as they extend to the rim 104 of the bell.

Figure 43:
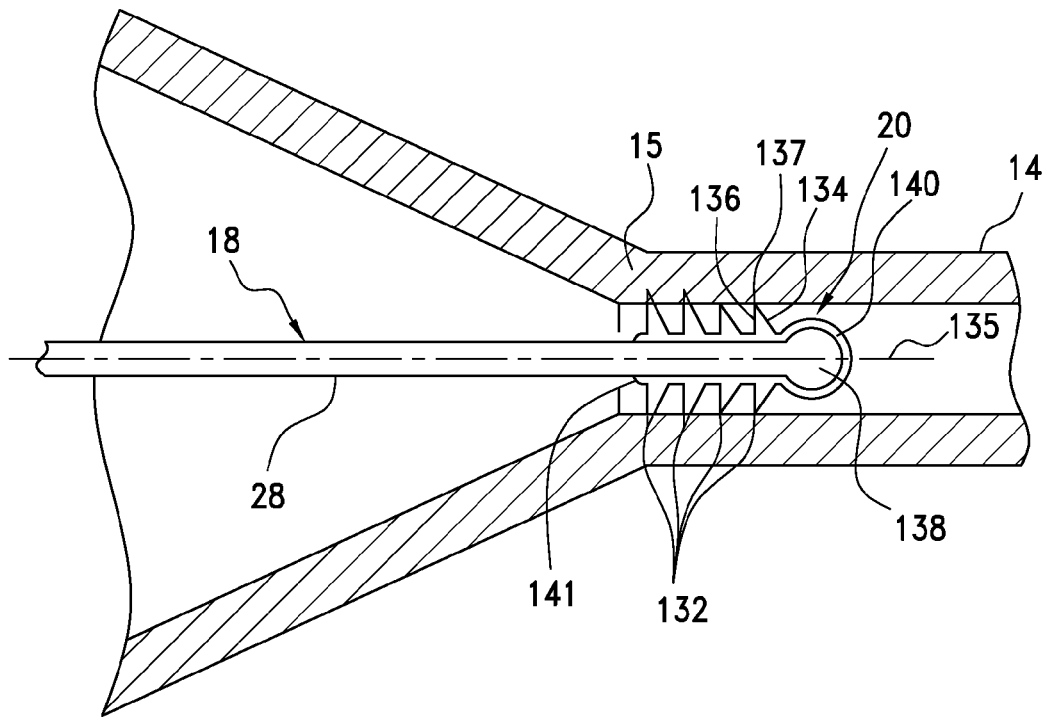
FIGS. 43, 44, 45, 46A, 46B and 46C are schematics of alternate embodiments of orifice plugs that may be used in accordance with the present invention.

With reference to FIG. 43, the orifice plug 20 may also be formed with multiple ring members 132 where one skilled in the art might pursue a tapered progression of shapes, possibly ring-like in geometry. Each of the ring members 132 includes a forward facing surface 134 and a rearward facing surface 136. The forward facing surface 134 is angled for creating an acute angle relative to the fallopian tube 14 into which it is inserted (that is, the forward facing surface 134 tapers proximally as it extends from the central longitudinal axis 135 of the orifice plug 20 toward the free end 137 thereof to facilitate insertion while the rearward facing surface 136 is oriented to create a substantially perpendicular angle relative to the fallopian tube 14 to hinder removal from the fallopian tube 14 after insertion. The ring members 132 each form a seal that engages the wall of the fallopian tube 14 creating a barrier thereof. A round ball member 138 is formed at the distal end 140 of the orifice plug 20. The addition of the round ball member 138 helps in reducing trauma to the tissue as the orifice plug 20 is inserted within fallopian tube 14.

The multiple ring members 132 increase the likelihood of creating a complete barrier. The material from which the ring members 132 are manufactured could be hard or soft and the successive radii of the ring members 132 preferably increase in diameter over an appropriate length as the orifice plug 20 extends from its distal end 140 toward its proximal end 141. As a result, the orifice plug 20 would seal repetitively starting within the fallopian tube 14 and progressing out past the ostium 15.

Figure 44:
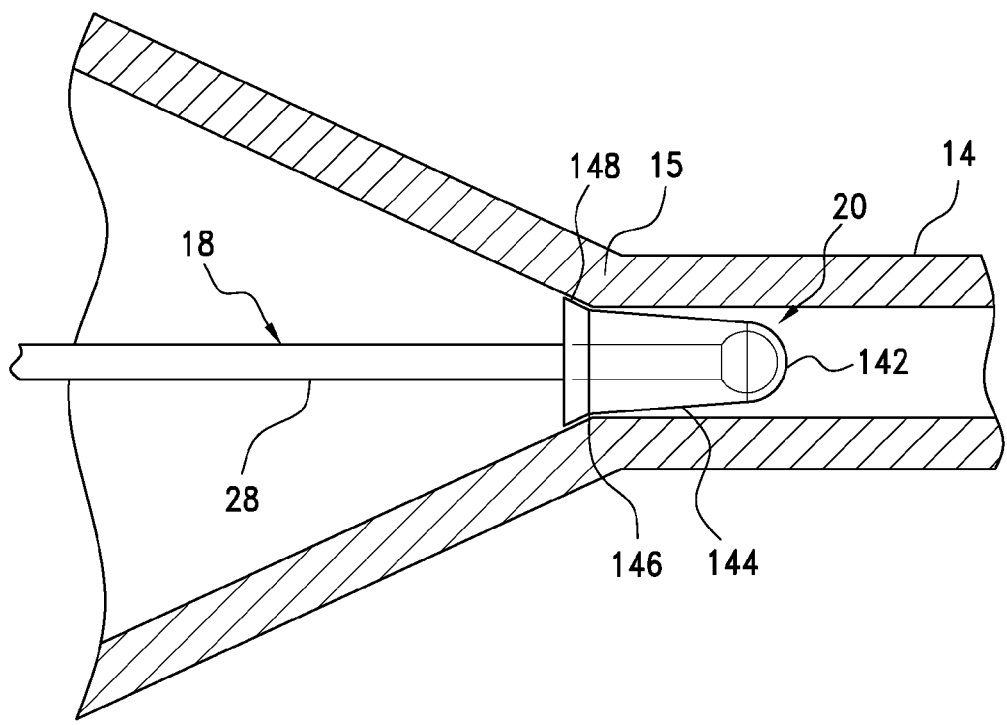

Referring to FIG. 44, a further embodiment of an orifice plug 20 is disclosed. This orifice plug 20 includes a rounded tip 142 and an outwardly tapering wall 144. At the proximal end 146 of the outwardly tapering wall 144 is formed a thin pliable flange 148. The flange 148 functions as both the edge of the orifice plug 20 and a face for sealing the fallopian tube 14 at the ostium 15 from the external environment.

Figure 45:
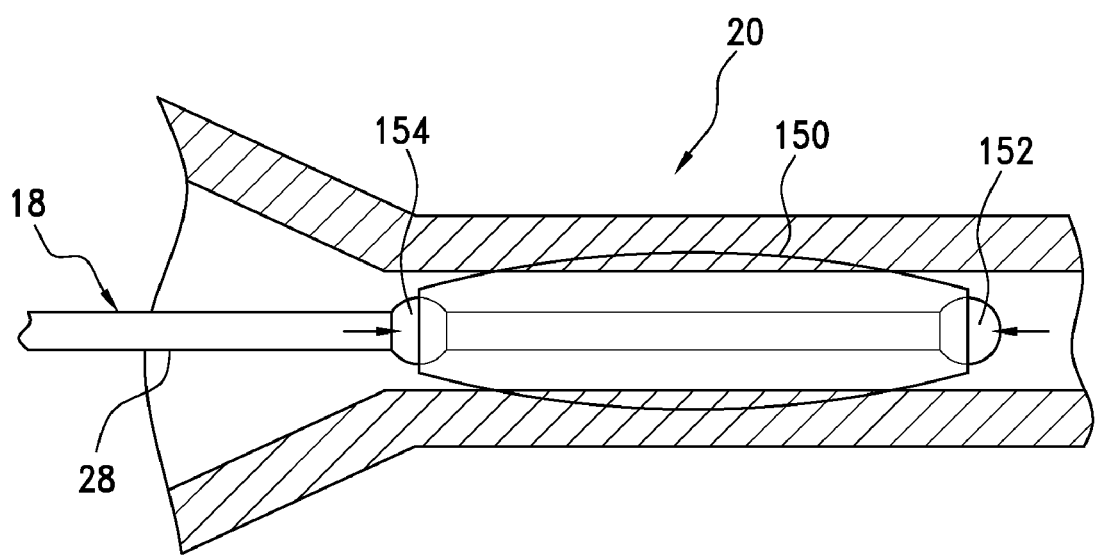

Yet a further embodiment is disclosed with reference to FIG. 45. This embodiment includes an orifice plug 20 with a prolate spheroid shape, that is, a sphere elongated in the direction of a line joining the poles of the sphere (in this case the longitudinal axis of the orifice plug 20). The shape is achieved by securing a tube-like member 150 in a compression state between first and second constraining members 152, 154 at the respective distal and proximal ends of the orifice plug 20. In accordance with a preferred embodiment of this design, the tube-like member 150 is secured to pliable balls, that is, the constraining members 152, 154 at the respective distal and proximal ends of the orifice plug 20.

Figure 46A:
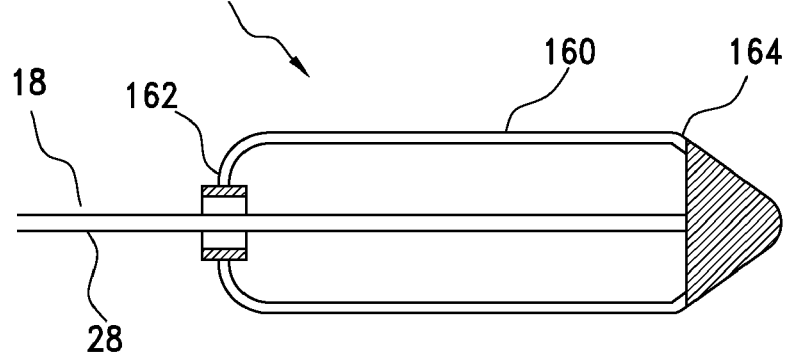
Figure 46B:
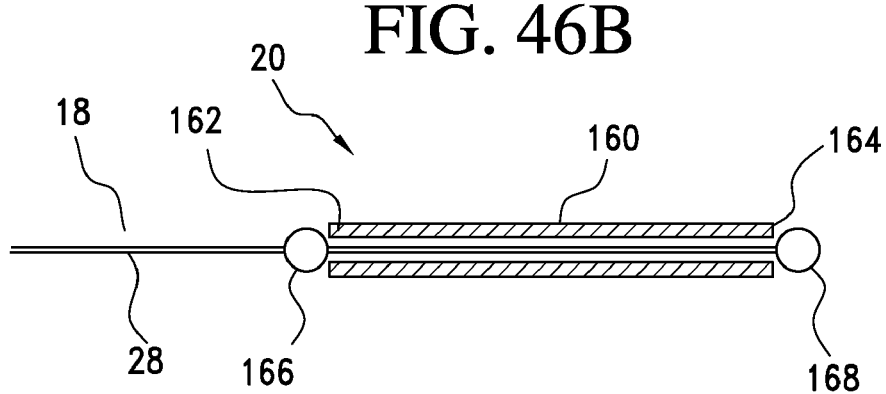
Figure 46C:
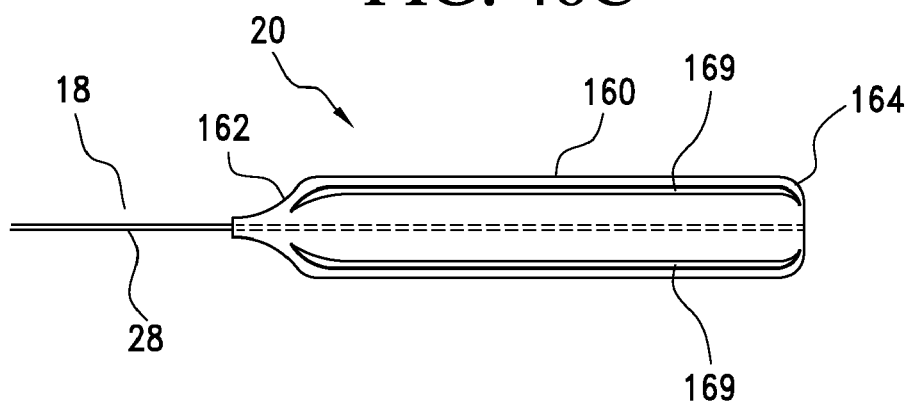

Referring to FIGS. 46A, 46B and 46C, the orifice plug 20 may be designed with a self-adjusting configuration whereby the diameter thereof extends outwardly upon insertion within the fallopian tube. In accordance with each of these embodiments, a biocompatible polymeric, tube-like member 160 spans the length of the orifice plug 20 and is restrained in a manner allowing expansion or contraction thereof such that the diameter of the tube-like member 160 selectively increases as the proximal end 162 and distal end 164 thereof are moved toward and away from each other (see FIGS. 46A and 46B) or as the tube-like member 160 expands (see FIG. 46C). With regard to the embodiment shown in FIG. 46A, the tube-like member 160 is made from a material which contracts upon positioning within the fallopian tube. This will cause the proximal end 162 of the tube-like member 160, which is coupled to the elongated member 28 for movement relative to the elongated member 28, to move toward the distal end 164 of the tube-like member 160 and result in an increase in the diameter of the tube-like member 160. As to the embodiment shown in FIG. 46B, the proximal end 162 and the distal end 164 of the tube-like member 160 are restrained by respective first and second abutment members 166, 168 formed along the elongated member 28. In at least this region, the elongated member 28 is made of a shape memory material, for example, Nitinol, and the distance between the first and second abutment members 166, 168 decreases upon the placement of the orifice plug 20 within the fallopian tube. This will cause the proximal end 162 of the tube-like member 160 to move toward the distal end 164 of the tube-like member 160 and result in an increase in the diameter of the tube-like member 160. As to the embodiment shown with reference to FIG. 46C, the tube-like member 160 is provided with elongated slots 169 allowing for expansion of the tube-like member 160 when it is placed within the fallopian tube. The tube-like member 160 is made from a material which expands upon positioning within the fallopian tube. This will cause outward expansion of the tube-like member 160 since the distal end 164 and proximal end 162 of the tube-like member 160 are fixedly coupled to the elongated member 28.

Figure 47A:
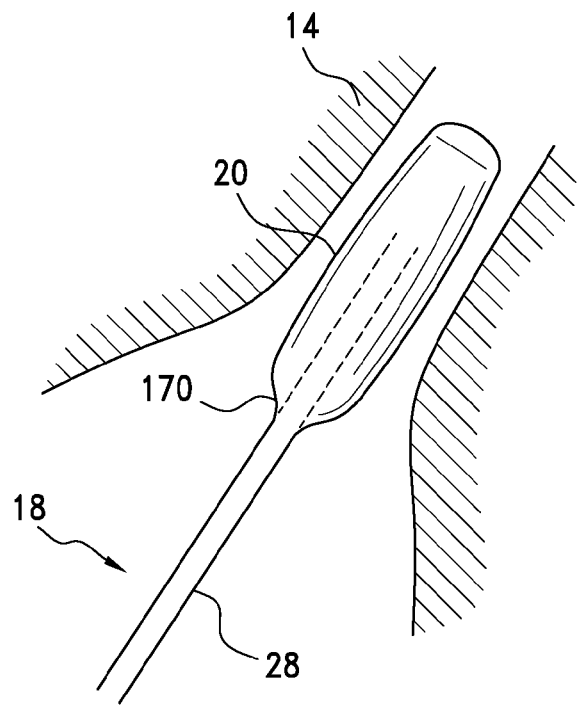
FIGS. 47A and 47B are side schematic views of an alternate orifice plug in accordance with the present invention before and after expansion thereof within the fallopian tube.
Figure 47B:
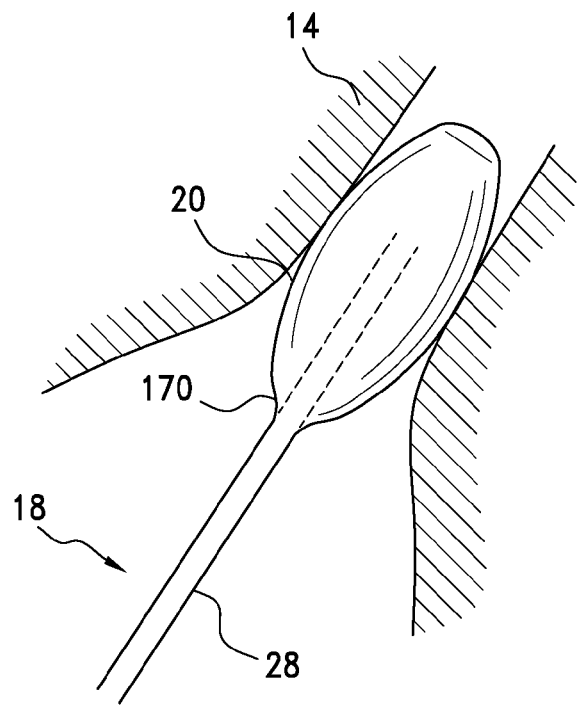

Once again, and referring to FIGS. 47A and 47B, an expanding orifice plug 20 is disclosed. The orifice plug 20 is manufactured from an elastic material which expands upon placement in the fallopian tube 14. Swelling may be achieved by means of applying a temporary tension to the proximal portion 170 of the elastic orifice plug 20 which is then either released based upon positioning of the orifice plug 20 relative to a predetermined anatomical structure or released over a time delay. In addition, the orifice plug 20 could be manufactured from a hydrophilic substance that swells during insertion so as to alter its shape. By allowing the orifice plug 20 to swell inside the fallopian tube 14, the lumen is occluded. In addition, the orifice plug 20 could be positioned within the uterine cavity sealing on the ostia and a smaller plug, once past the cervical limitations, swells to the desired shape. In accordance with a preferred embodiment of the present invention, the swelling material could be comprised of a single compound or a combination of compounds yielding different properties, such as, durability, reaction deployment and conformance, thereby producing a superior seal. A hydrogel polymeric compound is considered an appropriate material for this purpose at it relies on the ambient moisture of the physiology to cause the swelling activation. It is further contemplated swelling might be achieved by the application of energy (i.e., foaming agents) either by application (i.e., RF energy, ultrasonic) or by ambient energy (i.e., core body heat).

Figure 48:
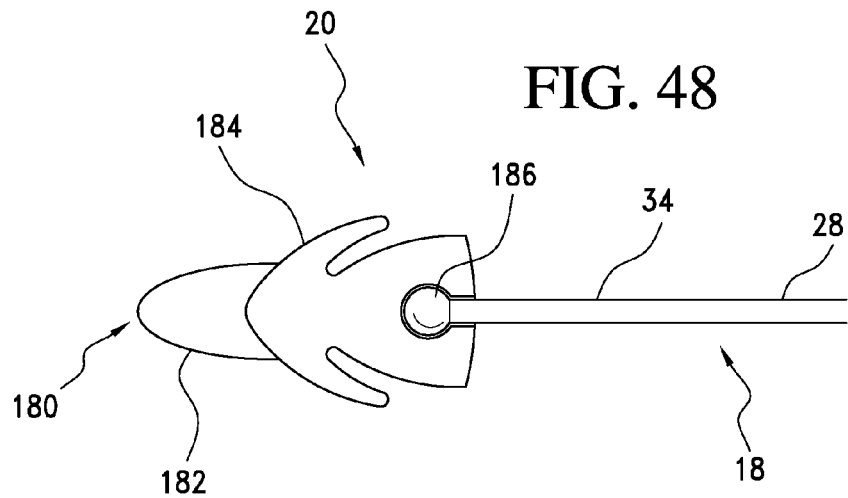

Further, and with reference to FIG. 48, a ball and socket arrangement for an orifice plug 20 is disclosed. In accordance with such an embodiment, the orifice plug 20 is designed with a leading end 180 having a guiding nose 182 shaped and dimensioned to find the fallopian tube and align therewith. Once the fallopian tube is found, an elastomeric plug member 184 is forced within the fallopian tube. Articulation of the orifice plug 20 is achieved by coupling the plug member 184 to the first (and second) leg 34 via a ball joint 186. The ball and socket joint of this embodiment would provide the orifice plug 20 with a degree of freedom to swivel and angularly align with the ostium creating a more even distribution of sealing force and area.

Figure 49:
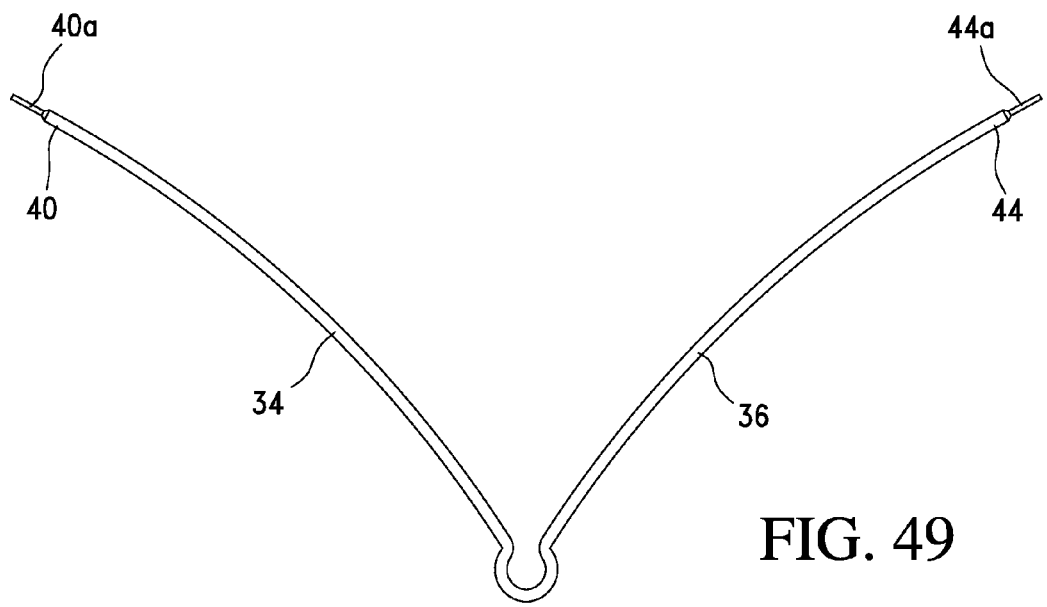
Figure 50:
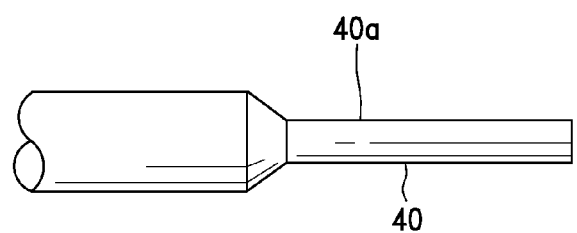

In accordance with an alternate embodiment, and with reference to FIGS. 49 and 50, a flexibility similar to the ball and socket arrangement may be achieved by reducing the cross sectional area at the second ends 40, 44 of the respective first and second legs 34, 36 to achieve a higher flexibility and improved compliance to the uterine cavity shape. As a result, the second ends 40, 44 at each of the respective first and second legs 34, 36 are provided with a reduced diameter section 40a, 44a allowing for greater flexibility of the elongated member 28 in the area adjacent the first and second orifice plugs 20, 22.

Figure 51:
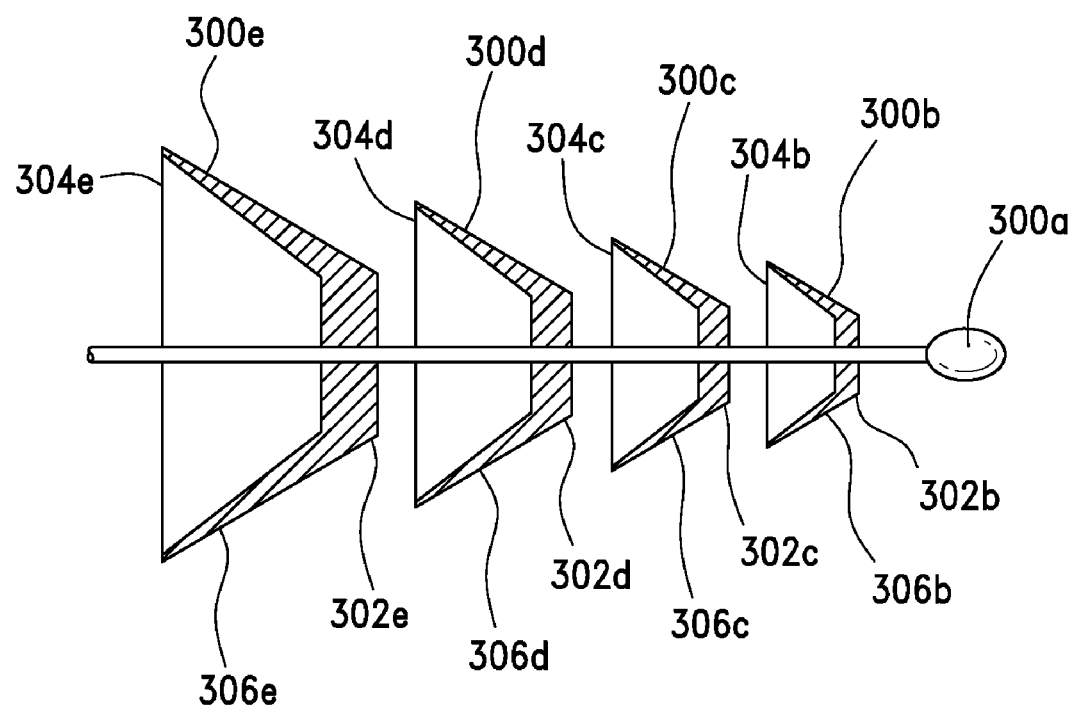

Referring to FIG. 51, where it is desired that the orifice plug 20, 22 be partially within the orifice 12 of the fallopian tubes 14 and partially within the fallopian tubes 14, the orifice plug 20, 22 may be formed with a plurality of orifice plug members 300a-e which increase in size as they move from the second ends 40, 44 of the respective first and second legs 34, 36 to a more proximal position along the first and second legs 34, 36. As shown in FIG. 51, distal most orifice plug member 300a is spherical and substantially similar to the spherical orifice plugs discussed above. Each of the remaining orifice plug members 300b-e includes a distal end 302b-e and a proximal end 304b-e. Each of the orifice plug members 300b-e is formed in the shape of a substantially truncated cone with the diameter thereof increasing as the orifice plug member 300b-e extends from the distal end 302b-e thereof to the proximal end 304b-e thereof. The wall 306b-e of each orifice plug member 300b-e decreases in thickness as it extends from the distal end 302b-e thereof to the proximal end 304b-e thereof. Because of the relative size and shape of the orifice plug members 300b-e, the distal most orifice plug member(s) is shaped and dimensioned to seat within the fallopian tubes 14 while the more proximally oriented orifice plug member(s) is shaped and dimensioned to seat within the orifices 12 of the fallopian tubes 14.

As discussed above, the orifice plugs are composed of silicone in accordance with a preferred embodiment. However, and for each of the orifice plug shapes disclosed above, the orifice plug may be formed in a dual density configuration of various biocompatible elastomers. In particular, and with reference to FIG. 52, the inner portion 188 of the orifice plug 20 is made from a relatively hard material and forms a foundation for the orifice plug 20. Affixed over the inner portion 188 is an outer soft pliable material 190. The soft pliable material 190 forms the outer surface 191 of the orifice plug 20 and is believed to form a better seal at the entrance of the fallopian tube based upon its conforming nature.

In accordance with an alternate embodiment, and with reference to FIG. 53, the orifice plug 20 maybe formed with a hard outer shell 192 (for example, gelatin tablet material) temporarily affixed to the outer surface 27 of the main orifice plug body 23 of the orifice plug 20 that is made of a soft pliable material (or a dual density configuration as described above) for the purpose of protecting the softer inner material. The hard outer shell 192 behaves like a slippery surface during insertion and deployment. However, the hard outer shell 192 is composed of a bioabsorbable or decomposable (that is, expelled during normal menstrual cycle) material which quickly dissolves upon deployment within the fallopian tube. As a result, the hard outer shell 192 dissolves and is discharged or absorbed allowing the soft pliable material of the outer surface 27 to ultimately seat occluding the fallopian tube.

Figure 54:
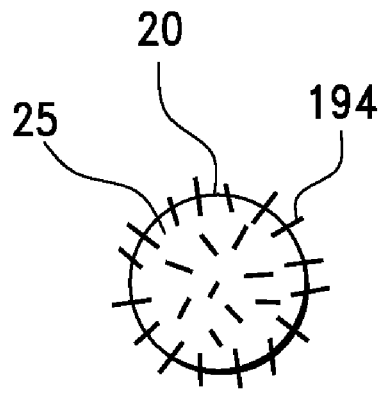
Figure 55:
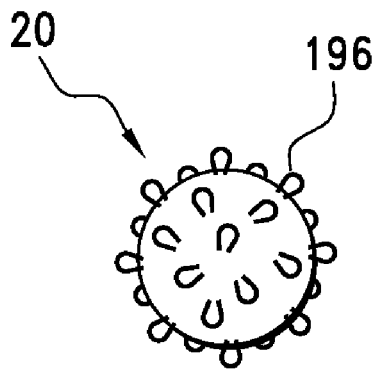

As discussed above in accordance with a preferred embodiment, enhanced coupling of the orifice plug to the tissue surface is achieved by the application of a tissue in-growth member of mesh about the silicone outer surface of the orifice plug. However, it is contemplated other techniques may be employed to achieve desirable coupling of the orifice plug within the fallopian tubes. For example, and in accordance with one embodiment as shown with reference to FIG. 54, the outer surface 25 of the orifice plug 20 is provided with tissue in-growth promoting/compatible whiskers 194. The tissue in-growth promoting/compatible whiskers 194 help to integrate the orifice plug 20 within the anatomy and ensure a substantial seal. Similarly, and with reference to FIG. 55, tissue in-growth promoting/compatible loops 196 may be integrated into the orifice plug 20 for the same purpose of securing the same to the anatomy and creating a seal. Where such tissue in-growth promoting structures are employed, they may be composed of bioresorbable or bioabsorbable materials such that the orifice plugs will completely dissolve over a predetermined period of time or they may simply be composed of tissue in-growth promoting materials that will remain stable until such a time the orifice plugs are removed.

Figure 56:
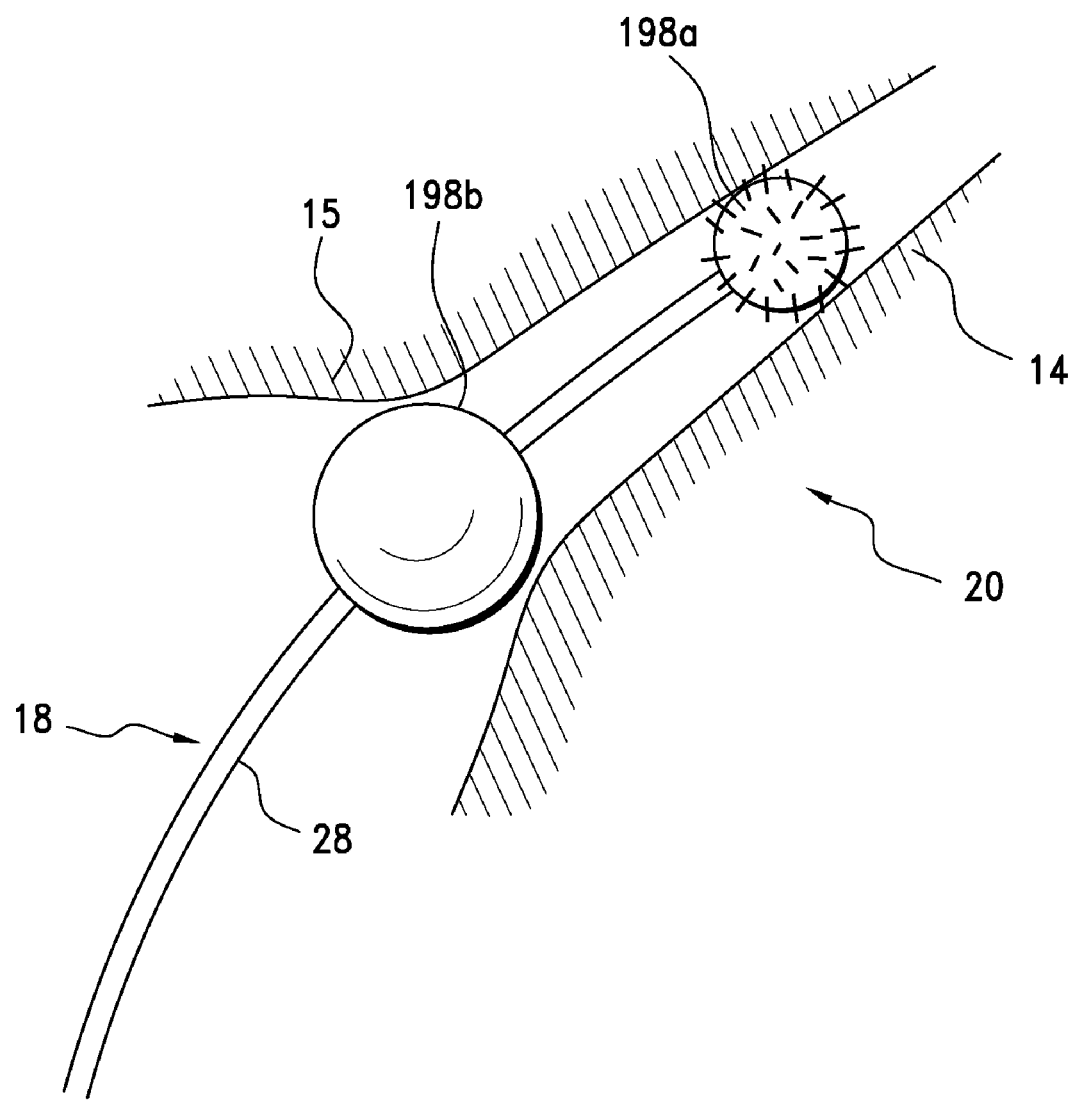

In accordance with yet a further embodiment, and referring to FIG. 56, a series of plug members 198a, 198b may be formed along the length of the first (and second) legs 34. In accordance with such an embodiment it is contemplated the distal most plug member 198a would have a smaller diameter than the more proximal plug member 198b. The smaller plug member 198a would be provided with or without tissue in-growth treatment and would be small enough to pass the ostium 15 and assist in guiding the device into the fallopian tube 14. The larger plug member 198b would be sufficiently sized for guiding to the ostium 15 and sealing thereon. The smaller plug member 198a located in the fallopian tube 14 would help to maintain the larger plug in position.

While various orifice plug shapes are disclosed herein, it is contemplated orifice plug shapes as disclosed in commonly owned PCT Publication No. WO2006/088909, which is based upon International Application No. PCT/US2006/005245, filed Feb. 15, 2006, entitled "INTRAUTERINE FALLOPIAN TUBE OCCLUSION DEVICE AND METHOD FOR USE", which is incorporated herein by reference, may be employed within the spirit of the present invention.

Figure 6:
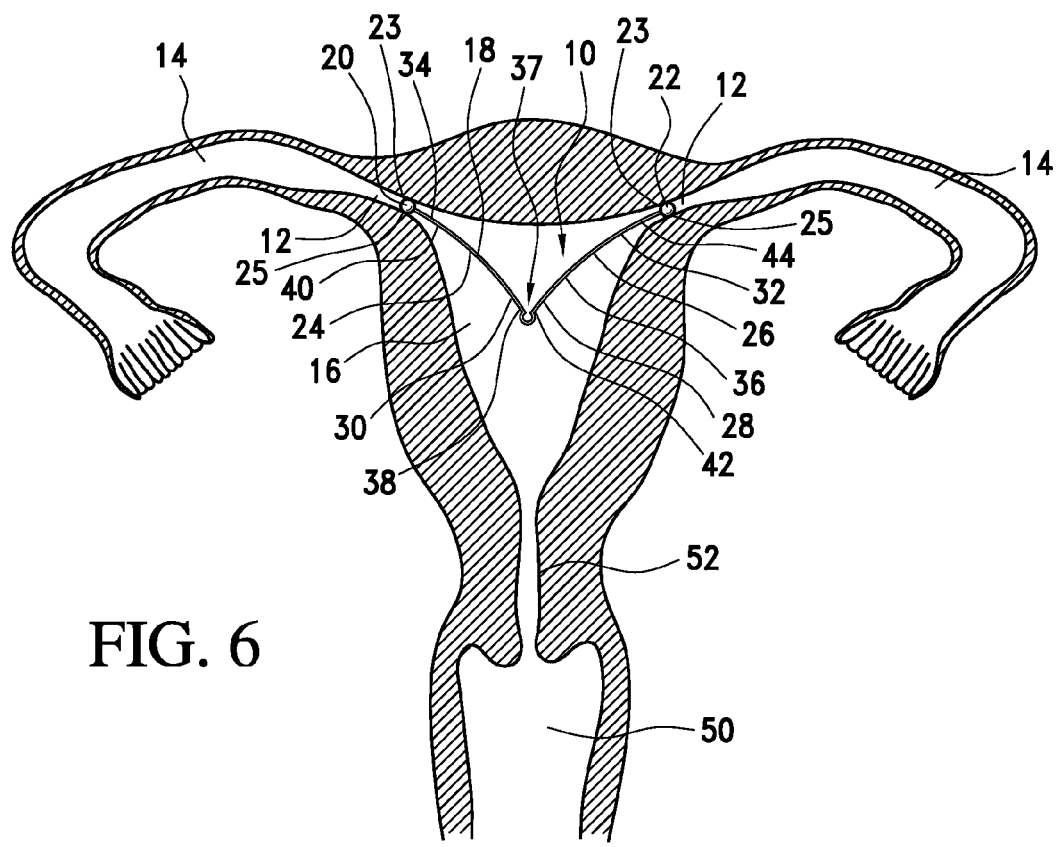
Figure 8:
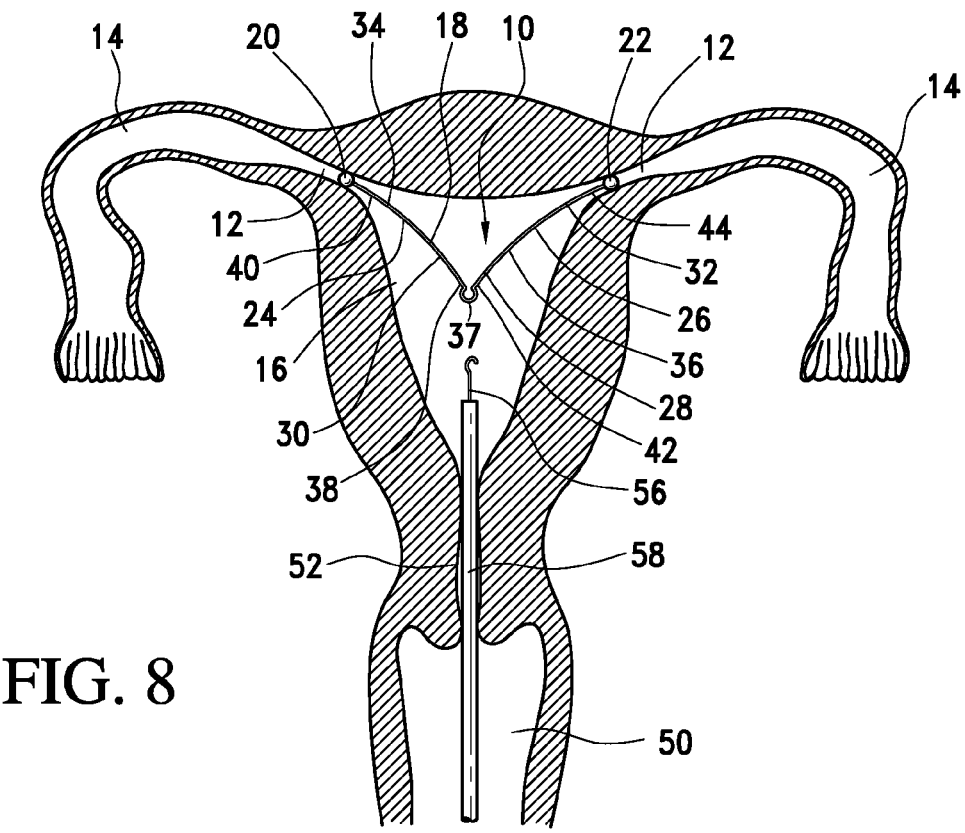
Figure 8A:
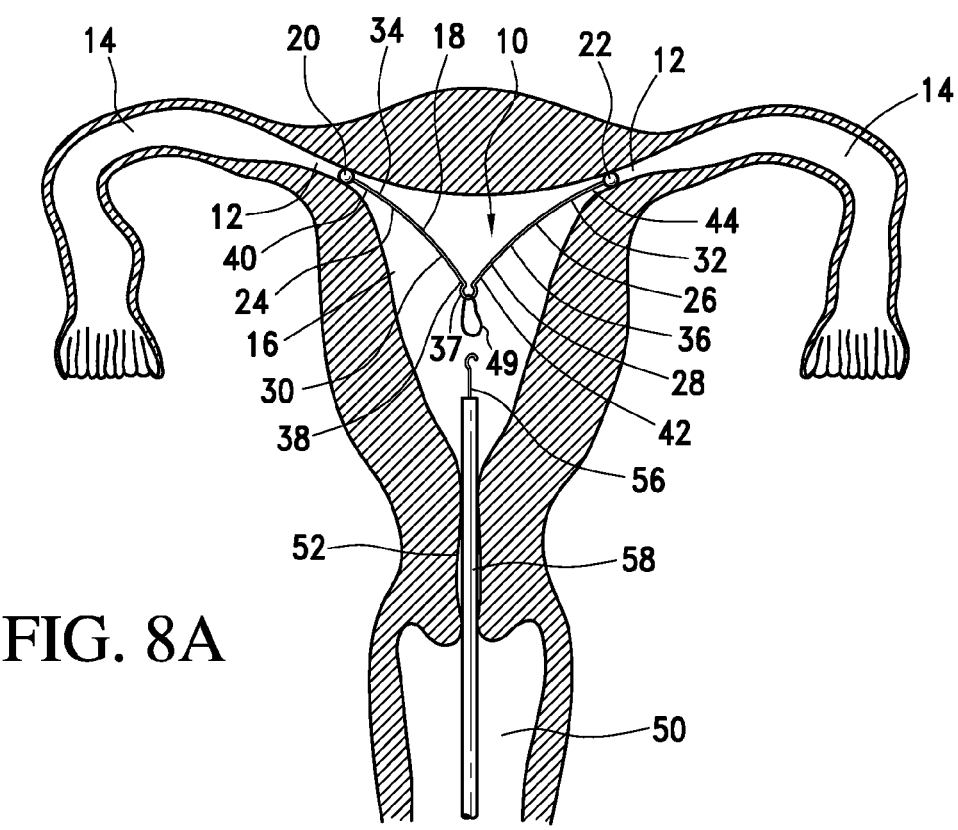
FIG. 8A shows an alternate embodiment in accordance with the present invention.
Figure 62:
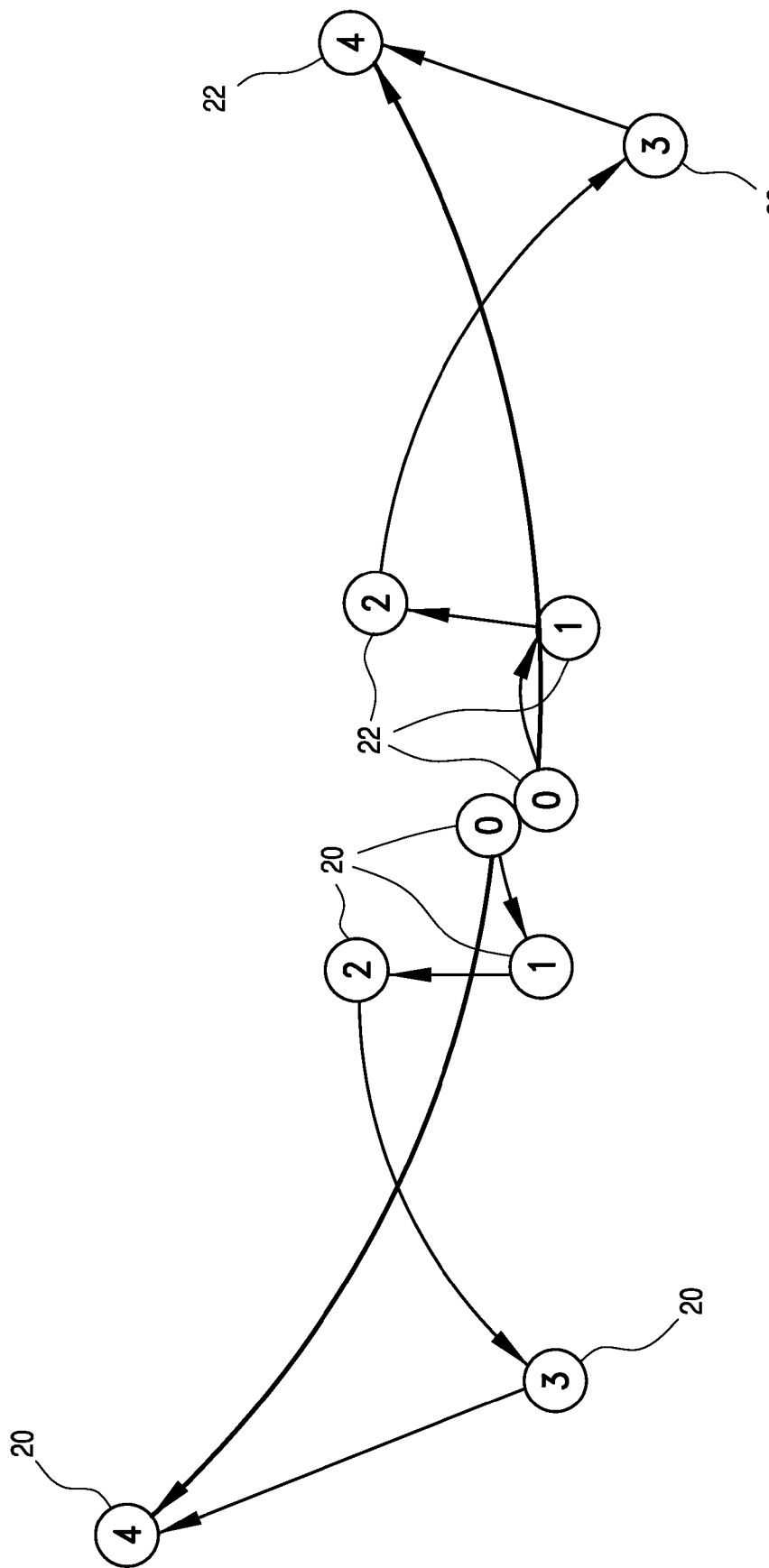
FIG. 62 is a schematic demonstrating movement of the orifice plugs during deployment of the intrauterine occlusion device shown with reference to FIGS. 1-13.

Delivery of the present intrauterine occlusion device is achieved in the manner described with reference to commonly owned PCT Publication No. WO2006/088909, which is based upon International Application No. PCT/US2006/005245, filed Feb. 15, 2006, entitled "INTRAUTERINE FALLOPIAN TUBE OCCLUSION DEVICE AND METHOD FOR USE", which is incorporated herein by reference. Briefly, and with reference to FIGS. 1 to 6 and 62, the intrauterine occlusion device 10 is packaged in a small caliber longitudinal delivery container 48 which forms part of the delivery apparatus 46. This delivery container 48 is advanced into the uterine cavity 16 through the vagina 50 and cervix 52 (FIG. 2 and Points 0 of FIG. 62 which show the position of the orifice plugs 20, 22 at this step of the deployment). Once inside the uterine cavity 16, the intrauterine occlusion device 10 is partially released and advanced from the delivery container 48 via a delivery rod 54 extending through the delivery container 48 for pushing the intrauterine occlusion device 10 from its storage position within the delivery container 48, preferably, while pulling the delivery container (or sheath) 48 back so as to prevent damage to the uterus or intrauterine occlusion device 10. Upon initial deployment, the orifice plugs 20, 22 will first move outwardly due to the stored outward bias in the first and second legs 34, 36 (see Points 1 of FIG. 62 which show the position of the orifice plugs 20, 22 at this step of the deployment). As the intrauterine occlusion device 10 is further deployed, the orifice plugs 20, 22, move upwardly within the uterine cavity 16 (see Points 2 of FIG. 62 which show the position of the orifice plugs 20, 22 at this step of the deployment). Once the intrauterine occlusion device 10 is fully or almost fully released from the delivery container 48 during deployment, with the present intrauterine occlusion device 10 no longer being contained by the delivery container 48 (with the delivery rod 54 secured thereto in accordance with a preferred embodiment), the first and second legs 34, 36 and the connection member 37 bow outwardly allowing the intrauterine occlusion device 10 to take a shape of a "Y" with the orifice plugs 20, 22 in contact with respective opposed walls of the uterine cavity (FIG. 3 and Points 3 of FIG. 62 which show the position of the orifice plugs 20, 22 at this step of the deployment)). As the intrauterine occlusion device 10 further opens with the first and second legs 34, 36 moving apart and the respective orifice plugs 20, 22 applying pressure to the opposed walls of the uterine cavity 16, the orifice plugs 20, 22 of the intrauterine occlusion device 10 distally reach the respective opposed back walls of the uterine cavity 16 and ride up the opposed walls of the uterine cavity 16 directing themselves to the orifices 12 of the fallopian tubes 14 until they seat at the orifices 12 of the fallopian tubes 14 or within the fallopian tubes 14 (FIG. 4 and Points 4 of FIG. 62 which show the position of the orifice plugs 20, 22 at this step of the deployment). At that point when the intrauterine occlusion device 10 can be compressed against the fallopian tube orifices 12 it will be released (FIG. 5), whether manually or automatically, from the delivery apparatus 46. The delivery apparatus 46 will be removed and the present intrauterine occlusion device 10 will stay in place (FIG. 6). With the foregoing in mind, the present invention provides a device and system for implantation positioning whereby an appropriate combination of defined deployment displacement and elastic behavior the implant's occluding portions proximate the ostia.

Figure 61:
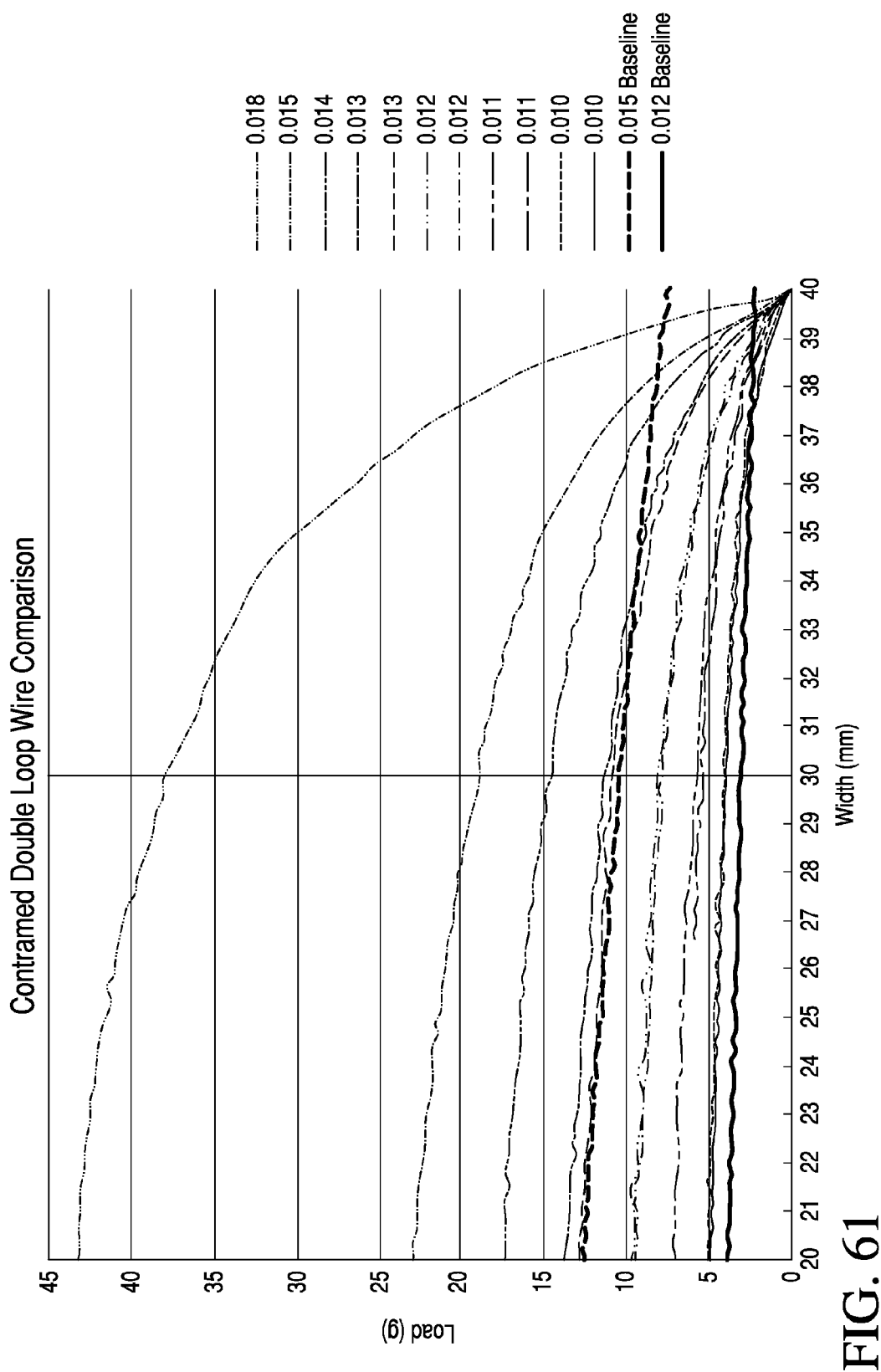
FIG. 61 is a graph showing load profiles for the resilient body in accordance with the present invention.

Control of the applied force is important because the applied force, or pressure, causes irritation and encourages subsequent in-growth of tissue within an in-growth encouraging orifice plug (as disclosed herein) as the orifice plug contacts the wall of the uttering cavity and/or the orifice of the fallopian tube. With this in mind, the deployed intrauterine occlusion device 10 is designed to apply pressure within the uterine cavity and/or the orifices of the fallopian tubes in a manner causing irritation and encouraging tissue in-growth into the first orifice plug and the second orifice plug. More particularly, testing has revealed the orifice plugs must preferably span a distance of approximately 18 mm to approximately 54 mm depending upon the anatomical characteristics of the patient. The elongated member (regardless of the embodiment as described herein) is, therefore, capable of moving (for example, spreading based upon the inherent spring bias) to spread the first and second orifice plugs from between approximately 18 mm and 54 mm apart. The present intrauterine occlusion device, in particular, the elongated member, must further be capable of applying a relatively consistent force (for example, a load of approximately 5 grams in accordance with a preferred embodiment) while the orifice plugs are positioned anywhere within the desired span between the orifices of the fallopian tubes. In accordance with a preferred embodiment, the load required for the application of the force necessary to encourage in-growth is preferably approximately 5 to 50 grams, and more preferably 15 to 30 grams, when such a load is applied for a period of 1 to 3 months. Each of the embodiments disclosed herein attempts to accommodate these requirements with the controlled application of force. For example, the embodiment described above with reference to FIGS. 1 to 6 is preferably manufactured from Nitinol which has been found capable of providing relatively consistent application of force across a wide range of orifice plug spans (see FIG. 61 showing the load profiles for Nitinol at various rod thicknesses). Irritation (and/or damage) encouraging tissue in-growth may be further facilitated by applying corrosive material to the surface of the orifice plug.

A proposed embodiment for the delivery apparatus 46 is illustrated in FIGS. 7A to 7D. This illustration shows the delivery apparatus 46 with its orifice plugs 20, 22 arranged longitudinally within the delivery container 48. Because of the need to maintain the delivery container 48 in the lowest profile possible (the bigger the delivery system the more dilatation of the cervix is needed), the orifice plugs 20, 22 are located, staggered, one in front of the other. This also means that the two legs 34, 36 of the intrauterine occlusion device 10 in this embodiment are a slightly different length. It is contemplated this staggered arrangement may be achieved by making one leg shorter than the other or by flexing or bending one of the legs to force a corresponding leg to stay behind the other. Although this embodiment employs a staggered arrangement, it is contemplated the legs may be oriented side by side.

Figure 9:
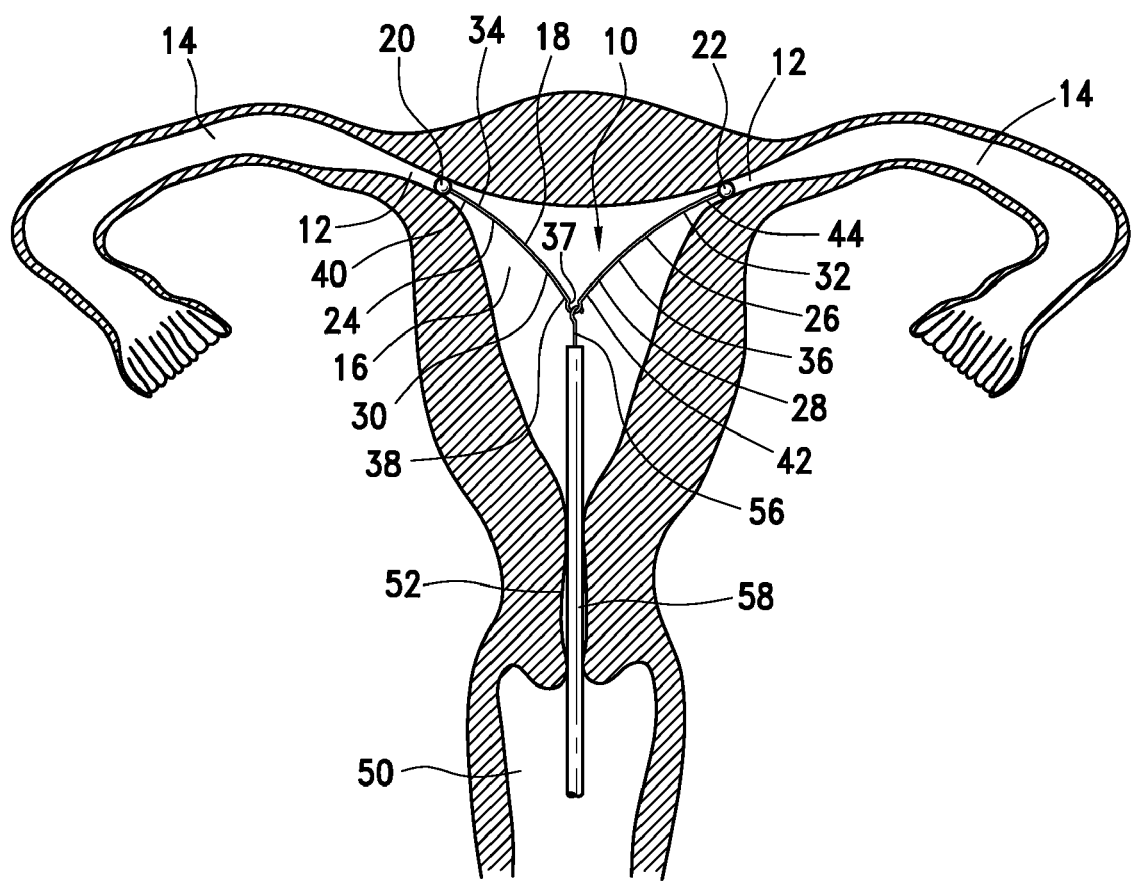
Figure 10:
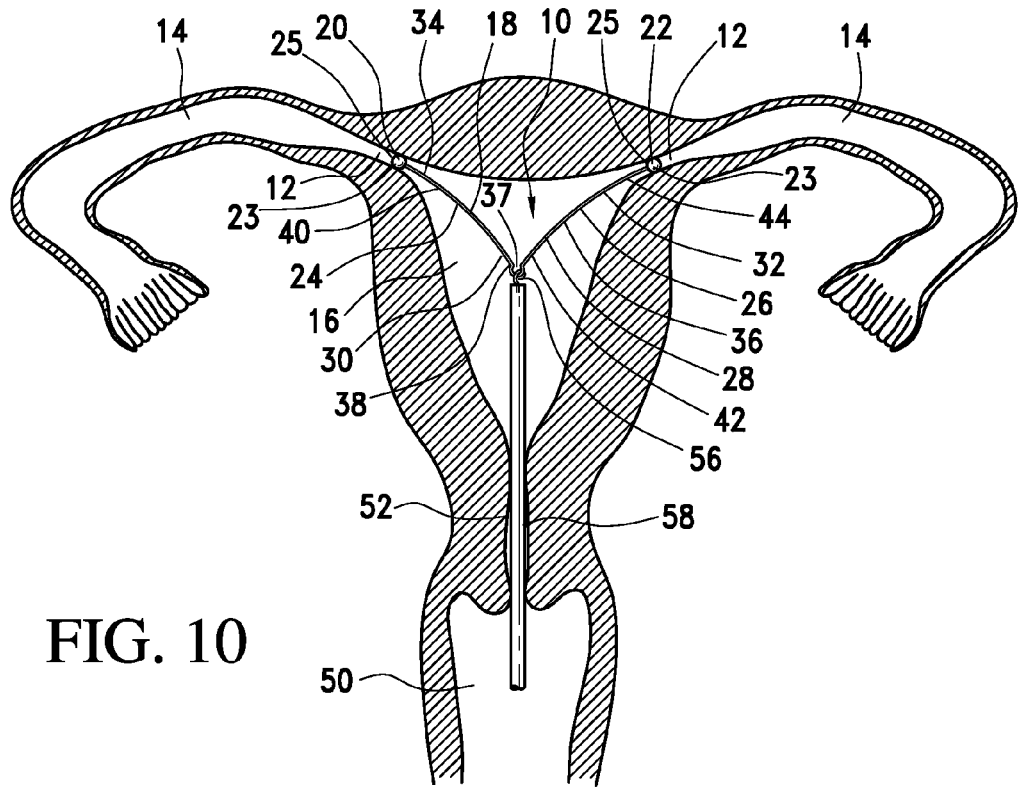
Figure 11:
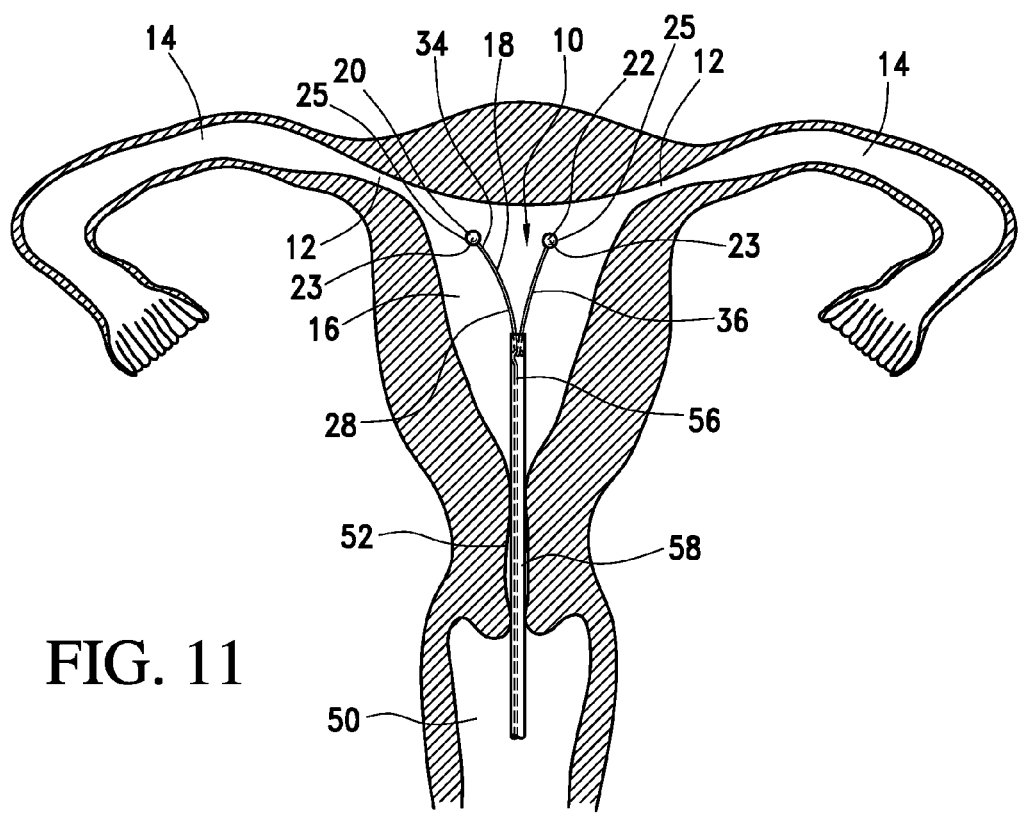
Figure 12:
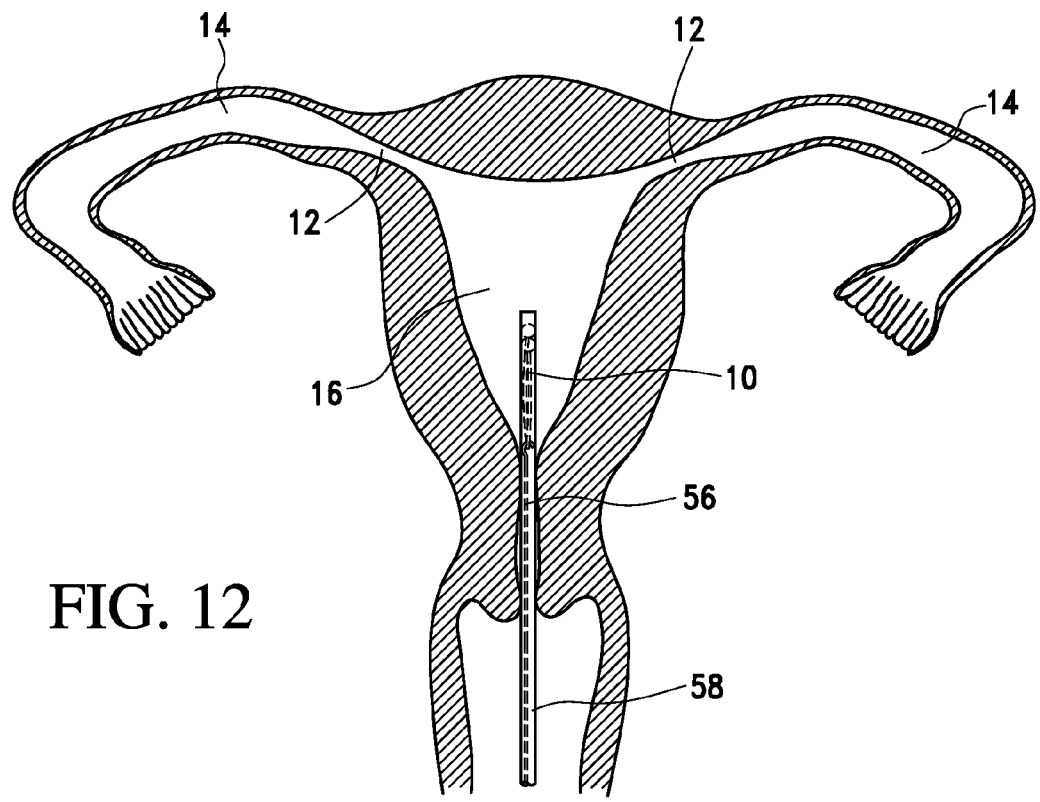
Figure 13:
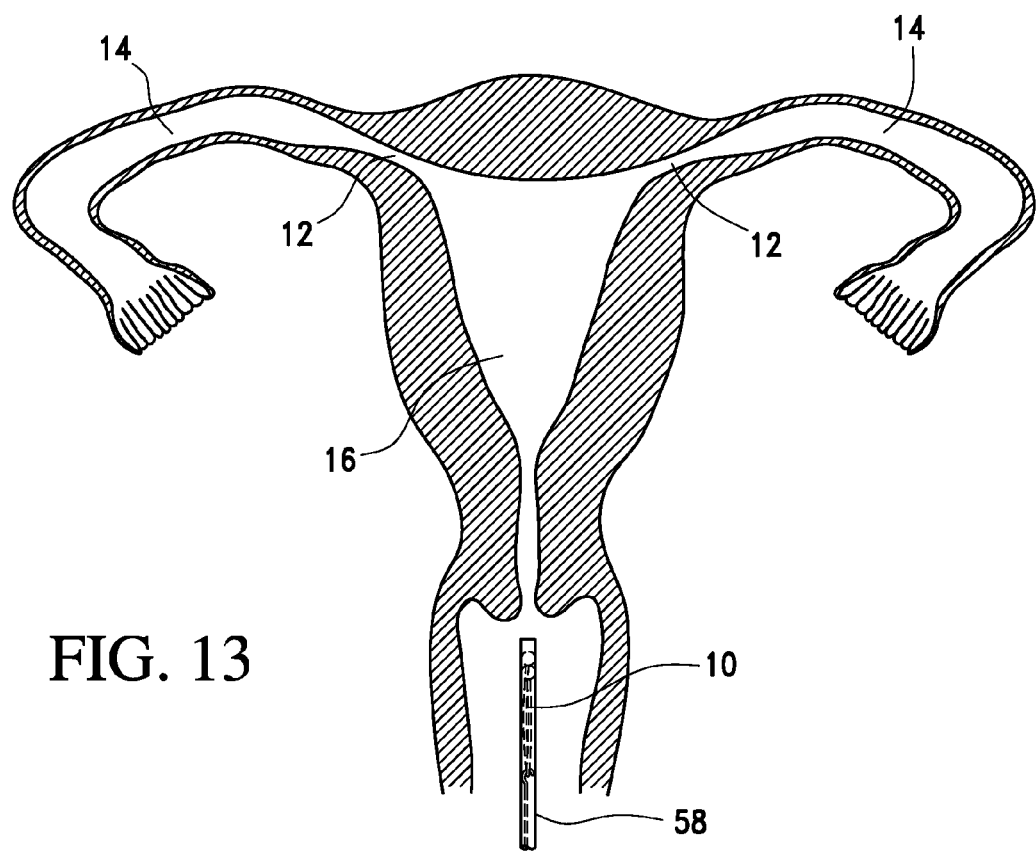

When removal of the intrauterine occlusion device 10 is desired, a hook 56, or other removal apparatus that engages the intrauterine occlusion device 10, will be advanced through the vagina 50 and cervix 52 (FIG. 8) and the connection point (for example, a metallic spring) between the orifice plugs 20, 22 and the first and second legs 34, 36 will be grasped (FIG. 9). The hook 56 will pull on the intrauterine occlusion device 10 and insert it into a sheath 58 or into the hysteroscope (FIGS. 10, 11, 12). At that stage, the contained intrauterine occlusion device 10 is removed from uterus and out through the cervix 52 and vagina 50 (FIG. 13). This removal would be done either with or without direct visualization or under fluoroscopic guidance.

In accordance with an alternate embodiment and with reference to FIG. 5A, a suture/string loop 49 may be secured to the connection member 37. As such, either the hook 56 or other engagement device may grab the suture/string loop 49 for retrieval of the intrauterine occlusion device.

The present device, in addition to being an intrauterine device, will actively occlude the fallopian tubes. This occlusion will prevent sperm or other material from migrating from the uterus to the fallopian tubes and vice versa.

The present device offers a variety of other uses. These uses include applications for contraception, either temporary or permanent; especially for women who do not use IUDs because of the "post fertilization-embryo destruction" mechanism associated with the IUD's birth control. The present intrauterine occlusion device may also be used by women who do not wish to undergo a tubal ligation surgery.

The present intrauterine occlusion device may potentially also be used in the treatment of endometriosis. Back flush of menstrual blood through the fallopian tubes is a proposed mechanism for this disease. The present intrauterine occlusion device will allow occlusion of the fallopian tubes as a possible treatment. Endometriosis usually affects younger patients and other methods of tubal ligation or occlusion are not warranted.

Although a preferred embodiment disclosed above shows the orifice plugs as being permanently coupled to the ends of the resilient body, the resilient body, delivery rod and container may serve as a delivery system of the orifice plugs to the orifices of the fallopian tubes. More particular, and with reference to FIGS. 16, 17 and 18, the concepts underlying the present invention are utilized in conjunction with the shape of the uterine cavity 16 to conform the first and second orifice plugs 120, 122 of the intrauterine occlusion device 110 in the orifices 12 of the fallopian tubes 14. As with the prior embodiments, the orifice plugs 120, 122 may contain any kind of material or medicine to be delivered into the orifices 12 or the fallopian tubes 14.

Figure 19:
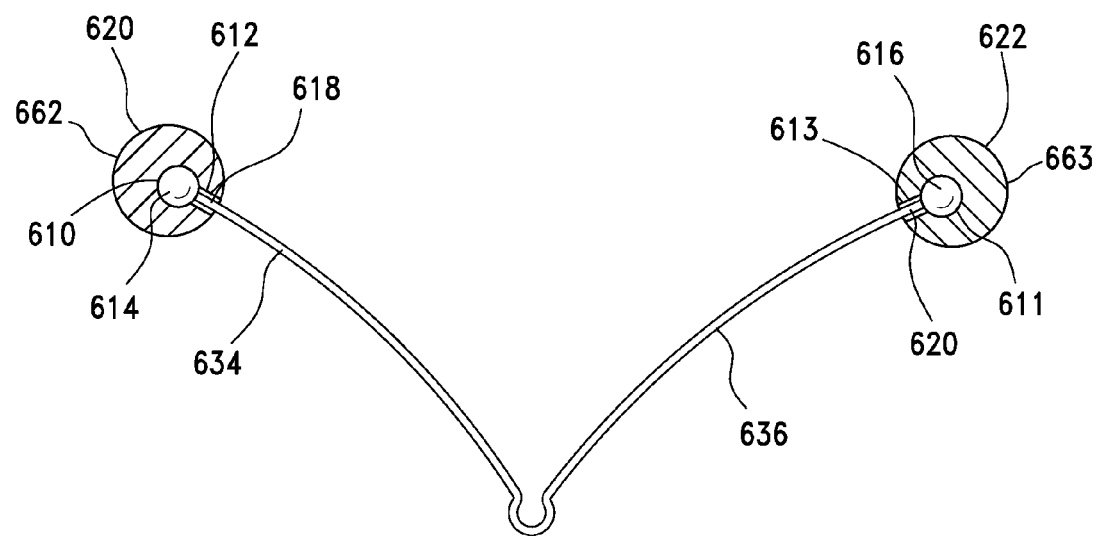
FIG. 19 is a cross sectional view showing a detachable structure for securing orifice plugs to the respective legs.

The orifice plugs 120, 122 are releasably secured to the respective first and second ends 124, 126 of the resilient body 118 and, therefore, may be left in place by separating them from the resilient body 118. As those skilled in the art will certainly appreciate a variety of methods for separation of the orifice plugs 120, 122 with the resilient body 118 may be employed within the spirit of the present invention. For example, release may be achieved by mechanically coupling mechanisms or heat activated release mechanism wherein a coupling structure melts or separates the connection or connections between the plugs and the resilient body when the device is placed within the body (either immediately or over time and hence separate the plugs from the delivery device).

Where release of the plugs is desired, and with reference to FIG. 19, the orifice plugs 620, 622 may be secured to the respective first and second legs 634, 636 via a snap-type connection. Utilizing such a connection, each orifice plug 620, 622 is provided with a central cavity 610, 611 having a resilient passageway 612, 613 extending between the external surface 662, 663 of the orifice plug 620, 622 and the central cavity 610, 611 controlling access thereto. Each of the first and second legs 634, 636 is provided with a ball 614, 616 at its distal end 618, 620, the ball 614, 616 being slightly larger than the flange 612, 613, although applied pressure to the diameter of the passageway 612, 613 will allow pushing of the ball 614, 616 therethrough and into the central cavity 610, 611 of the orifice plug 20, 22. As such, the orifice plug 620, 622 would be secured to the second end 640, 644 of the leg 634, 636 until such a time that someone pulls hard enough on the leg 634, 636 to withdraw the ball 614, 616 thereon from the central cavity 610, 611 and through the flange 612, 613.

Figure 20A:
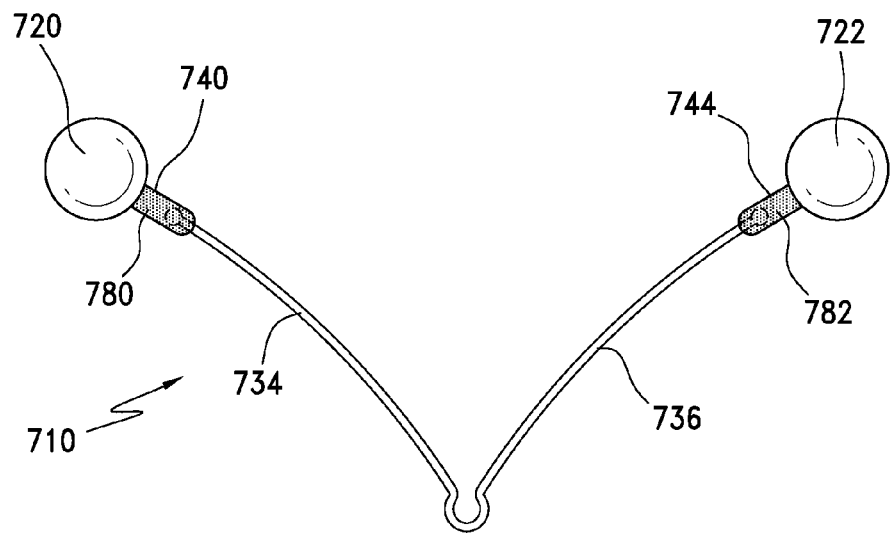
FIGS. 20A, 20B and 20C are various views showing use of an alternate embodiment wherein orifice plugs are detachable secured to the respective legs.
Figure 20B:
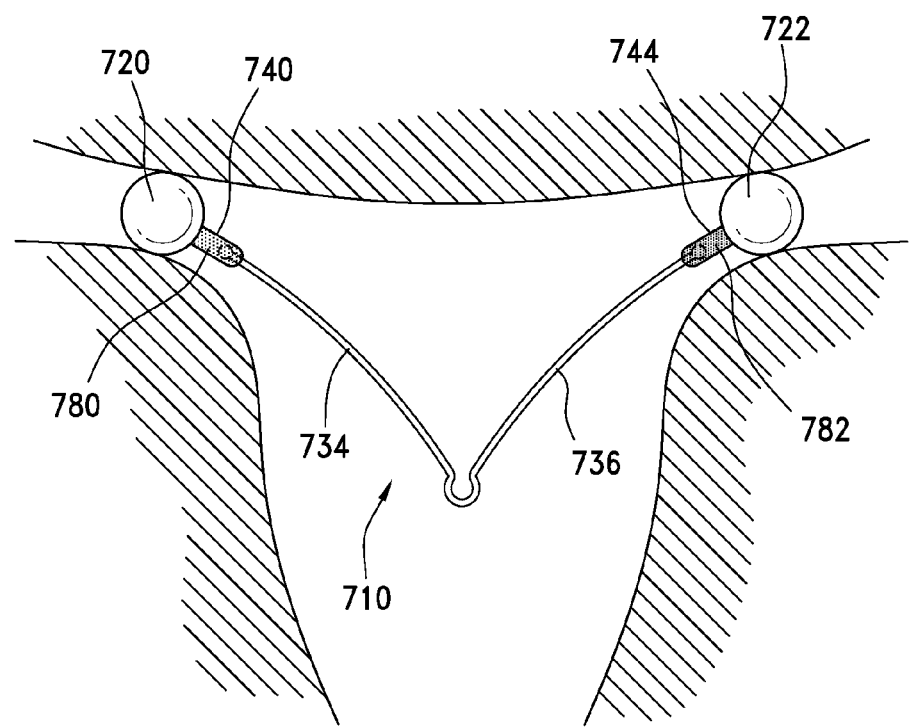
Figure 20C:
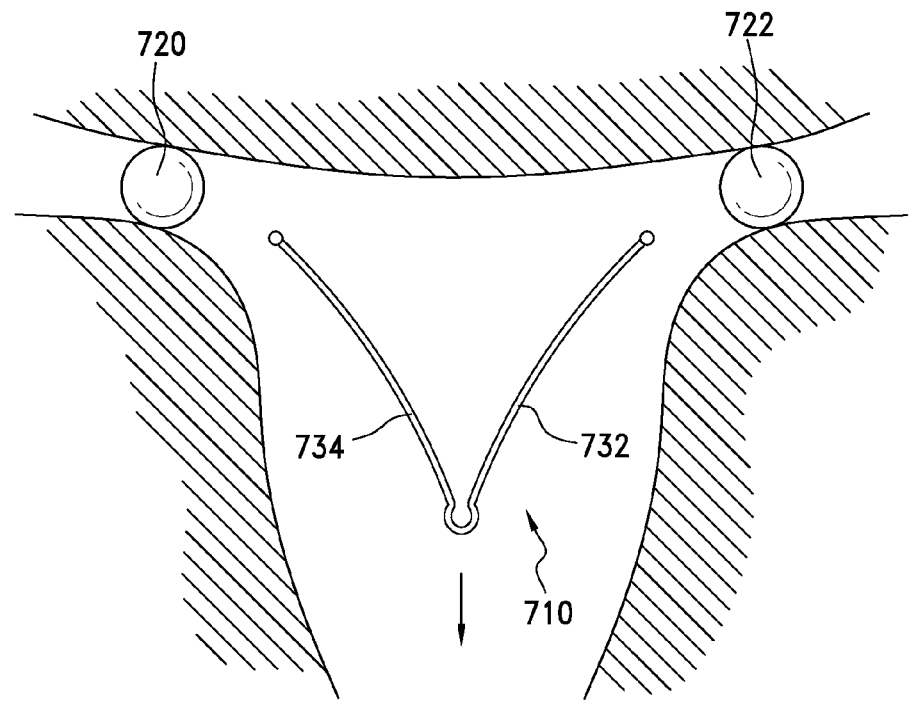

In accordance with another embodiment as shown with reference to FIGS. 20A, 20B and 20C, the second ends 740, 744 of the respective first and second legs 734, 736 are secured to the orifice plugs 720, 722 by way of a resorbable coupling member 780, 782. As a result, when the intrauterine occlusion device 710 is deployed the coupling member 780, 782 will break down releasing the orifice plugs 720, 722 from the respective first and second legs 734, 736 and permit removal of the first and second legs 734, 736 from the uterine cavity 16.

In a system where it is desired to leave the orifice plugs within the fallopian tubes while removing the elongated member, it may be desirable to provide an occlusion device wherein the first and second legs are actually part of the introducer device. Such a design would alleviate the need for reintroducing the introduction device to withdraw the elongated member therefrom for removal of the first and second legs.

Figure 57:
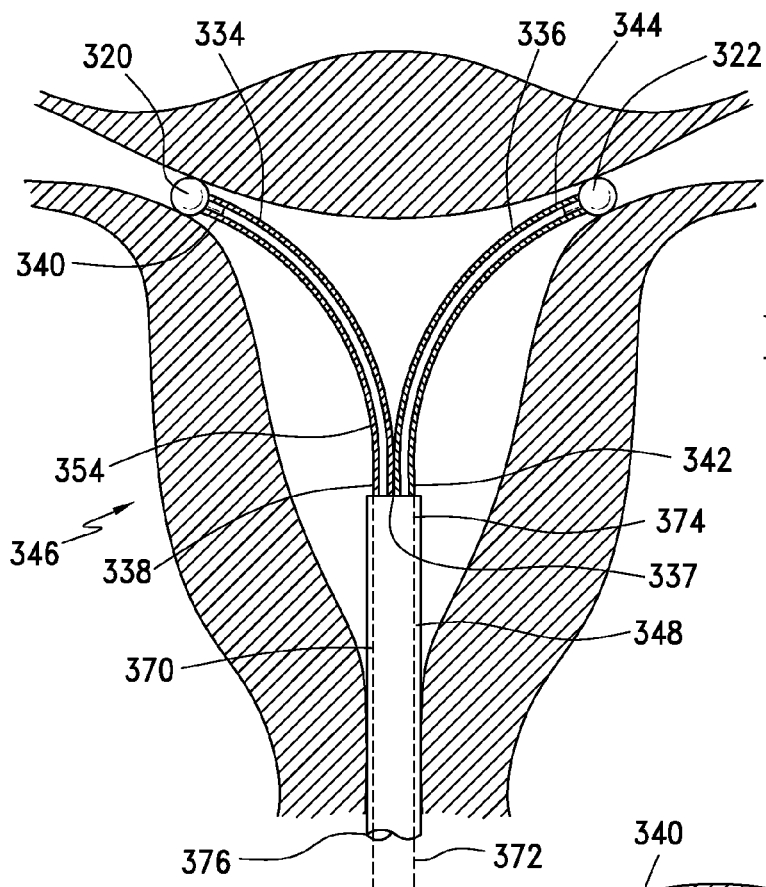
FIGS. 57 and 58 show an alternate embodiment in accordance with the present invention.
Figure 58:
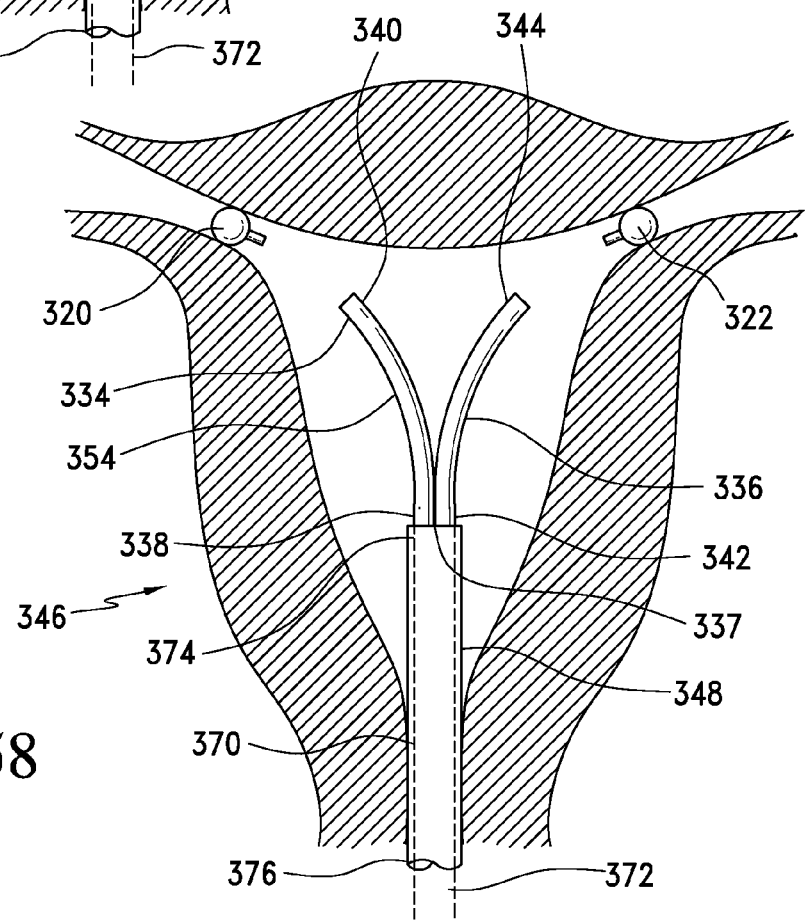

More particularly, and with reference to FIGS. 57 and 58, the delivery apparatus 346 includes a small caliber longitudinal delivery container 348 which forms part of the delivery apparatus 346. As with the embodiment described above, the delivery container 348 is shaped and dimensioned for advancement into the uterine cavity through the vagina and cervix. The delivery apparatus 346 further includes a delivery rod 354 extending through the delivery container 348. The delivery rod 354 extends through the delivery container 348 for movement relative thereto in a manner allowing for placement of orifice plugs 320, 322 within the fallopian tubes 14.

As such, the delivery rod 354 includes an elongated primary rod member 370 having a first end 372 and a second end 374. The first end 372 of the primary rod member 370 is shaped and dimensioned to extend from the proximal end 376 of the delivery container 348 for actuation by a user of the present intrauterine occlusion device. Resilient first and second legs 334, 336 extend from the second end 374 of the primary rod member 370. The first leg 334 includes a first end 338 and second end 340, and the second leg 336 includes a first end 342 and second end 344. The first ends 338, 342 of the respective first and second legs 334, 336 are respectively connected at the second end 374 of the primary rod member 370, while the second ends 340, 344 of the first and second legs 334, 336 are respectively free and are provided with, and selectively coupled to, the respective first and second orifice plugs 320, 322 for release of the orifice plugs 320, 322 within the fallopian tube 14. A connection member 337 resiliently couples the first ends 338, 342 of the first and second legs 334, 336 to the primary rod member 370 in a manner biasing the second ends 340, 344 of the first and second legs 334, 336 from each other when they are not restrained in a manner discussed below in greater detail.

With this in mind, the first leg 334 and the second leg 336 are angularly oriented relative to each other creating a substantially V-shape when the first leg 334 and the second leg 336 are allowed to move away from each other based upon the outward bias inherent in the connection member 337. The inherent bias in the connection member 337 is created through the utilization of spring materials or shape memory materials in the construction of the delivery rod 354, in particular, the connection member 337.

In addition, and in accordance with a preferred embodiment, the first leg 334 and the second leg 336 are formed with an outward bow when fully extended. The bias causing the outward bow stores further energy when the delivery rod 354 is compressed for storage and deployment. In accordance with a preferred embodiment, when the first and second legs 334, 336 are entirely unrestrained the first and second legs 334, 336 will form a maximum angle of approximately 150 degrees. This angle forms a geometry preventing the first and second legs 334, 336 from moving away from a fundamentally centralized location in the uterine cavity. That is, the shape of the first and second legs 334, 336, a sort of triangle, only spreads so wide so that it would bump into the walls of the uterine cavity, that way staying located in the center of the uterine cavity.

In practice, the first and second legs 334, 336, with the first and second orifice plugs 320, 322 secured thereto, are released by pushing the delivery rod 354 from its storage position within the delivery container 348, preferably, while pulling the delivery container 348 back so as to prevent damage to the uterus. This releases the present first and second legs 344, 346, as well as the respective first and second orifice plugs 320, 322, from within the delivery container 348 and allows the first and second legs 334, 336 (with the primary rod member 370 secured thereto) to take a shape of a "Y". The delivery rod 354 is further advanced within the uterine cavity. As the first and second legs 334, 336 open with the first and second legs 334, 336 moving apart, the orifice plugs 320, 322 distally reach the back wall of the uterine cavity, and direct themselves to the orifices 12 of the fallopian tubes 14 until they seat at the orifices 12 of the fallopian tubes 14 or within the fallopian tubes 14. At that point when the delivery rod 354 can be compressed against the fallopian tube orifices 12, the first and second orifice plugs 320, 322 are released from the first and second legs 334, 336.

Figure 59:
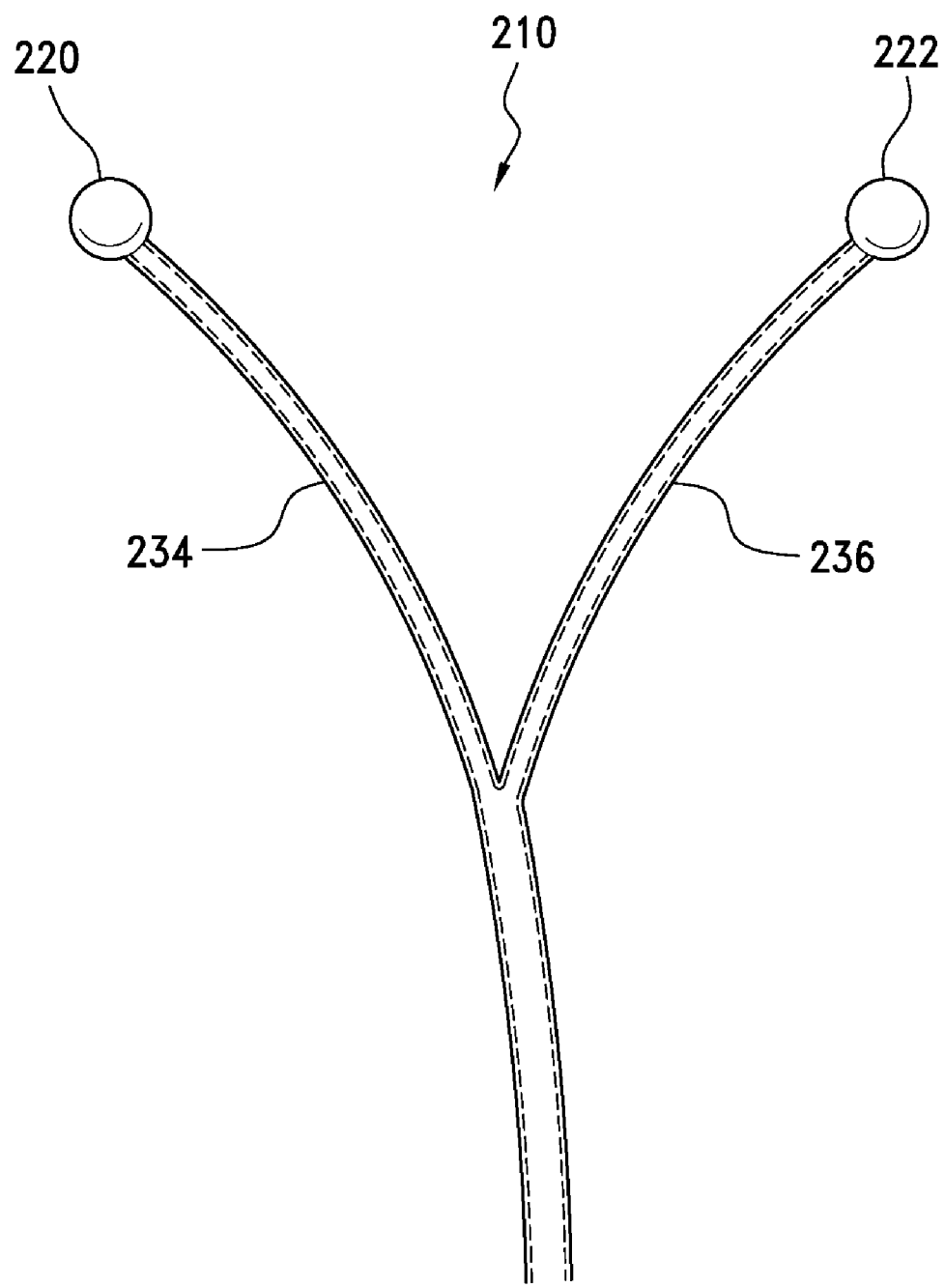
FIG. 59 is a schematic view of an alternate embodiment of an intrauterine occlusion device in accordance with the present invention.

In accordance with an alternate embodiment and with reference to FIG. 59, the intrauterine occlusion device 210 is provided with an elongated member 218 having hollow, tubular first and second legs 234, 236 allowing for the transport of an injectable material to the orifice plugs 220, 222. As such, and in accordance with this embodiment, the orifice plugs 220, 222 are made of a material (for example, a porous material) allowing transport of the injectable material from the first and second legs 234, 236, through the orifice plugs 220, 222 and to the selected tissue.

Figure 60:
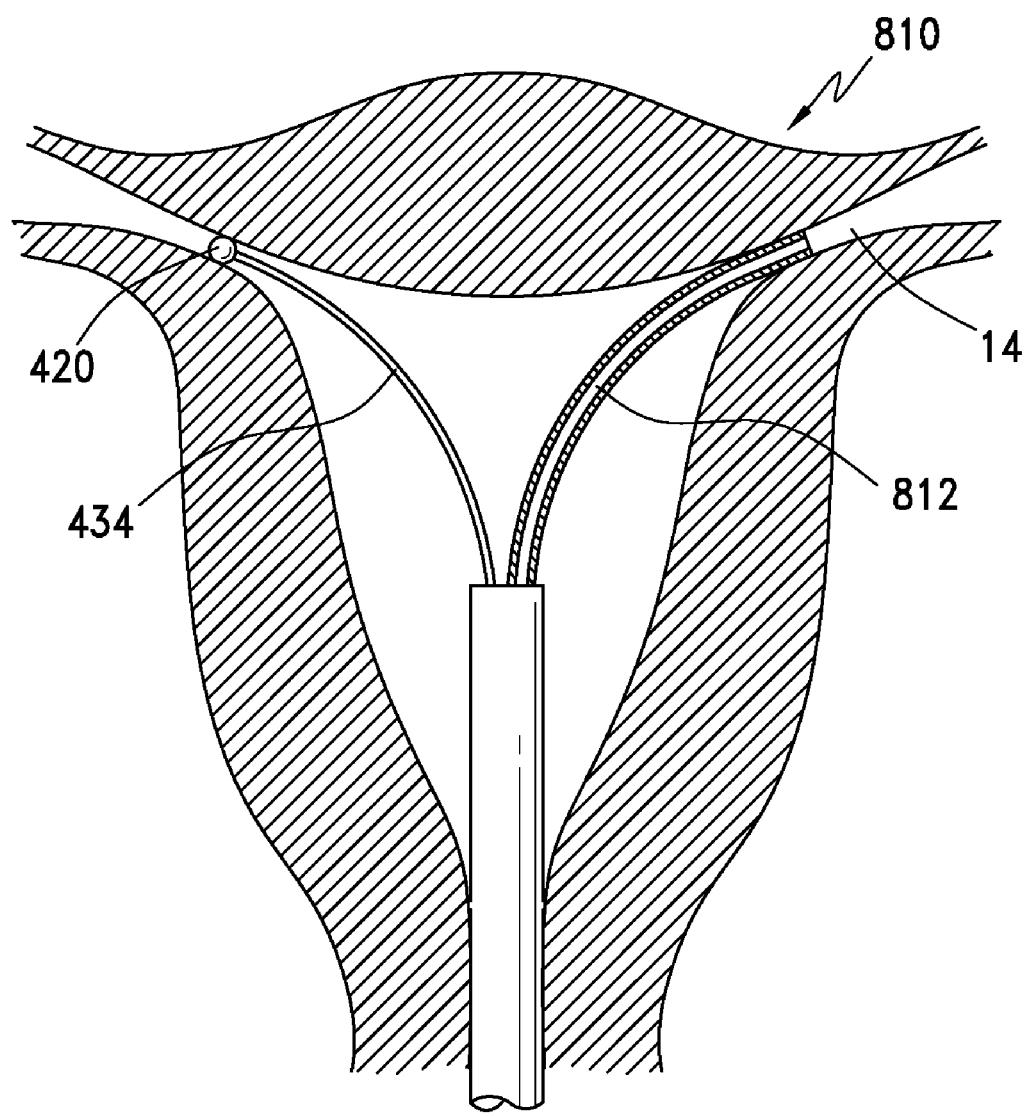
FIG. 60 shows an alternate embodiment in accordance with the present invention.

Referring now to FIG. 60, the concepts underlying the present invention may be applied to an introducer device 810 allowing easy access to the fallopian tubes 14. In accordance with such an embodiment, a medical device or a hysteroscope could be delivered easily into the fallopian tube 14 via a channel 812 which is biased to one or the other fallopian tube 14 through the utilization of a biased arm 434 having an orifice plug 420 secured thereto. As such, by positioning the orifice plug 420 within the fallopian tube 14 and allowing the device channel 812 to bias in the opposite direction the device channel 812 is directed into the other fallopian tube 14.

As those skilled in the art will certainly appreciate, a variety of embodiments have been disclosed above for implementation of the present invention. These various embodiments may be utilized alone or in combination, and various features may be combined to achieve results remaining within the spirit of the present invention.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An intrauterine device for positioning at or within orifices of fallopian tubes, the intrauterine device comprising:
a resilient body including an elongated member having a first end and a second end, the elongated member further including a first leg ending with the first end of the elongated member, a second leg ending with the second end of the elongated member and a connection member positioned therebetween; and
a first orifice plug secured at the first end of the elongated member and a second orifice plug secured at the second end of the elongated member, the first and second orifice plugs being shaped and dimensioned to seat at the orifices of the fallopian tubes or within the fallopian tubes as the elongated member spreads outwardly with the first end and second end moving apart, wherein the first orifice plug and the second orifice plug slide along the resilient body.

2. The intrauterine device according to claim 1, wherein upon insertion, the first orifice plug and the second orifice plug are located at a position adjacent the connection member linking the first leg and second leg, and the first orifice plug and the second orifice plug are respectively moved upwardly along the first leg and the second leg to a position adjacent the second ends of the respective first leg and the second legs where the first orifice plug and the second orifice plug are positioned within the fallopian tubes.

3. The intrauterine device according to claim 2, wherein each of the first orifice plug and the second orifice plug includes a central bearing aperture through which the resilient body passes.

4. An intrauterine device for positioning at or within orifices of fallopian tubes, the intrauterine device comprising:
a resilient body including an elongated member having a first end and a second end, the elongated member further including a first leg ending with the first end of the elongated member, a second leg ending with the second end of the elongated member and a connection member positioned therebetween; and
a first orifice plug secured at the first end of the elongated member and a second orifice plug secured at the second end of the elongated member, the first and second orifice plugs being shaped and dimensioned to seat at the orifices of the fallopian tubes or within the fallopian tubes as the elongated member spreads outwardly with the first end and second end moving apart, wherein the first orifice plug and the second orifice plug are releasably secured to the respective first end and second end of the resilient body via a snap-type connection.

5. The intrauterine device according to claim 4, wherein each of the first orifice plug and the second orifice plug includes a central cavity having a resilient external flange controlling access to the central cavity and each of the first leg and the second leg includes a ball at a distal end thereof, the ball being slightly larger than the flange, wherein applied pressure to the flange will allow pushing of the ball therethrough and into the central cavity of the respective first orifice plug and the second orifice plug such that the respective first orifice plug and second orifice plug are selectively secured to the first end and the second end of the resilient body until such a time that the respective first leg and the second leg are pulled from the first orifice plug and the second orifice plug to withdraw the ball from the central cavity and through the flange.

6. An intrauterine device for positioning at or within orifices of fallopian tubes, the intrauterine device comprising:
a resilient body including an elongated member having a first end and a second end, the elongated member further including a first leg ending with the first end of the elongated member, a second leg ending with the second end of the elongated member and a connection member positioned therebetween; and
a first orifice plug secured at the first end of the elongated member and a second orifice plug secured at the second end of the elongated member, the first and second orifice plugs being shaped and dimensioned to seat at the orifices of the fallopian tubes or within the fallopian tubes as the elongated member spreads outwardly with the first end and second end moving apart, wherein the first orifice plug and the second orifice plug are releasably secured to the respective first end and second end of the resilient body via a resorbable coupling member.

7. An intrauterine device for positioning at or within orifices of fallopian tubes, the intrauterine device comprising:
a resilient body including an elongated member having a first end and a second end, the elongated member further including a first leg ending with the first end of the elongated member, a second leg ending with the second end of the elongated member and a connection member positioned therebetween; and
a first orifice plug secured at the first end of the elongated member and a second orifice plug secured at the second end of the elongated member, the first and second orifice plugs being shaped and dimensioned to seat at the orifices of the fallopian tubes or within the fallopian tubes as the elongated member spreads outwardly with the first end and second end moving apart;
wherein the first leg includes a first end and a second end, the second end being connected to the first orifice plug, and the second end of the first leg includes a reduced diameter section allowing for greater flexibility in an area adjacent the first orifice plug, and the second leg includes a first end and a second end, the second end being connected to the second orifice plug, and the second end of the second leg includes a reduced diameter section allowing for greater flexibility in an area adjacent the second orifice plugs.

8. An intrauterine device for positioning at or within orifices of fallopian tubes, the intrauterine device comprising:
a resilient body including an elongated member having a first end and a second end, the elongated member further including a first leg ending with the first end of the elongated member, a second leg ending with the second end of the elongated member and a connection member positioned therebetween; and
a first orifice plug secured at the first end of the elongated member and a second orifice plug secured at the second end of the elongated member, the first and second orifice plugs being shaped and dimensioned to seat at the orifices of the fallopian tubes or within the fallopian tubes as the elongated member spreads outwardly with the first end and second end moving apart, wherein the first orifice plug includes a plurality of orifice plug members.

9. The intrauterine device according to claim 8, wherein the orifice plug members increase in size as they move from a second end of the first leg to a more proximal position along the first leg.

10. The intrauterine device according to claim 9, wherein a distal most orifice plug member is spherical and each of the remaining orifice plug members includes a distal end and a proximal end and each of the orifice plug members is formed in the shape of a substantially truncated cone with a diameter thereof increasing as the orifice plug member extends from the distal end thereof to the proximal end thereof.

11. An intrauterine device for positioning at or within orifices of fallopian tubes, the intrauterine device comprising:
a resilient body including an elongated member having a first end and a second end, the elongated member further including a first leg ending with the first end of the elongated member, a second leg ending with the second end of the elongated member and a connection member positioned therebetween; and
a first orifice plug secured at the first end of the elongated member and a second orifice plug secured at the second end of the elongated member, the first and second orifice plugs being shaped and dimensioned to seat at the orifices of the fallopian tubes or within the fallopian tubes as the elongated member spreads outwardly with the first end and second end moving apart, wherein the first leg and the second leg are tubular allowing for the transport of an injectable material to the respective first orifice plug and the second orifice plug.

12. The intrauterine device according to claim 11, wherein the each of the first and second orifice plugs is made of a material allowing transport of the injectable material from the respective first and second legs through the first and second orifice plugs and to selected tissue.

13. An intrauterine device for positioning at or within orifices of fallopian tubes, the intrauterine device comprising:
a resilient body including an elongated member having a first end and a second end, the elongated member further including a first leg ending with the first end of the elongated member, a second leg ending with the second end of the elongated member and a connection member positioned therebetween; and
a first orifice plug secured at the first end of the elongated member and a second orifice plug secured at the second end of the elongated member, the first and second orifice plugs being shaped and dimensioned to seat at the orifices of the fallopian tubes or within the fallopian tubes as the elongated member spreads outwardly with the first end and second end moving apart, wherein the resilient body applies a load of approximately 5 to 50 grams when the first orifice plug and the second orifice plug are between approximately 18 mm and 54 mm apart.

14. The intrauterine device according to claim 13, wherein the first orifice plug and the second orifice plug are composed of materials encouraging tissue in-growth.

15. The intrauterine device according to claim 13, wherein the resilient body extends to spread the first orifice plug and the second orifice plug, when deployed within respective orifices of the fallopian tubes, from approximately 18 mm to approximately 54 mm.

16. The intrauterine device according to claim 15, wherein a substantially constant load is applied by the resilient body when the first orifice plug and the second orifice plug are spaced within the range of approximately 18 mm to approximately 54 mm.

17. The intrauterine device according to claim 16, wherein the load applied is between approximately 15 and 30 grams.

18. An intrauterine device for positioning at or within orifices of fallopian tubes, the intrauterine device comprising:
a first leg and second leg connected to each other for controlled relative movement, wherein the first leg includes a first end and a second end wherein a first orifice plug is secured to the second end of the first leg and the second leg includes a first end and a second end wherein a second orifice plug is secured to the second end of the second leg; and
a clamping member connecting the first leg to the second leg for controlled relative movement of the first leg and the second leg;
wherein the first leg and the second leg are selectively moveable, via the clamping member, to adjust a distance between the first orifice plug and the second orifice plug.

19. The intrauterine device according to claim 18, wherein the clamping member is an elongated member including first and second apertures shaped and dimensioned for receiving the respective first ends of the first leg and second leg in a manner permitting relative movement of the first leg and the second leg, and ultimately, the first and second orifice plugs, as the first leg and the second leg are moved within the clamping member.

20. The intrauterine device according to claim 19, wherein the clamping member is crimped to lock the first leg and the second leg in position relative to the clamping member.

21. An intrauterine device for positioning at or within orifices of fallopian tubes, the intrauterine device comprising:
a first leg and second leg connected to each other for controlled relative movement, wherein the first leg includes a first end and a second end wherein a first orifice plug is secured to the second end of the first leg and the second leg includes a first end and a second end wherein a second orifice plug is secured to the second end of the second leg, wherein the first leg and the second leg are selectively moveable to adjust a distance between the first orifice plug and the second orifice plug, and wherein the respective first ends of the first and second legs are formed in a telescopic mating relationship.

22. The intrauterine device according to claim 21, wherein the first end of the first leg includes a central threaded passageway shaped and dimensioned for receiving the threaded first end of the second leg in a threaded mating configuration.

23. An intrauterine device for positioning at or within orifices of fallopian tubes, the intrauterine device comprising:
a first leg and second leg connected to each other for controlled relative movement, wherein the first leg includes a first end and a second end wherein a first orifice plug is secured to the second end of the first leg and the second leg includes a first end and a second end wherein a second orifice plug is secured to the second end of the second leg, wherein the first leg and the second leg are selectively moveable to adjust a distance between the first orifice plug and the second orifice plug, and wherein the first orifice plug and the second orifice plug are composed of materials encouraging tissue in-growth.

24. A method for occluding the fallopian tubes, comprising the following steps:
delivering an occlusion device into the uterine cavity, the occlusion device including an elongated member with a first end and second end, and a first orifice plug secured at the first end of the elongated member and a second orifice plug secured at the second end of the elongated member;
causing the occlusion device to apply pressure within the uterine cavity in a manner causing irritation and encouraging tissue in-growth into the first orifice plug and the second orifice plug, wherein the occlusion device applies a load of approximately 5 to 50 grams.

25. The method according to claim 24, wherein the first and second orifice plugs seat at respective orifices of fallopian tubes or within the fallopian tubes.

26. The method according to claim 24, wherein the load applied is between approximately 15 and 30 grams.

27. The method according to claim 24, wherein the first orifice plug and the second orifice plug are composed of materials encouraging tissue in-growth.

* * * * *